United States Patent
Kolkman et al.

(10) Patent No.: US 10,100,110 B2
(45) Date of Patent: Oct. 16, 2018

(54) SEQUENCES DIRECTED AGAINST HEPATOCYTE GROWTH FACTOR (HGF) AND POLYPEPTIDES COMPRISING THE SAME FOR THE TREATMENT OF CANCERS AND/OR TUMORS

(71) Applicant: Ablynx N.V., Zwijnaarde (BE)

(72) Inventors: Joost Alexander Kolkman, Maarn (NL); Hilde Adi Pierrette Revets, Meise (BE); Jo Vercammen, Sint-Pieters-Leeuw (BE); Augustinus Antonius Maria Silvester van Dongen, Utrecht (NL)

(73) Assignee: Ablynx, N.V., Ghent-Zwijnaarde (BE)

( * ) Notice: Subject to any disclaimer, the term of this patent is extended or adjusted under 35 U.S.C. 154(b) by 0 days.

(21) Appl. No.: 15/586,369

(22) Filed: May 4, 2017

(65) Prior Publication Data
US 2017/0334983 A1 Nov. 23, 2017

Related U.S. Application Data

(63) Continuation of application No. 14/373,375, filed as application No. PCT/EP2013/050724 on Jan. 16, 2013, now Pat. No. 9,670,275.

(60) Provisional application No. 61/589,569, filed on Jan. 23, 2012.

(51) Int. Cl.
| | |
|---|---|
| *A61K 39/395* | (2006.01) |
| *C07K 16/22* | (2006.01) |
| *C07K 16/28* | (2006.01) |
| *G01N 33/574* | (2006.01) |
| *A61K 39/00* | (2006.01) |

(52) U.S. Cl.
CPC .......... *C07K 16/22* (2013.01); *C07K 16/2863* (2013.01); *G01N 33/57488* (2013.01); *A61K 2039/505* (2013.01); *C07K 2317/22* (2013.01); *C07K 2317/31* (2013.01); *C07K 2317/565* (2013.01); *C07K 2317/567* (2013.01); *C07K 2317/569* (2013.01); *C07K 2317/626* (2013.01); *C07K 2317/76* (2013.01); *C07K 2317/92* (2013.01)

(58) Field of Classification Search
None
See application file for complete search history.

(56) References Cited

U.S. PATENT DOCUMENTS 9,670,275 B2 6/2017 Kolkman et al.

FOREIGN PATENT DOCUMENTS

| WO | WO 2010/136482 A1 | 12/2010 |
| WO | WO 2012/042026 A1 | 4/2012 |
| WO | WO 2012/059561 A1 | 5/2012 |
| WO | WO 2012/059562 A1 | 5/2012 |

OTHER PUBLICATIONS

Birchmeier et al., Met, metastasis, motility and more. Nat Rev Mol Cell Biol. Dec. 2003;4(12):915-25.
Bottaro et al., Identification of the hepatocyte growth factor receptor as the c-met proto-oncogene product. Science. Feb. 15, 1991;251(4995):802-4.
Burgess et al., Fully human monoclonal antibodies to hepatocyte growth factor with therapeutic potential against hepatocyte growth factor/c-Met-dependent human tumors. Cancer Res. Feb. 1, 2006;66(3):1721-9. Erratum in: Cancer Res. Jun. 1, 2006;66(11):5976.
Cooper et al., Molecular cloning of a new transforming gene from a chemically transformed human cell line. Nature. Sep. 6-11, 1984;311(5981):29-33.
Matsumoto et al., NK4 (HGF-antagonist/angiogenesis inhibitor) in cancer biology and therapeutics. Cancer Sci. Apr. 2003;94(4):321-7.
Ponzetto et al., A novel recognition motif for phosphatidylinositol 3-kinase binding mediates its association with the hepatocyte growth factor/scatter factor receptor. Mol Cell Biol. Aug. 1993;13(8):4600-8.
Vosjan et al., Nanobodies targeting the hepatocyte growth factor: potential new drugs for molecular cancer therapy. Mol Cancer Ther. Apr. 2012;11(4):1017-25. doi:10.1158/1535-7163.MCT-11-0891. Epub Feb. 7, 2012.

*Primary Examiner* — Marianne P Allen
(74) *Attorney, Agent, or Firm* — Wolf, Greenfield & Sacks, P.C.

(57) ABSTRACT

The present invention relates to biological materials against HGF and more in particular to polypeptides, nucleic acids encoding such polypeptides; to methods for preparing such polypeptides; to host cells expressing or capable of expressing such polypeptides; to compositions and in particular to pharmaceutical compositions that comprise such polypeptides, for prophylactic, therapeutic or diagnostic purposes. In particular, the biological materials of the present invention inhibit binding of HGF to its receptor c-Met.

8 Claims, 8 Drawing Sheets

Specification includes a Sequence Listing.

FIG. 3

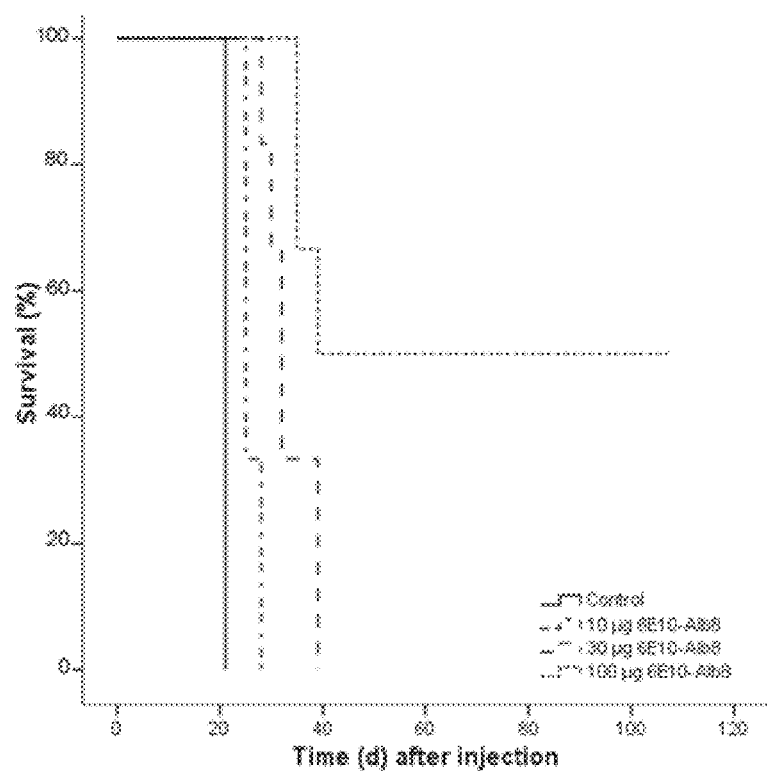

SEQUENCES DIRECTED AGAINST HEPATOCYTE GROWTH FACTOR (HGF) AND POLYPEPTIDES COMPRISING THE SAME FOR THE TREATMENT OF CANCERS AND/OR TUMORS

RELATED APPLICATIONS

This application is a continuation of U.S. patent application Ser. No. 14/373,375, filed Jul. 21, 2014, now issued as U.S. Pat. No. 9,670,275, which is a national stage filing under 35 U.S.C. § 371 of international application PCT/EP2013/050724, filed Jan. 16, 2013, which was published under PCT Article 21(2) in English, and claims the benefit under 35 U.S.C. § 119(e) of U.S. provisional application Ser. No. 61/589,569, filed Jan. 23, 2012, the disclosures of which are incorporated by reference herein in their entireties.

FIELD OF THE INVENTION

The present invention relates to biological materials related to HGF and more in particular to polypeptides, nucleic acids encoding such polypeptides; to methods for preparing such polypeptides; to host cells expressing or capable of expressing such polypeptides; to compositions and in particular to pharmaceutical compositions that comprise such polypeptides, for prophylactic, therapeutic or diagnostic purposes.

BACKGROUND

Receptor tyrosine kinases (RTKs) are key regulators of critical cellular processes such as cell growth, differentiation, neo-vascularization, and tissue repair. In addition to their importance in normal physiology, aberrant expression of certain RTKs has been implicated in the development and progression of many types of cancer. These RTKs have emerged as promising drug targets for cancer therapy.

The RTK c-Met is the cell surface receptor for Hepatocyte Growth Factor (HGF), also known as scatter factor (Cooper et al. Nature 1984; 311:29-33; Bottaro et al. Science 1991; 251:802-4). HGF is a 90 kD multidomain glycoprotein that is highly related to members of the plasminogen serine protease family. Hepatocyte Growth Factor is secreted as a single-chain, inactive polypeptide by mesenchymal cells, and is cleaved by serine proteases into a 69-kDa alpha-chain and 34-kDa beta-chain. (Birchmeier et al. Nat Rev Mol Cell Biol 2003; 4.915-25). The α chain $NH_2$-terminal portion contains the high-affinity c-Met receptor-binding domain, but the β chain is required to interact with the c-Met receptor for receptor activation (Matsumoto & Nakamura Cancer Sci 2003; 94:321-7). HGF is the only known ligand for the c-Met receptor (Birchmeier et al. Nat Rev Mol Cell Biol 2003; 4:915-25). The c-Met receptor, like its ligand, is a disulfide-linked heterodimer consisting of extracellular a and β chains. The α chain, heterodimerized to the amino-terminal portion of the β chain, forms the major ligand-binding site in the extracellular domain. The carboxy-terminal tail of c-Met includes tyrosines Y1349 and Y1356, which, when phosphorylated, serve as docking sites for intracellular adaptor proteins, leading to downstream signaling (Ponzetto et al. Mol Cell Biol 1993; 13:4600-8). The c-Met/HGF pathway is the main driver of the invasive growth program, a series of events including cell proliferation, scattering, migration, survival, and invasion of tissues. Under normal circumstances, the invasive growth program is essential for correct organ formation during embryogenesis and in adult homeostasis. Importantly, it is also involved in tumorigenesis, tumor angiogenesis and metastasis. The c-Met receptor is expressed in the epithelial cells of many organs during embryogenesis and also in adulthood, like liver, prostate, pancreas, muscle, kidney and bone marrow. In tumor cells, c-Met activation triggers diverse series of signaling cascades resulting in cell growth, proliferation, invasion, metastasis formation and escape from apoptosis. Overexpression of HGF and c-Met is indicative of increased aggressiveness of tumors and poor prognostic outcome of cancer patients. HGF and c-Met expression have been observed in most solid tumors, including; head and neck, bladder, breast, cervical, colorectal, gastric, liver, lung, ovarian, pancreatic, prostate, renal and thyroid cancers.

SUMMARY OF THE INVENTION

Targeting the HGF/c-Met pathway provides a therapeutic opportunity. Preventing ligand/receptor binding would result in growth inhibition and tumor regression by inhibiting proliferation and enhancing apoptosis. Since HGF, which is also known as scatter factor, is more elusive compared to the membrane bound receptor c-Met, most studies have focused on the receptor. Indeed, one-armed 5D5 (OA5D5, MetMAb; Genentech) is a humanized, monovalent, antagonistic anti-c-Met antibody derived from the agonistic monoclonal antibody 5D5 (Nguyen et al. Cancer Gene Ther 2003; 10:840-9).

On the other hand, Cao et al. needed a combination of 3 monoclonal antibodies to achieve neutralizing activity to HGF in glioma xenograft tumors, and suggested that the complex heterodimeric structure of HGF makes it necessary to simultaneously target multiple HGF epitopes by combining mAbs (Cao et al., Proc Natl Acad Sci USA 2001; 98:7443-8).

AMG102 (rilotumumab; Amgen, Inc.) was identified in an extensive screen, resulting in 3 potential candidates, of which each recognized a different epitope. Although AMG102 had intermediate affinity for HGF (as judged by binding affinity), it was the only mAb identified that completely blocked the binding of HGF to c-Met (Kim et al. 2006 Clin Cancer Res 12:1292-1298).

Several lines of evidence indicate that the HGF/c-Met pathway is also a therapeutic target in metastatic renal cell carcinoma (mRCC). Nevertheless, Schöffski et al. demonstrate that no significant growth inhibition occurred with AMG102 (Schöffski et al. 2010 BJU Int doi:10.1111/j.1464). Similarly, HGF and its receptor c-Met have been implicated in the pathogenesis of glioblastoma (GBM), but Wen and colleagues showed in a phase II study that AMG102 monotherapy treatment at doses up to 20 mg/kg was not associated with significant antitumor activity in the selected patient groups (Wen et al. 2011 Neuro-Oncology doi:10.1093/neuonc/noq198).

Indeed, according to the current biomedical understanding, drug resistance is caused by a complex network of proteins responsible for the regulation of cell proliferation, apoptosis, migration and invasion. Currently, no systematic description of growth factor receptor dependent signaling pathways is available. The molecular pathways by which HGF/c-Met abnormalities drive cancer development are extremely complex and involve many interconnected signaling pathways, including both signaling molecules (such as Ras and PI3K), receptors (such as EGFR), and growth factors (such as VEGF).

Targeting serum albumin to extend the half-life of biological molecules such as e.g., immunoglobulin single variable domains has been described e.g., in WO2008/028977, WO04/041865 and WO08/122787.

The art is in need of effective and/or more potent HGF antagonists having superior selectivity and specificity over small molecule drugs, an ability to modulate half-life, and/or a superior tumour targeting, e.g., are smaller than conventional antibodies and have an albumin-based tumour targeting strategy. Furthermore, the art is in need of diagnostically, preventatively, and/or therapeutically suitable HGF antagonists such as provided herein.

The present invention relates to an immunoglobulin single variable domain that can bind (to) HGF (SEQ ID NO: 1) with a Kd of less than 50 nM. In an embodiment, said immunoglobulin single variable domain can inhibit binding of HGF, preferably human HGF (SEQ ID NO: 1) to c-Met, preferably human c-Met (SEQ ID NO: 4), with a Kd of less than 50 nM, and optionally a maximal HGF displacement level of 60% to 80% or more. In particular, wherein the immunoglobulin single variable domain comprises an amino acid sequence of formula 1: FR1-CDR1-FR2-CDR2-FR3-CDR3-FR4 (1); wherein FR1 to FR4 refer to framework regions 1 to 4 and are framework regions (FRs) of an immunoglobulin single variable domain; and wherein CDR1 is chosen from the group consisting of: SEQ ID NOs: 40-51, polypeptides that have at least 80% amino acid identity with SEQ ID NOs: 40-51, and polypeptides that have 3, 2, or 1 amino acid difference with SEQ ID NOs: 40-51; and wherein CDR2 is chosen from the group consisting of: SEQ ID NOs: 64-75; polypeptides that have at least 80% amino acid identity with SEQ ID NOs: 64-75; and polypeptides that have 3, 2, or 1 amino acid difference with SEQ ID NOs: 64-75; and wherein CDR3 is chosen from the group consisting of: SEQ ID NOs: 88-99; polypeptides that have at least 80% amino acid identity with at least one of the immunoglobulin single variable domains of SEQ ID NOs: 88-99; and polypeptides that have 3, 2, or 1 amino acid difference with SEQ ID NOs: 88-99; even more preferably, wherein the framework regions (FRs) have a sequence identity of more than 80% with the FRs of SEQ ID NOs: 7-25.

The present invention further relates to an immunoglobulin single variable domain as described herein, wherein the immunoglobulin single variable domain comprises an amino acid sequence with the formula 1: FR1-CDR1-FR2-CDR2-FR3-CDR3-FR4 (1); wherein FR1 to FR4 refer to framework regions 1 to 4 and are framework regions of an immunoglobulin single variable domain; wherein CDR1 is SEQ ID NO: 40, wherein CDR2 is SEQ ID NO: 64, 67, 69 or 72; and wherein CDR3 is SEQ ID NO: 88, 91, 93 or 96; wherein CDR1 is SEQ ID NO: 40, wherein CDR2 is SEQ ID NO: 64; and wherein CDR3 is SEQ ID NO: 88; or wherein CDR1 is SEQ ID NO: 45, wherein CDR2 is SEQ ID NO: 69; and wherein CDR3 is SEQ ID NO: 93.

The present invention also relates to a polypeptide comprising an immunoglobulin single variable domain as described herein; preferably wherein the polypeptide is selected from the group consisting of polypeptides that have an amino acid sequence with a sequence identity of more than 80% with SEQ ID NOs: 7 to 25; even more preferably wherein the polypeptide is selected from the group consisting of polypeptides that have an amino acid sequence with a sequence identity of more than 80% with SEQ ID NOs: 7 or 18; even more preferably additionally comprising an immunoglobulin single variable domain binding human serum albumin such as e.g. Alb8 (SEQ ID NO: 115) or Alb11 (SEQ ID NO: 114).

In addition, the present invention relates to an immunoglobulin single variable domain as described herein or the polypeptide as described herein, wherein the IC50 in an AlphaScreen® assay is 30 nM or lower, or even wherein the IC50 in an Alphascreen® assay is 3 nM or lower. The present invention also relates to a nucleic acid sequence encoding i) for an immunoglobulin single variable domain as described herein; or ii) for a polypeptide as described herein.

Moreover, the present invention relates to a pharmaceutical composition comprising i) for an immunoglobulin single variable domain as described herein; or ii) for a polypeptide as described herein; and optionally a pharmaceutically acceptable excipient.

Additionally, the present invention relates to an immunoglobulin single variable domain as described herein; or ii) for a polypeptide as described herein, for use in treating cancer.

Also, the present invention relates to a method for producing an immunoglobulin single variable domain as described herein; or ii) for a polypeptide as described herein, said method at least comprising the steps of: (a) expressing, in a suitable host cell or host organism or in another suitable expression system, a nucleic acid or nucleotide sequence as described herein; optionally followed by (b) isolating and/or purifying said immunoglobulin single variable domain or said polypeptide.

The present invention also relates to a method for screening immunoglobulin single variable domains directed against HGF and in particular human HGF (SEQ ID NO: 1) that comprises at least the steps of (a) providing a set, collection or library of immunoglobulin single variable domains; and (b) screening said set, collection or library of immunoglobulin single variable domains for immunoglobulin single variable domains that can bind to and/or have affinity for HGF and in particular human HGF (SEQ ID NO: 1); and (c) isolating the amino acid sequence(s) that can bind to and/or have affinity for HGF and in particular human HGF (SEQ ID NO: 1).

BRIEF DESCRIPTION OF THE FIGURES

FIG. 3 aligned sequences of the anti-HGF lead Nanobodies. The cysteine residues are boxed.

FIGS. 8A-8C (FIG. 8A) Therapy study with αHGF Nanobodies in nude mice bearing U87 MG glioblastoma xenografts. Treatment was 3 times a week for 5 weeks. Kaplan Meier survival curves of nude mice treated with different amounts of 1E2-ALB (FIG. 8B) or 6E10-ALB (FIG. 8C). Treatment with all Nanobody concentrations caused significant regression of the established tumors after day 6

Figure 1:
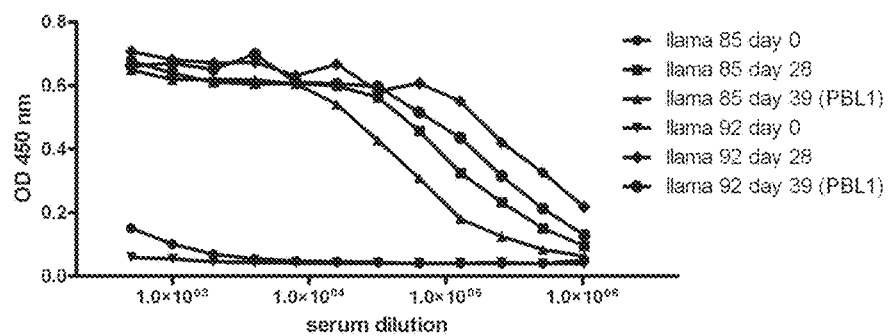
FIG. 1 serum titrations of llama 85 and 092.

(p<0.01), and curative responses after treatment with 30 or 100 μg 1E2-ALB, or 100 μg 6E10-ALB.

DESCRIPTION OF THE INVENTION

Immunoglobulin sequences, such as antibodies and antigen binding fragments derived there from (e.g., immunoglobulin single variable domains) are used to specifically target their respective antigens in research and therapeutic applications. The generation of immunoglobulin single variable domains such as e.g., VHHs may involve the immunization of an experimental animal such as a Llama, construction of phage libraries from immune tissue, selection of phage displaying antigen binding immunoglobulin single variable domains and screening of said domains and engineered constructs thereof for the desired specificities (WO 94/04678). Alternatively, similar immunoglobulin single variable domains such as e.g., dAbs can be generated by selecting phage displaying antigen binding immunoglobulin single variable domains directly from naive or synthetic libraries and subsequent screening of said domains and engineered constructs thereof for the desired specificities (Ward et al., Nature, 1989, 341: 544-6; Holt et al., Trends Biotechnol., 2003, 21(11):484-490; as well as for example WO 06/030220, WO 06/003388 and other published patent applications of Domantis Ltd.). Unfortunately, the use of monoclonal and/or heavily engineered antibodies also carries a high manufacturing cost and may result in suboptimal tumor penetration compared to other strategies.

The present invention relates to particular polypeptides, also referred to as "polypeptides of the invention" or "immunoglobulin single variable domain of the invention" or "ISVD of the invention" that comprise or, more preferably, essentially consist of (i) a first building block consisting essentially of one or more (preferably one) immunoglobulin single variable domain(s), wherein said immunoglobulin single variable domain(s) is (are) directed against HGF and in particular against human HGF; (ii) optionally a second building block consisting essentially of one or more (preferably one) immunoglobulin single variable domain(s), wherein said immunoglobulin single variable domain(s) is (are) directed against serum albumin and in particular against human serum albumin (and even more preferably wherein said immunoglobulin single variable domain is Alb8 or Alb11 (as herein defined)); (iii) optionally a third and/or fourth building block consisting essentially of one or more immunoglobulin single variable domain(s), wherein said immunoglobulin single variable domain(s) is (are) directed against EGFR, in particular human EGFR (hEGFR), and/or is (are) directed against VEGF, in particular human VEGF (hVEGF). Furthermore, the invention also relates to nucleic acids encoding such polypeptides; to methods for preparing such polypeptides; to host cells expressing or capable of expressing such polypeptides; to compositions and in particular to pharmaceutical compositions that comprise such polypeptides, nucleic acids and/or host cells; and to uses of such polypeptides, nucleic acids, host cells and/or compositions for prophylactic, therapeutic or diagnostic purposes. Other aspects, embodiments, advantages and applications of the invention will become clear from the further description herein.

In this study, two αHGF Nanobodies 1E2-ALB and 6E10-ALB were developed and characterized for their potential in diagnosis and therapy of cancer. After labeling with the positron emitter Zirconium-89 the Nanobodies were evaluated in biodistribution studies in nude mice bearing U87 MG glioblastoma xenografts. Besides that, αHGF-Nanobodies were tested as therapeutic agents by inhibiting the binding of HGF to the c-Met receptor in the same mouse model.

Definitions a) Unless indicated or defined otherwise, all terms used have their usual meaning in the art, which will be clear to the skilled person. Reference is for example made to the standard handbooks mentioned in paragraph a) on page 46 of WO 08/020079.

b) Unless indicated otherwise, the term "immunoglobulin single variable domain" or "ISVD" is used as a general term to include but not limited to antigen-binding domains or fragments such as $V_{HH}$ domains or $V_H$ or $V_L$ domains, respectively. The terms antigen-binding molecules or antigen-binding protein are used interchangeably and include also the term Nanobodies. The immunoglobulin single variable domains can be light chain variable domain sequences (e.g., a $V_L$-sequence), or heavy chain variable domain sequences (e.g., a $V_H$-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs", or immunoglobulin sequences that are suitable for use as dAbs, or Nanobodies, including but not limited to $V_{HH}$ sequences. The invention includes immunoglobulin sequences of different origin, comprising mouse, rat, rabbit, donkey, human and camelid immunoglobulin sequences. The immunoglobulin single variable domain includes fully human, humanized, otherwise sequence optimized or chimeric immunoglobulin sequences. The immunoglobulin single variable domain and structure of an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. It is noted that the terms Nanobody or Nanobodies are registered trademarks of Ablynx N.V. and thus may also be referred to as Nanobody® or Nanobodies®, respectively.

c) Unless indicated otherwise, the terms "immunoglobulin sequence", "sequence", "nucleotide sequence" and "nucleic acid" are as described in paragraph b) on page 46 of WO 08/020079.

d) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv.

Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

e) Amino acid residues will be indicated according to the standard three-letter or one-letter amino acid code. Reference is made to Table A-2 on page 48 of the International application WO 08/020079 of Ablynx N.V. entitled "Immunoglobulin single variable domains directed against IL-6R and polypeptides comprising the same for the treatment of diseases and disorders associated with Il-6 mediated signalling".

f) For the purposes of comparing two or more nucleotide sequences, the percentage of "sequence identity" between a first nucleotide sequence and a second nucleotide sequence may be calculated or determined as described in paragraph e) on page 49 of WO 08/020079 (incorporated herein by reference), such as by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position); or using a suitable computer algorithm or technique, again as described in paragraph e) on pages 49 of WO 08/020079 (incorporated herein by reference).

g) For the purposes of comparing two or more immunoglobulin single variable domains or other amino acid sequences such e.g. the polypeptides of the invention etc., the percentage of "sequence identity" between a first amino acid sequence and a second amino acid sequence (also referred to herein as "amino acid identity") may be calculated or determined as described in paragraph f) on pages 49 and 50 of WO 08/020079 (incorporated herein by reference), such as by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein; or using a suitable computer algorithm or technique, again as described in paragraph f) on pages 49 and 50 of WO 08/020079 (incorporated herein by reference).

Also, in determining the degree of sequence identity between two immunoglobulin single variable domains, the skilled person may take into account so-called "conservative" amino acid substitutions, as described on page 50 of WO 08/020079.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

h) Immunoglobulin single variable domains and nucleic acid sequences are said to be "exactly the same" if they have 100% sequence identity (as defined herein) over their entire length.

i) When comparing two immunoglobulin single variable domains, the term "amino acid difference" refers to an insertion, deletion or substitution of a single amino acid residue on a position of the first sequence, compared to the second sequence; it being understood that two immunoglobulin single variable domains can contain one, two or more such amino acid differences.

j) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020079.

k) The term "in essentially isolated form" has the meaning given to it in paragraph j) on pages 52 and 53 of WO 08/020079.

l) The terms "domain" and "binding domain" have the meanings given to it in paragraph k) on page 53 of WO 08/020079.

m) The terms "antigenic determinant" and "epitope", which may also be used interchangeably herein, have the meanings given to it in paragraph I) on page 53 of WO 08/020079.

n) As further described in paragraph m) on page 53 of WO 08/020079, an amino acid sequence (such as an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

o) The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as a polypeptide of the invention) molecule can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as a polypeptide or ISVD of the invention) and the pertinent antigen. Typically, antigen-binding proteins (such as the immunoglobulin single variable domains, and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{12}$ moles/liter (i.e., with an association constant ($K_A$) of $10^8$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ liter/mol) is generally considered to indicate non-specific binding. Preferably, a monovalent immunoglobulin single variable domain of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

p) The half-life of an amino acid sequence, compound or polypeptide of the invention can generally be defined as described in paragraph o) on page 57 of WO 08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2-beta and the area under the curve (AUC). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). The terms "increase in half-life" or "increased half-life" as also as defined in paragraph o) on page 57 of WO 08/020079 and in particular refer to an increase in the t1/2-beta, either with or without an increase in the t1/2-alpha and/or the AUC or both.

q) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

r) An immunoglobulin single variable domain or polypeptide is said to be "specific for" a first target or antigen compared to a second target or antigen when it binds to the first antigen with an affinity/avidity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10.000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10.000 times less or even less than that, than the $K_D$ with which said amino acid sequence or polypeptide binds to the second target or polypeptide. Preferably, when an immunoglobulin single variable domain or polypeptide is "specific for" a first target or antigen compared to a second target or antigen, it is directed against (as defined herein) said first target or antigen, but not directed against said second target or antigen.

s) The terms "cross-block", "cross-blocked" and "cross-blocking" are used interchangeably herein to mean the ability of an immunoglobulin single variable domain or polypeptide to interfere with the binding of the natural ligand HGF to c-Met or with the binding of the natural ligand EGF to EGFR, or with the binding of the natural ligand VEGF to VEGF receptors (such as VEGFR-1R (Flt-1), VEGFR-2 (KDR/Flk-1) and/or VEGFR-3 (Flt-4)), respectively. The extent to which an immunoglobulin single variable domain or polypeptide of the invention is able to interfere with the binding of another compound such as the natural ligand to its target, e.g., c-Met, VEGF or EGFR, and therefore whether it can be said to cross-block according to the invention, can be determined using competition binding assays. One particularly suitable quantitative cross-blocking assay uses a FACS- or an ELISA-based approach or Alphascreen to measure competition between the labelled (e.g., His tagged or biotinylated) immunoglobulin single variable domain or polypeptide according to the invention and the other binding agent in terms of their binding to the target. The experimental part generally describes suitable FACS-, ELISA- or Alphascreen-displacement-based assays for determining whether a binding molecule cross-blocks or is capable of cross-blocking an immunoglobulin single variable domain or polypeptide according to the invention. It will be appreciated that the assay can be used with any of the immunoglobulin single variable domains or other binding agents described herein. Thus, in general, a cross-blocking amino acid sequence or other binding agent according to the invention is for example one which will bind to the target in the above cross-blocking assay such that, during the assay and in the presence of a second amino acid sequence or other binding agent of the invention, the recorded displacement of the immunoglobulin single variable domain or polypeptide according to the invention is between 60% and 100% (e.g., in ELISA/Alphascreen based competition assay) or between 80% to 100% (e.g., in FACS based competition assay) of the maximum theoretical displacement (e.g. displacement by cold (e.g., unlabeled) immunoglobulin single variable domain or polypeptide that needs to be cross-blocked) by the to be tested potentially cross-blocking agent that is present in an amount of 0.01 mM or less (cross-blocking agent may be another conventional monoclonal antibody such as IgG, classic monovalent antibody fragments (Fab, scFv)) and engineered variants (e.g., diabodies, triabodies, minibodies, VHHs, dAbs, VHs, VLs).

t) An amino acid sequence such as e.g. an immunoglobulin single variable domain or polypeptide according to the invention is said to be a "VHH1 type immunoglobulin single variable domain" or "VHH type 1 sequence", if said VHH1 type immunoglobulin single variable domain or VHH type 1 sequence has 85% identity (using the VHH1 consensus sequence as the query sequence and use the blast algorithm with standard setting, i.e., blosom62 scoring matrix) to the VHH1 consensus sequence (SEQ ID NO: 127: QVQLVESGGGLVQPGGSLRLSCAAS-GFTLDYYAIGWFRQAP-GKEREGVSCISSSDG-STYYADSVKGRFTISRDNAKNTVYLQMNSLKPED-TAVYYCAA), and mandatorily has a cysteine in position 50, i.e., C50 (using Kabat numbering).

u) An amino acid sequence such as e.g., an immunoglobulin single variable domain or polypeptide according to the invention is said to be "cross-reactive" for two different antigens or antigenic determinants (such as serum albumin from two different species of mammal, such as human serum albumin and cynomolgus monkey serum albumin) if it is specific for (as defined herein) both these different antigens or antigenic determinants.

v) As further described in paragraph q) on pages 58 and 59 of WO 08/020079 (incorporated herein by reference), the amino acid residues of an immunoglobulin single variable domain are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication), and accordingly FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

w) The Figures, Sequence Listing and the Experimental Part/Examples are only given to further illustrate the invention and should not be interpreted or construed as limiting the scope of the invention and/or of the appended claims in any way, unless explicitly indicated otherwise herein.

Polypeptides of the Invention and Uses Thereof

The polypeptides of the present invention can generally be used to modulate, and in particular inhibit and/or prevent, binding of HGF and in particular human HGF (SEQ ID NO: 1; Swiss Prot database: P14210) to c-Met and in particular human c-Met (SEQ ID NO: 4), and thus to modulate, and in particular inhibit or prevent, the signalling that is mediated by c-Met and in particular human c-Met (SEQ ID NO: 4) and/or HGF and in particular human HGF (Swiss Prot database: P14210), to modulate the biological pathways in which HGF and in particular human HGF (SEQ ID NO: 1) and/or c-Met and in particular human c-Met are involved, and/or to modulate the biological mechanisms, responses and effects associated with such signalling or these pathways (α-HGF building blocks).

As such, the polypeptides and compositions of the present invention can be used for the diagnosis, prevention and treatment of diseases and disorders of the present invention (herein also "diseases and disorders of the present invention") which include, but are not limited to cancer, e.g., carcinomas, gliomas, mesotheliomas, melanomas, lymphomas, leukemias, adenocarcinomas: breast cancer, ovarian cancer, cervical cancer, glioblastoma, multiple myeloma (including monoclonal gammopathy of undetermined significance, asymptomatic and symptomatic myeloma), prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease or AIDS-associated primary effusion lymphoma, neuroectodermnnal tumors, rhabdomyosarcoma (see e.g., Cancer, Principles and practice (DeVita, V. T. et al. eds 1997) for additional cancers); as well as any metastasis of any of the above cancers, as well as non-cancer indications such as nasal polyposis; as well as other disorders and diseases described herein. In particular, the polypeptides and compositions of the present invention can be used for the diagnosis, prevention and treatment of diseases involving HGF mediated metastasis, chemotaxis, cell adhesion, trans endothelial migration, cell proliferation and/or survival, in particular non-small cell lung cancer and multiple myeloma.

Generally, said "diseases and disorders of the present invention" can be defined as diseases and disorders that can be diagnosed, prevented and/or treated, respectively, by suitably administering to a subject in need thereof (i.e., having the disease or disorder or at least one symptom thereof and/or at risk of attracting or developing the disease or disorder) of either a polypeptide or composition of the invention (and in particular, of a pharmaceutically active amount thereof) and/or of a known active principle active against HGF and in particular human HGF (SEQ ID NO: 1) or a biological pathway or mechanism in which HGF and in particular human HGF (SEQ ID NO: 1) is involved (and in particular, of a pharmaceutically active amount thereof).

In particular, the polypeptides of the present invention can be used for the diagnosis, prevention and treatment of diseases and disorders of the present invention which are characterized by excessive and/or unwanted HGF and in particular human HGF (SEQ ID NO: 1) signalling mediated by c-Met and in particular human c-Met or by the pathway(s) in which c-Met and in particular human c-Met is involved (e.g. HGF/c-Met axis). Examples of such diseases and disorders of the present invention will again be clear to the skilled person based on the disclosure herein.

Thus, without being limited thereto, the immunoglobulin single variable domains and polypeptides of the invention can for example be used to diagnose, prevent and/or to treat all diseases and disorders that are currently being diagnosed, prevented or treated with active principles that can modulate HGF and in particular human HGF (SEQ ID NO: 1)-mediated signalling, such as those mentioned in the diseases and prior art cited above. It is also envisaged that the polypeptides of the invention can be used to diagnose, prevent and/or to treat all diseases and disorders for which treatment with such active principles is currently being developed, has been proposed, or will be proposed or developed in the future. In addition, it is envisaged that, because of their favourable properties as further described herein, the polypeptides of the present invention may be used for the diagnosis, prevention and treatment of other diseases and disorders than those for which these known active principles are being used or will be proposed or developed; and/or that the polypeptides of the present invention may provide new methods and regimens for treating the diseases and disorders described herein.

Other applications and uses of the immunoglobulin single variable domains and polypeptides of the invention will become clear to the skilled person from the further disclosure herein.

Generally, it is an object of the invention to provide pharmacologically active agents, as well as compositions comprising the same, that can be used in the diagnosis, prevention and/or treatment of diseases and/or disorders of the invention; and to provide methods for the diagnosis, prevention and/or treatment of such diseases and disorders that involve the administration and/or use of such agents and compositions.

In particular, it is an object of the invention to provide such pharmacologically active agents, compositions and/or methods that have certain advantages compared to the agents, compositions and/or methods that are currently used and/or known in the art. These advantages will become clear from the further description below.

More in particular, it is an object of the invention to provide therapeutic proteins that can be used as pharmacologically active agents, as well as compositions comprising the same, for the diagnosis, prevention and/or treatment of diseases and/or disorders of the invention and of the further diseases and disorders mentioned herein; and to provide methods for the diagnosis, prevention and/or treatment of such diseases and disorders that involve the administration and/or the use of such therapeutic proteins and compositions.

Accordingly, it is a specific object of the present invention to provide immunoglobulin single variable domains that are directed against HGF, in particular against HGF from a warm-blooded animal, more in particular against HGF from a mammal such as e.g. mouse, and especially against human HGF (SEQ ID NO: 1); and to provide proteins and polypeptides comprising or essentially consisting of at least one such immunoglobulin single variable domain.

In particular, it is a specific object of the present invention to provide such immunoglobulin single variable domains and such proteins and/or polypeptides that are suitable for prophylactic, therapeutic and/or diagnostic use in a warm-blooded animal, and in particular in a mammal, and more in particular in a human being.

More in particular, it is a specific object of the present invention to provide such immunoglobulin single variable domains and such proteins and/or polypeptides that can be used for the prevention, treatment, alleviation and/or diagnosis of one or more diseases, disorders or conditions associated with HGF and/or mediated by HGF (such as the diseases, disorders and conditions mentioned herein) in a warm-blooded animal, in particular in a mammal, and more in particular in a human being.

It is also a specific object of the invention to provide such immunoglobulin single variable domains and such proteins and/or polypeptides that can be used in the preparation of pharmaceutical or veterinary compositions for the prevention and/or treatment of one or more diseases, disorders or conditions associated with and/or mediated by HGF (such as the diseases, disorders and conditions mentioned herein) in a warm-blooded animal, in particular in a mammal, and more in particular in a human being.

In the invention, generally, these objects are achieved by the use of the immunoglobulin single variable domains, proteins, polypeptides and compositions that are described herein.

In general, the invention provides immunoglobulin single variable domains that are directed against (as defined herein) and/or can specifically bind (as defined herein) to HGF and in particular human HGF (SEQ ID NO: 1); as well as compounds and constructs, and in particular proteins and polypeptides, that comprise at least one such amino acid sequence or immunoglobulin single variable domain.

More in particular, the invention provides immunoglobulin single variable domains and polypeptides that can bind to HGF and in particular human HGF (SEQ ID NO: 1) with an affinity (suitably measured and/or expressed as a $K_D$-value (actual or apparent), a $K_A$-value (actual or apparent), a $k_{on}$-rate and/or a $k_{off}$-rate, as well as compounds and constructs, and in particular proteins and polypeptides, that comprise at least one such amino acid sequence or immunoglobulin single variable domain.

Also, the immunoglobulin single variable domains and polypeptides that can bind to HGF and in particular human HGF (SEQ ID NO: 1) may be characterized by biological potency, suitably measured and/or expressed as an $IC_{50}$ value, as further described and defined herein, for instance, such as by Alphascreen; as well as compounds and constructs, and in particular proteins and polypeptides, that comprise at least one such amino acid sequence or immunoglobulin single variable domain.

In particular aspect, the immunoglobulin single variable domains and/or polypeptides of the invention:
  bind to human HGF (SEQ ID NO: 1) with an IC50 of 50 nM or lower, more preferably of 30 nM or lower, even more preferably of 20 nM or lower, most preferably of 10 nM or lower, such as 5 nM, in an Alphascreen assay as e.g., described in the experimental part (see e.g., Example 1.5), and wherein the polypeptides comprise only one human HGF binding immunoglobulin single variable domain unit, and wherein full displacement means an average HGF displacement of about 60% to 80% and more, preferably 95% or more (e.g., when measured in an Alphascreen assay;
and/or:
  fully displace human HGF (SEQ ID NO: 1) from human c-Met at an average IC50 value of 50 nM or less, more preferably at an average IC50 value of 30 nM or less, even more preferably at an average IC50 value of 20 nM or less in an assay as e.g. described in the experimental part (e.g., Example 1.6), and wherein the polypeptides comprise only one human HGF binding immunoglobulin single variable domain unit, and wherein full displacement means an average HGF displacement of about 60% to 80% and more, preferably 95% or more (e.g. when measured according to the ligand displacement assay in Example 1.6);

and/or such that they:

bind human HGF (SEQ ID NO: 1) with an average Kd value of 50 nM or less, more preferably at an average Kd value of 30 nM or less, even more preferably at an average Kd value of 20 nM or less, such as less than 10, 9, 8, 7, 6, 5, 4, 3, 2 nM or even less, such as less than 1 nM, or most preferably even less than 0.1 nM.

It should be appreciated that binding of the immunoglobulin single variable domains and/or polypeptides of the invention to (human) HGF may result in displacing (human) HGF from (human) c-Met as described herein. It should further be appreciated that binding of the immunoglobulin single variable domains and/or polypeptides of the invention to (human) HGF may result in inhibiting binding of (human) HGF to its cognate receptor, such as, (human) c-Met as described herein.

Some preferred technical values for binding, displacing, migration or other in vivo and/or in vitro potency of the immunoglobulin single variable domains or polypeptides of the invention to HGF and in particular human HGF (SEQ ID NO: 1) will become clear from the further description and examples herein.

For binding to HGF and in particular human HGF (SEQ ID NO: 1), an amino acid sequence of the invention, such as an ISVD of the invention or a polypeptide of the invention, will usually contain within its amino acid sequence one or more amino acid residues or one or more stretches of amino acid residues (i.e., with each "stretch" comprising two or amino acid residues that are adjacent to each other or in close proximity to each other, i.e., in the primary or tertiary structure of the amino acid sequence) via which the amino acid sequence of the invention can bind to HGF and in particular human HGF (SEQ ID NO: 1), which amino acid residues or stretches of amino acid residues thus form the "site" for binding to HGF and in particular human HGF (SEQ ID NO: 1) (also referred to herein as the "antigen binding site").

The immunoglobulin single variable domains provided by the invention are preferably in essentially isolated form (as defined herein), or form part of a protein or polypeptide of the invention (as defined herein), which may comprise or essentially consist of one or more immunoglobulin single variable domains of the invention and which may optionally further comprise one or more further immunoglobulin single variable domains (all optionally linked via one or more suitable linkers). For example, and without limitation, a preferred aspect of the invention provides a polypeptide consisting essentially of one immunoglobulin single variable domain directed against human HGF and an immunoglobulin single variable domain directed against human serum albumin linked by a peptide linker (as defined herein), so as to provide a bispecific polypeptide of the invention, respectively, and/or an immunoglobulin single variable domain directed against human EGFR also linked by a peptide linker (as defined herein), so as to provide a further bispecific or a trispecific polypeptide of the invention, all as described herein. Such a protein or polypeptide may also be in essentially isolated form (as defined herein).

The immunoglobulin single variable domains and polypeptides of the invention as such preferably essentially consist of a single amino acid chain that is not linked via disulphide bridges to any other amino acid sequence or chain (but that may or may not contain one or more intramolecular disulphide bridges. For example, it is known that agent of the invention—as described herein—may sometimes contain a disulphide bridge between CDR3 and CDR1 or FR2). However, it should be noted that one or more immunoglobulin single variable domains of the invention may be linked to each other and/or to other immunoglobulin single variable domains (e.g., via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat Biotechnol. 2005; 23:1126-36 (incorporated by reference).

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, is in essentially isolated form (as defined herein).

It will also be clear to the skilled person that for pharmaceutical use, the immunoglobulin single variable domains of the invention (as well as compounds, constructs and polypeptides comprising the same) are preferably directed against human HGF and in particular human HGF with SEQ ID NO: 1; whereas for veterinary purposes, the immunoglobulin single variable domains and polypeptides of the invention are preferably directed against HGF from the species to be treated, or at least cross-reactive with HGF from the species to be treated.

Furthermore, an amino acid sequence of the invention may optionally, and in addition to the at least one binding site for binding against HGF and in particular human HGF (SEQ ID NO: 1), contain one or more further binding sites for binding against other antigens, proteins or targets.

The efficacy of the immunoglobulin single variable domains and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include ligand displacement assays (Burgess et al., Cancer Res 2006 66:1721-9), dimerization assays (WO2009/007427A2, Goetsch, 2009), signaling assays (Burgess et al., Mol Cancer Ther 9:400-9), proliferation/survival assays (Pacchiana et al., J Biol Chem 2010 September M110.134031), cell adhesion assays (Holt et al., Haematologica 2005 90:479-88) and migration assays (Kong-Beltran et al., Cancer Cell 6:75-84), endothelial cell sprouting assays (Wang et al., J Immunol. 2009; 183:3204-11), and in vivo xenograft models (Jin et al., Cancer Res. 2008 68:4360-8), as well as the assays and animal models used in the experimental part below and in the prior art cited herein.

Also, according to the invention, immunoglobulin single variable domains and polypeptides that are directed against HGF from a first species of warm-blooded animal may or may not show cross-reactivity with HGF from one or more other species of warm-blooded animal. For example, immunoglobulin single variable domains and polypeptides directed against human HGF and in particular human HGF with SEQ ID NO: 1 may or may not show cross reactivity with HGF from one or more other species of primates (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*)) and/or with HGF from one or more species of animals that are often used in animal models for diseases (for example mouse, rat, rabbit, pig or dog), and in particular in animal models for diseases and disorders associated with HGF and in particular human HGF (SEQ ID NO: 1) (such as the species and animal models mentioned herein). In this respect, it will be clear to the skilled person that such cross-reactivity, when present, may have advantages from a drug development point of view, since it allows the immunoglobulin single variable domains and polypeptides against human HGF and in particular human HGF (SEQ ID NO: 1) to be tested in such disease models.

More generally, immunoglobulin single variable domains and polypeptides of the invention that are cross-reactive with HGF from multiple species of mammal will usually be advantageous for use in veterinary applications, since it will allow the same amino acid sequence or polypeptide to be used across multiple species. Thus, it is also encompassed within the scope of the invention that immunoglobulin single variable domains and polypeptides directed against HGF from one species of animal (such as immunoglobulin single variable domains and polypeptides against human HGF (SEQ ID NO: 1)) can be used in the treatment of another species of animal, as long as the use of the immunoglobulin single variable domains and/or polypeptides provide the desired effects in the species to be treated.

The present invention is in its broadest sense also not particularly limited to or defined by a specific antigenic determinant, epitope, part, domain, subunit or confirmation (where applicable) of HGF and in particular human HGF (SEQ ID NO: 1) against which the immunoglobulin single variable domains and polypeptides of the invention are directed. For example, the immunoglobulin single variable domains and polypeptides may or may not be directed against the HGF/c-Met interaction site, and are as further defined herein.

Furthermore, immunoglobulin single variable domains with dual specificity to HGF and c-Met are within the scope of this invention, as well as with dual specificity to HGF and RON, and in particular to human RON (Ming-Hai Wang et al., *Acta Pharmacologica Sinica* (2010) 31: 1181-1188) are within the scope of this invention.

As further described herein, a polypeptide of the invention may contain two or more immunoglobulin single variable domains of the invention that are directed against HGF and in particular human HGF (SEQ ID NO: 1). Generally, such polypeptides will bind to HGF and in particular human HGF (SEQ ID NO: 1) with increased avidity compared to a single amino acid sequence of the invention. Such a polypeptide may for example comprise two immunoglobulin single variable domains of the invention that are directed against the same antigenic determinant, epitope, part, domain, subunit or confirmation (where applicable) of HGF and in particular human HGF (SEQ ID NO: 1) (which may or may not be an interaction site); or comprise at least one "first" amino acid sequence of the invention that is directed against a first antigenic determinant, epitope, part, domain, subunit or conformation (where applicable) of HGF and in particular human HGF (SEQ ID NO: 1) (which may or may not be an interaction site); and at least one "second" amino acid sequence of the invention that is directed against a second antigenic determinant, epitope, part, domain, subunit or conformation (where applicable) different from the first (and which again may or may not be an interaction site). Preferably, in such "biparatopic" polypeptides of the invention, at least one amino acid sequence of the invention is directed against an interaction site (as defined herein), although the invention in its broadest sense is not limited thereto. For instance, polypeptides of the invention may be formatted e.g., in a biparatopic way such as to combine monovalent building blocks directed against different epitopes as characterized in the experimental part.

Also, when the target is part of a binding pair (for example, a receptor-ligand binding pair), the immunoglobulin single variable domains and polypeptides may be such that they compete with the cognate binding partners, e.g., HGF for binding to c-Met, and/or such that they (fully or partially) neutralize binding of the binding partner to the target.

It is also expected that the immunoglobulin single variable domains and polypeptides of the invention will generally bind to all naturally occurring or synthetic analogs, variants, mutants, alleles, parts and fragments of HGF and in particular human HGF (SEQ ID NO: 1); or at least to those analogs, variants, mutants, alleles, parts and fragments of HGF and in particular human HGF (SEQ ID NO: 1) that contain one or more antigenic determinants or epitopes that are essentially the same as the antigenic determinant(s) or epitope(s) to which the immunoglobulin single variable domains and polypeptides of the invention bind to HGF and in particular to human HGF (SEQ ID NO: 1). Again, in such a case, the immunoglobulin single variable domains and polypeptides of the invention may bind to such analogs, variants, mutants, alleles, parts and fragments with an affinity and/or specificity that are the same as, or that are different from (i.e., higher than or lower than), the affinity and specificity with which the immunoglobulin single variable domains of the invention bind to (wild-type) HGF.

As HGF and in particular human HGF (SEQ ID NO: 1) exists in a monomeric form and in one or more multimeric forms, e.g. in homodimeric form, it is within the scope of the invention that the immunoglobulin single variable domains and polypeptides of the invention i) only bind to HGF and in particular human HGF (SEQ ID NO: 1) in monomeric form, ii) only bind to HGF and in particular human HGF (SEQ ID NO: 1) in multimeric/dimeric (homo- and/or heterodimeric) form, or iii) bind to both the monomeric and the multimeric form. In a preferred aspect of the invention, the polypeptides of the invention prevent formation of homodimeric human HGF complexes. In another preferred aspect of the invention, the polypeptides of the invention do not induce (even at higher concentration such as 10 nM or more, 50 nM or more, 100 nM or more, or 500 nM or more) formation of homodimeric human HGF complexes. Again, in such a case, the polypeptides of the invention may bind to the monomeric form with an affinity and/or specificity that are the same as, or that are different from (i.e., higher than or lower than), the affinity and specificity with which the immunoglobulin single variable domains of the invention bind to the multimeric form.

Also, when HGF and in particular human HGF (SEQ ID NO: 1) can associate with other proteins or polypeptides to form protein complexes (e.g., with c-Met, but also with other receptors such as EGFR, HER3, plexins, integrins, CD44, RON), it is within the scope of the invention that the immunoglobulin single variable domains and polypeptides of the invention bind to HGF and in particular human HGF (SEQ ID NO: 1) in its non-associated state (and e.g., prevent ligand binding and/or prevent signalling), bind to HGF and in particular human HGF (SEQ ID NO: 1) in its associated state, or bind to both (preferably to the non-associated state). In all these cases, the immunoglobulin single variable domains and polypeptides of the invention may bind to such associated protein complexes with an affinity and/or specificity that may be the same as or different from (i.e., higher than or lower than) the affinity and/or specificity with which the immunoglobulin single variable domains and polypeptides of the invention bind to HGF and in particular human HGF (SEQ ID NO: 1) in its non-associated state.

Also, as will be clear to the skilled person, proteins or polypeptides that contain two or more immunoglobulin single variable domains directed against HGF and in particular human HGF (SEQ ID NO: 1), e.g., "biparatopic" polypeptides of the invention, may bind with higher avidity to HGF and in particular human HGF (SEQ ID NO: 1) than the corresponding monomeric amino acid sequence(s). For example, and without limitation, proteins or polypeptides that contain two or more immunoglobulin single variable domains directed against different epitopes of HGF and in particular human HGF (SEQ ID NO: 1) may (and usually will) bind with higher avidity than each of the different monomers, and proteins or polypeptides that contain two or more immunoglobulin single variable domains directed against HGF and in particular human HGF (SEQ ID NO: 1) may (and usually will) bind also with higher avidity to a multimer (e.g., homodimer) of HGF and in particular to a multimer (e.g., homodimer) of human HGF (SEQ ID NO: 1).

Generally, immunoglobulin single variable domains and polypeptides of the invention will at least bind to those forms of HGF and in particular human HGF (SEQ ID NO: 1) (including monomeric, multimeric, associated and different conformational forms) that are the most relevant from a biological and/or therapeutic point of view, as will be clear to the skilled person.

It is also within the scope of the invention to use parts, fragments, analogs, mutants, variants, alleles and/or derivatives of the immunoglobulin single variable domains and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against HGF and in particular human HGF (SEQ ID NO: 1); and more preferably will be capable of specific binding to HGF and in particular human HGF (SEQ ID NO: 1), and even more preferably capable of binding to HGF and in particular human HGF (SEQ ID NO: 1) with an EC50 value, average Ki, $IC_{50}$ value concerning binding, migration, displacing and/or proliferation blocking and/or other measures for potency, as further described herein, (e.g., in the experimental part) that is as defined herein and such parts, fragments, analogs, mutants, variants, alleles and/or derivatives may be more potent, more stable, more soluble and may have the same epitope. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e., by linking or genetic fusion) one or more (smaller) parts or fragments as described herein.

For a general description of immunoglobulin single variable domains, reference is made to the further description below, as well as to the prior art cited herein. In this respect, it should however be noted that this description and the prior art mainly describes immunoglobulin single variable domains of the so-called "$V_H3$ class" (i.e., immunoglobulin single variable domains with a high degree of sequence homology to human germline sequences of the $V_H3$ class such as DP-47, DP-51 or DP-29), which form a preferred aspect of this invention. It should, however, be noted that the invention in its broadest sense generally covers any type of immunoglobulin single variable domains directed against HGF and in particular human HGF (SEQ ID NO: 1), and for example also covers the immunoglobulin single variable domains belonging to the so-called "$V_H4$ class" (i.e., immunoglobulin single variable domains with a high degree of sequence homology to human germline sequences of the $V_H4$ class such as DP-78), as for example described in WO 07/118670.

Generally, immunoglobulin single variable domains (in particular $V_{HH}$ sequences and sequence optimized immunoglobulin single variable domains) can in particular be characterized by the presence of one or more "Hallmark residues" (as described herein) in one or more of the framework sequences (again as further described herein).

Thus, generally, an immunoglobulin single variable domain can be defined as an amino acid sequence with the (general) structure (cf. formula 1 below)

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively.

In a preferred aspect, the invention provides polypeptides comprising at least an immunoglobulin single variable domain that is an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) at least one of the amino acid residues at positions 11, 37, 44, 45, 47, 83, 84, 103, 104 and 108 according to the Kabat numbering are chosen from the Hallmark residues mentioned in Table A-1 below; and in which:

ii) said amino acid sequence has at least 80%, more preferably 90%, even more preferably 95% amino acid identity with at least one of the immunoglobulin single variable domains as shown in WO 2009/138519 (see SEQ ID NOs: 1 to 125 in WO 2009/138519), in which for the purposes of determining the degree of amino acid identity, the amino acid residues that form the CDR sequences (indicated with X in the sequences) are disregarded; and in which:

iii) the CDR sequences are generally as further defined herein (e.g., the CDR1, CDR2 and CDR3 in a combination as provided in Table (B-2), note that the CDR definitions are calculated according to the Kabat numbering system).

TABLE A-1

Hallmark Residues in VHHs

| Position | Human $V_H3$ | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | $F^{(1)}$, Y, V, L, A, H, S, I, W, C, N, G, D, T, P, preferably $F^{(1)}$ or Y |
| 44$^{(8)}$ | G | $E^{(3)}$, $Q^{(3)}$, $G^{(2)}$, D, A, K, R, L, P, S, V, H, T, N, W, M, I; preferably $G^{(2)}$, $E^{(3)}$ or $Q^{(3)}$; most preferably $G^{(2)}$ or $Q^{(3)}$. |
| 45$^{(8)}$ | L | $L^{(2)}$, $R^{(3)}$, P, H, F, G, Q, S, E, T, Y, C, I, D, V; preferably $L^{(2)}$ or $R^{(3)}$ |
| 47$^{(8)}$ | W, Y | $F^{(1)}$, $L^{(1)}$ or $W^{(2)}$ G, I, S, A, V, M, R, Y, E, P, T, C, H, K, Q, N, D; preferably $W^{(2)}$, $L^{(1)}$ or $F^{(1)}$ |
| 83 | R or K; usually R | R, $K^{(5)}$, T, $E^{(5)}$, Q, N, S, I, V, G, M, L, A, D, Y, H; preferably K or R; most preferably K |
| 84 | A, T, D; predominantly A | $P^{(5)}$, S, H, L, A, V, I, T, F, D, R, Y, N, Q, G, E; preferably P |
| 103 | W | $W^{(4)}$, $R^{(6)}$, G, S, K, A, M, Y, L, F, T, N, V, Q, $P^{(6)}$, E, C; preferably W |
| 104 | G | G, A, S, T, D, P, N, E, C, L; preferably G |
| 108 | L, M or T; predominantly L | Q, $L^{(7)}$, R, P, E, K, S, T, M, A, H; preferably Q or $L^{(7)}$ |

Notes:
$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.
$^{(4)}$With both GLEW at positions 44-47 and KERE or KQRE at positions 43-46.
$^{(5)}$Often as KP or EP at positions 83-84 of naturally occurring $V_{HH}$ domains.
$^{(6)}$In particular, but not exclusively, in combination with GLEW at positions 44-47.
$^{(7)}$With the proviso that when positions 44-47 are GLEW, position 108 is always Q in (non-humanized) $V_{HH}$ sequences that also contain a W at 103.
$^{(8)}$The GLEW group also contains GLEW-like sequences at positions 44-47, such as for example GVEW, EPEW, GLER, DQEW, DLEW, GIEW, ELEW, GPEW, EWLP, GPER, GLER and ELEW.

Again, such immunoglobulin single variable domains may be derived in any suitable manner and from any suitable source, and may for example be naturally occurring $V_{HH}$ sequences (i.e., from a suitable species of Camelid, e.g., llama) or synthetic or semi-synthetic VHs or VLs (e.g., from human). Such immunoglobulin single variable domains may include "humanized" or otherwise "sequence optimized" VHHs, "camelized" immunoglobulin sequences (and in particular camelized heavy chain variable domain sequences, i.e., camelized VHs), as well as human VHs, human VLs, camelid VHHs that have been altered by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. As mentioned herein, a particularly preferred class of immunoglobulin single variable domains of the invention comprises immunoglobulin single variable domains with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art on humanization referred to herein. Again, it should be noted that such humanized immunoglobulin single variable domains of the invention can be obtained in any suitable manner known per se and thus are not strictly limited to polypeptides that have been obtained using a polypeptide that comprises a naturally occurring $V_{HH}$ domain as a starting material.

Another particularly preferred class of immunoglobulin single variable domains of the invention comprises immunoglobulin single variable domains with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$-$V_L$ interface, and/or at the so-called Camelidae hallmark residues, as defined herein (see also for example WO 94/04678 and Davies and Riechmann (1994 and 1996)). Preferably, the $V_H$ sequence that is used as a starting material or starting point for generating or designing the camelized immunoglobulin single variable domains is preferably a $V_H$ sequence from a mammal, more preferably the $V_H$ sequence of a human being, such as a $V_H3$ sequence. However, it should be noted that such camelized immunoglobulin single variable domains of the invention can be obtained in any suitable manner known per se and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" immunoglobulin single variable domains of the invention, respectively. This nucleic acid can then be expressed in a manner known per se, so as to provide the desired immunoglobulin single variable domains of the invention. Alternatively, based on the amino acid sequence of a naturally occurring $V_{HH}$ domain or $V_H$ domain, respectively, the amino acid sequence of the desired humanized or camelized immunoglobulin single variable domains of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized immunoglobulin single variable domains of the invention, respectively, can be designed and then synthesized de novo using techniques for nucleic acid synthesis known per se, after which the nucleic acid thus obtained can be expressed in a manner known per se, so as to provide the desired immunoglobulin single variable domains of the invention.

In a further preferred aspect, the invention provides polypeptides comprising one immunoglobulin single variable domain with amino acid sequence selected from the group consisting of amino acid sequences with SEQ ID NOs: 6 to 27, preferably SEQ ID NOs: 7, 8, 10, 15, 16, 18 and 20-25, even more preferably SEQ ID NOs: 7 and 18, (see experimental part) and one immunoglobulin single variable domain with amino acid sequence selected from the group consisting of moieties providing an increased half-life (see below).

In a further preferred aspect, the invention provides polypeptides comprising at least an immunoglobulin single variable domain with amino acid sequence selected from the group consisting of amino acid sequences that essentially consist of 4 framework regions (FR1 to FR4, respectively) and 3 complementarity determining regions (CDR1 to CDR3, respectively), in which the CDR sequences of said amino acid sequences have at least 70% amino acid identity, preferably at least 80% amino acid identity, more preferably at least 90% amino acid identity, such as 95% amino acid identity or more or even essentially 100% amino acid identity with the CDR sequences (see Table B-2) of at least one of the immunoglobulin single variable domains of SEQ ID NOs: 6 to 27, preferably SEQ ID NOs: 7, 8, 10, 15, 16, 18 and 20-25, even more preferably SEQ ID NOs: 7 and 18 (see experimental part). This degree of amino acid identity can for example be determined by determining the degree of amino acid identity (in a manner described herein) between said amino acid sequence and one or more of the sequences of SEQ ID NOs: 6 to 27, preferably SEQ ID NOs: 7, 8, 10, 15, 16, 18 and 20-25, even more preferably SEQ ID NOs: 7 and 18 (see experimental part), in which the amino acid residues that form the framework regions are disregarded. Such polypeptides and/or immunoglobulin single variable domains of the invention may further provide the following:

(i) polypeptides comprising at least one (preferably one) immunoglobulin single variable domain that is directed against (as defined herein) HGF and in particular human HGF (SEQ ID NO: 1) and that has at least 80%, preferably at least 85%, such as 90% or 95% or more sequence identity with at least one of the immunoglobulin single variable domains of SEQ ID NOs: 6 to 27, preferably SEQ ID NOs: 7, 8, 10, 15, 16, 18 and 20-25, even more preferably SEQ ID NOs: 7 and 18 (see experimental part); and/or (ii) polypeptides comprising at least one (preferably one) immunoglobulin single variable domain that is directed against (as defined herein) HGF and in particular human HGF (SEQ ID NO: 1) and that cross-block (as defined herein) the binding of at least one of the immunoglobulin single variable domains of SEQ ID NOs: 6 to 27, preferably SEQ ID NOs: 7, 8, 10, 15, 16, 18 and 20-25, even more preferably SEQ ID NOs: 7 and 18 (see experimental part) to HGF and in particular human HGF (SEQ ID NO: 1) and/or that compete with at least one of the immunoglobulin single variable domains of SEQ ID NOs: 6 to 27, preferably SEQ ID NOs: 7, 8, 10, 15, 16, 18 and 20-25, even more preferably SEQ ID NOs: 7 and 18 (see experimental part) for binding to HGF and in particular human HGF (SEQ ID NO: 1), and of which immunoglobulin single variable domains may be as further described herein; and/or (iii) polypeptides of the invention that comprise one or more (preferably one) of such immunoglobulin single variable domains (which may be as further described herein, and may for example be bispecific (e.g. also bind to serum albumin) and/or biparatopic polypeptides as described herein), and nucleic acid sequences that encode such immunoglobulin single variable domains and polypeptides. Such immunoglobulin single variable domains and polypeptides do not include any naturally occurring ligands.

The polypeptides of the invention comprise or essentially consist of at least one immunoglobulin single variable domain of the invention. Some preferred, but non-limiting examples of immunoglobulin single variable domains of the invention are given in SEQ ID NOs: 6 to 27, preferably SEQ ID NOs: 7, 8, 10, 15, 16, 18 and 20-25, even more preferably SEQ ID NOs: 7 and 18 (see experimental part).

EGFR consists of an extracellular ligand-binding domain, a transmembrane domain and an intracellular tyrosine kinase domain (Yarden et al. 2001, Nature Rev. Mol. Cell Biol. 2:127-137). Aberrant activation of EGFR mediated signalling has been implicated in processes involved in tumor growth and progression, including tumor cell proliferation, angiogenesis, metastasis, inhibition of apoptosis and resistance to radio- or chemotherapy (Grünwald, Hidalgo 2003 J. Natl. Cancer Inst. 95:851-867; and references therein). EGFR is expressed in a wide variety of tumors of epithelial origin, including >40% of NSCLC (non-small-cell-lung cancer), >95% of head and neck cancer, >30% of pancreatic cancer, >90% of renal carcinoma, >35% of ovarian cancer, >40% of glioma and >31% of bladder cancer (Salomon et al. 1995. Crit. Review Oncol. Hematol, 19:183-232). Since high levels of EGFR expression are correlated to disease progression, increased metastasis and poor prognosis, this provides a strong rationale for developing effective EGFR targeting antibodies for the treatment of various solid tumors.

Identification of mAbs inhibiting EGFR is an approach used in clinical development to target aberrant signalling of EGFR in malignant neoplasia. Examples of such EGFR targeting antibodies are IMC-C225 (Erbitux, Imclone), EMD72000 (Merck Darmstadt), ABX-EGF (Abgenix), h-R3 (theraCIM, YM Biosciences) and Humax-EGFR (Genmab). The mechanism of action of these antibodies relies on the inhibition with ligand binding to the receptor and subsequent inhibition of receptor transphosphorylation and the downstream signaling cascade. Mab 225 (of which Erbitux is the chimeric derivative), the 225-derived F(ab')$_2$ fragment are able to induce EGFR internalization and modest receptor sequestration but only after sustained incubation with EGFR expressing cells. The monovalent 225-derived Fab' fragment however only induces receptor downregulation after preincubation with a rabbit anti-mouse antibody (Fan et al., 1993 J. Biol. Chem. 268:21073-21079; Fan et al., 1994 J. Biol. Chem. 269:27595-27602). These antibodies show an antitumoral activity against a broad panel of human tumor xenografts (reviewed in Grünwald & Hidalgo 2003 J. Natl. Cancer Inst. 95:851-867).

However, the known antibody-based therapeutics binding to the EGF receptor are cytostatic instead of cytotoxic. Indeed none of these antibodies or the presently available small molecule drugs is completely effective for the treatment of cancer. Moreover, for some patients therapeutic application of EGFR inhibitors is limited by serious toxicity.

WO 05/044858, WO 04/041867 and WO07/042289 already describe anti-EGFR Nanobodies and polypeptides with improved properties over standard antibodies. What is more, biodistribution of αEGFR-αEGFR-αAlb (50 kDa) was comparable to cetuximab (150 kDa), while it showed faster and deeper tumor penetration. The latter indicates that Nanobodies might have distinguished potential in comparison to conventional mAbs for use in cancer treatment.

In addition, multispecific constructs comprising the polypeptides of the present invention have improved efficacy in modulating signalling over a combination of the individual polypeptides of the present invention. In particular, a multispecific construct comprising (a) one or more polypeptides modulating HGF-mediated signalling as described herein, and (b) one or more polypeptides modulating EGFR-mediated signalling is exceptionally useful in the diagnosis, prevention and treatment of diseases and disorders as set out above. The multispecific construct is particular useful in the diagnosis, prevention and treatment of cancer, in particular of non-small cell lung cancer.

The polypeptides and Nanobodies described in WO 05/044858, WO 04/041867, and/or WO07/042289 are particularly preferred as polypeptides modulating EGFR-mediated signalling in the multispecific constructs of the present invention. Accordingly, the present invention relates to a multispecific, such as, for instance, a bispecific or trispecific (or even tetraspecific), construct comprising at least one ISVD against EGFR and at least one ISVD against HGF, and optionally against VEGF. In such a multispecific, e.g. bispecific or trispecific (or even tetraspecific), polypeptide construct, the Nanobodies and polypeptides against HGF described herein can be combined with one or more of the anti-EGFR Nanobodies and polypeptides described in WO 05/044858, WO 04/041867, and WO07/042289 (all of which are specifically incorporated in its entirety herein).

Hence, the present invention relates to a multispecific construct of (a) one or more polypeptides modulating HGF-mediated signalling and (b) one or more polypeptides modulating EGFR-mediated signalling, in particular EGFR-mediated signalling (c) and possibly Alb-Nanobodies, for use in the diagnosis, prevention and treatment of diseases and disorders as set out above, in particular non-small cell lung cancer.

Development of a vascular system is a fundamental requirement for many physiological and pathological processes. It is now well established that angiogenesis is implicated in the pathogenesis of a variety of disorders, including solid tumors and metastasis. In the case of tumor growth, angiogenesis appears to be crucial for the transition from hyperplasia to neoplasia, and for providing nourishment for the growth and metastasis of the tumor. Folkman et al., Nature 339:58 (1989). The process of vascular development is tightly regulated, in which vascular endothelial growth factor (VEGF) has been identified as the key factor involved in stimulating angiogenesis and in inducing vascular permeability. Ferrara et al., Endocr. Rev. 18:4-25 (1997). The term "VEGF" or "VEGF-A" is used to refer to the 165-amino acid human vascular endothelial cell growth factor and related 121-, 189-, and 206-amino acid human vascular endothelial cell growth factors, as described by Leung et al. Science, 246:1306 (1989), and Houck et al. Mol. Endocrin., 5:1806 (1991), together with the naturally occurring allelic and processed forms thereof. "VEGF biological activity" includes binding to any VEGF receptor or any VEGF signaling activity such as regulation of both normal and abnormal angiogenesis and vasculogenesis (Ferrara and Davis-Smyth (1997) Endocrine Rev. 18:4-25; Ferrara (1999) J. Mol. Med. 77:527-543).

Most clinical experience has been obtained with A4.6.1, also called bevacizumab (Avastin®; Genentech, San Francisco, Calif.). Avastin in combination with chemotherapy is, however, plagued by side-effects (hemorrhages, arterial thromboembolism, hypertension, gastrointestinal (GI) perforations, wound healing problems, proteinuria and congestive heart failure) which are primarily due to the fact that the anti-VEGF activity is not restricted to the site of the tumor, but persists in circulation over a long period of time. This results in a shift of physiological to pathophysiological activity of the peripheral endothelial cells. Anti-VEGF strategies using a recombinant humanized anti-VEGF Fab (rhuFab VEGF, Ranibizumab or Lucentis™) for the treatment of a chronic disease is, however, not ideal because of the risk of endophthalmitis, vitreous hemorrhage, and retinal detachment.

WO 08/101985 already describes anti-VEGF Nanobodies and polypeptides with improved properties over standard antibodies.

However, the multispecific constructs comprising the polypeptides of the present invention have improved efficacy in modulating signalling over a combination of the individual polypeptides of the present invention. In particular, a multispecific construct comprising (a) one or more polypeptides modulating HGF signalling as described herein, and (b) one or more polypeptides modulating VEGF-mediated signalling, and optionally EGFR-mediated signalling and possibly Alb-polypeptides, is exceptionally useful in the diagnosis, prevention and treatment of diseases and disorders as set out above. The multispecific construct is particular useful in the diagnosis, prevention and treatment of cancer, in particular of non-small cell lung cancer.

The polypeptides and Nanobodies described in WO 08/101985 are particularly preferred as polypeptides modulating VEGF-mediated signalling in the multispecific constructs of the present invention. Accordingly, the present invention relates to a multispecific, such as for instance a bispecific, trispecific, or tetraspecific construct comprising at least one ISVD against HGF and at least one ISVD against VEGF, and optionally against EGFR. In such a multispecific, e.g. bispecific, trispecific or tetraspecific, polypeptide construct, the Nanobodies and polypeptides against HGF described herein can be combined with one or more of the anti-VEGF Nanobodies and polypeptides described in WO 08/101985 (which is specifically incorporated in its entirety herein).

Hence, the present invention relates to a multispecific construct of (a) one or more polypeptides modulating HGF-mediated signalling and (b) one or more polypeptides modulating VEGF-mediated signalling, in particular human VEGF-mediated signalling, and optionally (c) one or more polypeptides modulating EGFR-mediated signalling, in particular human EGFR-mediated signalling, for use in the diagnosis, prevention and treatment of diseases and disorders as set out above, in particular non-small cell lung cancer. In particular aspects, the present invention provides combination therapies for treating a pathological condition, such as cancer, wherein a HGF antagonist is combined with a VEGF antagonist, or wherein a HGF antagonist is combined with a VEGF antagonist and an EGFR antagonist, thereby providing significant anti-tumor activity.

Generally, proteins or polypeptides that comprise or essentially consist of a single immunoglobulin single variable domain will be referred to herein as "monovalent" proteins or polypeptides or as "monovalent constructs". Proteins and polypeptides that comprise or essentially consist of two or more immunoglobulin single variable domains (such as at least two immunoglobulin single variable domains of the invention or at least one immunoglobulin single variable domain of the invention and at least one other immunoglobulin single variable domain) will be referred to herein as "multivalent" proteins or polypeptides or as "multivalent constructs", and these may provide certain advantages compared to the corresponding monovalent immunoglobulin single variable domains of the invention. Some non-limiting examples of such multivalent constructs will become clear from the further description herein.

For example a "bivalent" polypeptide of the invention comprises two ISVDs, optionally linked via a linker sequence, whereas a "trivalent" polypeptide of the invention comprises three ISVDs, optionally linked via two linker sequences, whereas a "tetravalent" polypeptide of the invention comprises four ISVDs, optionally linked via three linker sequences; etc.; in which at least one of the ISVDs present in the polypeptide or construct, and up to all of the ISVDs present in the polypeptide or construct, is/are an ISVD(s).

In a multivalent polypeptide of the invention the two or more ISVDs may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical ISVDs; (b) a first ISVD directed against a first antigenic determinant of a protein or antigen and a second ISVD directed against the same antigenic determinant of said protein or antigen which is different from the first ISVD; (c) a first ISVD directed against a first antigenic determinant of a protein or antigen and a second ISVD directed against another antigenic determinant of said protein or antigen; or (d) a first ISVD directed against a first protein or antigen and a second ISVD directed against a second protein or antigen (i.e., different from said first antigen). Similarly, a trivalent polypeptide of the invention may, for example and without being limited thereto, comprise (a) three identical ISVDs; (b) two identical ISVDs against a first antigenic determinant of an antigen and a third ISVD directed against a different antigenic determinant of the same antigen; (c) two identical ISVDs against a first antigenic determinant of an antigen and a third ISVD directed against a second antigen different from said first antigen; (d) a first ISVD directed against a first antigenic determinant of a first antigen, a second ISVD directed against a second antigenic determinant of said first antigen and a third ISVD directed against a second antigen different from said first antigen; or (e) a first ISVD directed against a first antigen, a second ISVD directed against a second antigen different from said first antigen, and a third ISVD directed against a third antigen different from said first and second antigen. Similarly, a tetravalent polypeptide of the invention may, for example and without being limited thereto, comprise (a) four identical ISVDs; (b) three identical ISVDs against a first antigenic determinant of a first antigen and one ISVD directed against a different antigenic determinant of the same antigen; (c) three identical ISVDs against a first antigenic determinant of a first antigen and one ISVD directed against a second antigen, different from said first antigen; (d) two identical ISVDs against a first antigenic determinant of an antigen and two ISVDs directed against a different antigenic determinant of the same antigen; (e) two identical ISVDs against a first antigenic determinant of an antigen, one ISVD directed against a different antigenic determinant of the same antigen, and one ISVDs directed against a second antigen different from said first antigen; (f) two identical ISVDs against a first antigenic determinant of an antigen, two ISVDs directed against a second antigen, wherein said second antigen is different from said first antigen; (g) two identical ISVDs against a first antigenic determinant of an antigen, one ISVD directed against a second antigen, wherein said second antigen is different from said first antigen, and one ISVD directed against a third antigen, wherein said third antigen is different from said first and second antigen; (h) a first ISVD directed against a first antigenic determinant of a first antigen, a second ISVD directed against a second antigenic determinant of said first antigen, a third and a fourth ISVD directed against a second antigen different from said first antigen; (i) a first ISVD directed against a first antigenic determinant of a first antigen, a second ISVD directed against a second antigenic determinant of said first antigen, a third ISVD directed against a second antigen different from said first antigen and a fourth ISVD directed against a third antigen different from said first antigen and said second antigen; or (j) a first ISVD directed against a first antigen, a second ISVD directed against a second antigen different from said first antigen, a third ISVD directed against a third antigen different from said first and second antigen, and a fourth ISVD directed against a fourth antigen different from said first, said second and said third antigen.

Polypeptides of the invention that contain at least two ISVDs, in which at least one ISVD is directed against a first antigen (i.e., against HGF) and at least one ISVD is directed against a second antigen (i.e., different from HGF, e.g. EGFR or VEGF), will also be referred to as "multispecific" polypeptides of the invention, and the ISVDs present in such polypeptides will also be referred to herein as being in a "multivalent format". Thus, for example, a "bispecific" polypeptide of the invention is a polypeptide that comprises at least one ISVD directed against a first antigen (i.e. HGF) and at least one further ISVD directed against a second antigen (i.e., different from HGF, such as, for instance, EGFR or VEGF), whereas a "trispecific" polypeptide of the invention is a polypeptide that comprises at least one ISVD directed against a first antigen (i.e., HGF), at least one further ISVD directed against a second antigen (i.e., different from HGF, such as for instance EGFR or VEGF) and at least one further ISVD directed against a third antigen (i.e., different from both HGF and the second antigen, e.g., EGFR or VEGF), whereas a "tetraspecific" polypeptide of the invention is a polypeptide that comprises at least one ISVD directed against a first antigen (i.e., HGF), at least one further ISVD directed against a second antigen (i.e., different from HGF, such as, for instance EGFR), at least one further ISVD directed against a third antigen (i.e., different from both HGF and the second antigen EGFR, such as for instance VEGF), at least one further ISVD directed against a fourth antigen (i.e., different from the antigens HGF, EGFR as well as VEGF, such as, for instance, serum albumin); etc.

Accordingly, in its simplest form, a bispecific polypeptide of the invention is a bivalent polypeptide of the invention (as defined herein), comprising a first ISVD directed against HGF, and a second ISVD directed against a second antigen, such as EGFR or VEGF, in which said first and second ISVD may optionally be linked via a linker sequence (as defined herein); whereas a trispecific polypeptide of the invention in its simplest form is a trivalent polypeptide of the invention (as defined herein), comprising a first ISVD directed against HGF, a second ISVD directed against a second antigen, such as, for instance, EGFR or VEGF, and a third ISVD directed against a third antigen, e.g., different form HGF and said second antigen (e.g., EGFR or VEGF), in which said first, second and third ISVDs may optionally be linked via one or more, and in particular one and more in particular two, linker sequences; whereas a tetraspecific polypeptide of the invention in its simplest form is a tetravalent polypeptide of the invention (as defined herein), comprising a first ISVD directed against HGF, a second ISVD directed against a second antigen, such as, for instance, EGFR, a third ISVD directed against a third antigen, such as VEGF, and a fourth ISVD directed against a fourth antigen different from HGF, EGFR and VEGF, in which said first, second, third and fourth ISVDs may optionally be linked via one or more, and in particular one or more in particular three, linker sequences.

However, as will be clear from the description, the invention is not limited thereto, in the sense that a multi-specific polypeptide of the invention may comprise at least one ISVD against HGF and any number of ISVDs directed against one or more antigens different from HGF, respectively.

According to a specific, but non-limiting embodiment, a polypeptide as described herein comprises at least one ISVD against HGF and at least one ISVD against EGFR and/or VEGF, optionally linked using one or more suitable linkers. In such a bispecific polypeptide construct, the Nanobodies and polypeptides against HGF described herein can be combined with one or more of the anti-EGFR Nanobodies and polypeptides described in WO 05/044858, WO 04/041867 and/or WO07/042289, and/or with one or more of the anti-VEGF Nanobodies and polypeptides described in WO08/101985.

Bispecific polypeptides that comprise two binding moieties, such as for instance two ISVDs, wherein each binding moiety is specific for a tumor associated antigen (i.e., an antigen expressed on a tumor cell, also called 'tumor marker'), are highly advantageous in tumor targeting. Such bispecific polypeptides are capable of simultaneously targeting two tumor associated antigens, resulting in enhanced tumor specificity. It is known that most tumor markers are not truly tumor specific but also occur (mostly at lower levels) on normal tissues or cells. Monospecific binding moieties, ISVDs or polypeptides against only one tumor marker will therefore also recognize those normal tissues or cells resulting in a non-specific cell arrest or killing. Polypeptides that are specific for two or more markers on one or more tumor cells will be much more tumor specific and provide a better specific binding. They can thus block simultaneously multiple receptor activation and downstream signal transduction pathways, and provide a better inhibition of tumor proliferation and arrest or killing of the tumor cells.

Accordingly, the present invention also relates to a bispecific or multispecific polypeptide, comprising or essentially consisting of at least two binding moieties, such as two ISVDs, wherein at least one of said at least two binding moieties is directed against HGF, and the other binding moiety is directed against EGFR or VEGF. In a particular embodiment, said at least two binding moieties have a moderate or low affinity to their individual tumor associated antigen (such as, for instance, HGF and EGFR or VEGF) and, accordingly, have only a reduced retention on normal tissues or cells expressing one of the tumor associated antigens. Those at least two binding moieties, however preferentially target (have a high avidity for) tumor cells that express both antigens (such as, for instance, HGF and EGFR or VEGF) recognized by the bispecific or multispecific polypeptide.

Accordingly, the present invention also relates to a trispecific or multispecific polypeptide, comprising or essentially consisting of at least three binding moieties, such as three ISVDs, wherein at least one of said at least three binding moieties is directed against HGF, one binding moiety is directed against EGFR and one binding moiety is directed against VEGF. In a particular embodiment, two of said at least three binding moieties have a moderate or low affinity to their individual tumor associated antigen (such as, for instance, HGF and EGFR) and, accordingly, have only a reduced retention on normal tissues or cells expressing one of the tumor associated antigens. Those at least two binding moieties, however preferentially target (have a high avidity for) tumor cells that express both antigens (such as, for instance, HGF and EGFR) recognized by the bispecific, trispecific or multispecific polypeptide.

EGFR, for example, is over-expressed on tumors in breast cancer, colon cancer, ovarian cancer, lung cancer and head and neck cancer.

By simultaneous targeting two of these tumor associated antigens, or different epitopes on one of these tumor associated antigens, a much more selective and/or enhanced tumor targeting is obtained.

Therefore, in a preferred embodiment, the invention also provides a bispecific or trispecific polypeptide comprising or essentially consisting of a Nanobody directed against HGF and a Nanobody directed against EGFR and optionally against VEGF. The polypeptide of the invention may comprise or essentially consist of a Nanobody directed against HGF and a Nanobody directed against EGFR. The polypeptide of the invention may comprise or essentially consist of a Nanobody directed against HGF and a Nanobody directed against VEGF. Also, the polypeptide of the invention may comprise or essentially consist of a Nanobody directed against HGF, a Nanobody directed against EGFR and a Nanobody directed against VEGF.

Also encompassed within the scope of the present invention are bispecific or multispecific polypeptides comprising or essentially consisting of at least two Nanobodies of which one of said at least two Nanobodies has a decreased or increased affinity for its antigen, upon binding by the other Nanobodies to its antigen. Such binding is called 'conditional bispecific or multispecific binding'. Such bispecific or multispecific polypeptide is also called 'a conditionally binding bispecific or multispecific polypeptide of the invention'.

Binding of the antigen by the first of said at least two Nanobodies may modulate, such as enhance, reduce or inhibit, binding of the antigen by the second of said at least two Nanobodies. In an embodiment, binding by the first of said at least two Nanobodies stimulates binding by the second of said at least two Nanobodies. In another embodiment, binding by the first of said at least two Nanobodies at least partially inhibits binding by the second of said at least two Nanobodies. In such an embodiment, the polypeptide of the invention may, for example, be maintained in the body of a subject organism in vivo through binding to a protein which increases the half-life of the polypeptide until such a time as it becomes bound to its second target antigen and dissociates from the half-life increasing protein.

Modulation of binding in the above context is achieved as a consequence of the structural proximity of the antigen binding sites of the Nanobodies relative to one another. Such structural proximity can be achieved by the nature of the structural components linking the two or more antigen binding sites, e.g., by the provision of a linker with a relatively rigid structure that holds the antigen binding sites in close proximity. Advantageously, the two or more antigen binding sites are in physically close proximity to one another such that one site modulates the binding of the antigen at another site by a process which involves steric hindrance and/or conformational changes within the polypeptide.

In another aspect, the invention relates to a compound or construct, and in particular to a protein or polypeptide (also referred to herein as a "compound of the invention" or "polypeptide of the invention", respectively) that comprises or essentially consists of one or more (preferably one) immunoglobulin single variable domains directed to human HGF (or suitable fragments thereof), and optionally further comprises one or more other groups, residues, moieties or binding units. As will become clear to the skilled person from the further disclosure herein, such further groups, residues, moieties, binding units or immunoglobulin single variable domains may or may not provide further functionality to the amino acid sequence of the invention (and/or to the compound or construct in which it is present) and may or may not modify the properties of the amino acid sequence of the invention.

As will be clear from the further description above and herein, this means that the immunoglobulin single variable domains of the invention can be used as "building blocks" to form polypeptides of the invention, i.e., by suitably combining them with other groups, residues, moieties or binding units, in order to form compounds or constructs as described herein (such as, without limitations, the biparatopic, triparatopic, tetraparatopic, bi/tri/tetra/multivalent and bi/tri/tetra/multispecific polypeptides of the invention described herein) which combine within one molecule one or more desired properties or biological functions.

The compounds or polypeptides of the invention can generally be prepared by a method which comprises at least one step of suitably linking the one or more immunoglobulin single variable domains of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted immunoglobulin single variable domains form a further aspect of the invention.

For example, such further groups, residues, moieties or binding units may be one or more additional immunoglobulin single variable domains, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, immunoglobulin single variable domains that are suitable for use as a domain antibody, single domain antibodies, immunoglobulin single variable domains (ISVDs) that are suitable for use as a single domain antibody, "dAb"'s, immunoglobulin single variable domains that are suitable for use as a dAb, or Nanobodies. Alternatively, such groups, residues, moieties or binding units may for example be chemical groups, residues, moieties, which may or may not by themselves be biologically and/or pharmacologically active. For example, and without limitation, such groups may be linked to the one or more immunoglobulin single variable domains of the invention so as to provide a "derivative" of an amino acid sequence or polypeptide of the invention, as further described herein.

Also within the scope of the present invention are compounds or constructs, which comprise or essentially consist of one or more derivatives as described herein, and optionally further comprise one or more other groups, residues, moieties or binding units, optionally linked via one or more linkers. Preferably, said one or more other groups, residues, moieties or binding units are immunoglobulin single variable domains. In the compounds or constructs described above, the one or more immunoglobulin single variable domains of the invention and the one or more groups, residues, moieties or binding units may be linked directly to each other and/or via one or more suitable linkers or spacers. For example, when the one or more groups, residues, moieties or binding units are immunoglobulin single variable domains, the linkers may also be immunoglobulin single variable domains, so that the resulting compound or construct is a fusion protein or fusion polypeptide.

In a specific, but non-limiting aspect of the invention, which will be further described herein, the polypeptides of the invention have an increased half-life in serum (as further described herein) compared to the immunoglobulin single variable domain from which they have been derived. For example, an immunoglobulin single variable domain of the invention may be linked (chemically or otherwise) to one or more groups or moieties that extend the half-life (such as PEG), so as to provide a derivative of an amino acid sequence of the invention with increased half-life.

In a specific aspect of the invention, a compound of the invention or a polypeptide of the invention may have an increased half-life, compared to the corresponding amino acid sequence of the invention. Some preferred, but non-limiting examples of such compounds and polypeptides will become clear to the skilled person based on the further disclosure herein, and for example comprise immunoglobulin single variable domains or polypeptides of the invention that have been chemically modified to increase the half-life thereof (for example, by means of pegylation); immunoglobulin single variable domains of the invention that comprise at least one additional binding site for binding to a serum protein (such as serum albumin); or polypeptides of the invention which comprise at least one amino acid sequence of the invention that is linked to at least one moiety (and in particular at least one amino acid sequence) which increases the half-life of the amino acid sequence of the invention. Examples of polypeptides of the invention which comprise such half-life extending moieties or immunoglobulin single variable domains will become clear to the skilled person based on the further disclosure herein; and for example include, without limitation, polypeptides in which the one or more immunoglobulin single variable domains of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, immunoglobulin single variable domains that are suitable for use as a single domain antibody, "dAb"'s, immunoglobulin single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more immunoglobulin single variable domains of the invention are suitable linked to one or more small proteins or peptides that can bind to serum proteins, such as, without limitation, the proteins and peptides described in WO 91/01743, WO 01/45746, WO 02/076489, WO2008/068280, WO2009/127691 and PCT/EP2011/051559.

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or polypeptides of the invention have a serum half-life e.g. in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a particular preferred but non-limiting aspect of the invention, the invention provides a polypeptide of the invention comprising i) one HGF binding immunoglobulin single variable domain as described herein; and ii) one or more (preferably one) serum albumin binding immunoglobulin single variable domain as described herein.

In a further preferred aspect, the invention provides a polypeptide of the invention comprising i) one HGF binding immunoglobulin single variable domain as described herein; and ii) one or more (preferably one) serum albumin binding immunoglobulin single variable domain of SEQ ID NO: 114 or 115 (Table B-1).

In a further preferred aspect, the invention provides a polypeptide of the invention comprising i) one HGF binding immunoglobulin single variable domain as described herein; and ii) one or more (preferably one) serum albumin binding immunoglobulin single variable domain with CDRs (defined according to the Kabat numbering) of SEQ ID NO: 114 or 115 (Table B-1). Preferably, the invention relates to a serum albumin (SA) binding immunoglobulin single variable domain, which consists of 4 framework regions (FR1 to FR4, respectively) and 3 complementarity determining regions (CDR1 to CDR3 respectively), wherein said CDR1 is SFGMS (SEQ ID NO: 128), said CDR2 is SISGSGSDT-LYADSVKG (SEQ ID NO: 129), and said CDR3 is GGSLSR (SEQ ID NO: 130).

Thus, for example, further reference (and thus incorporated by reference) is made in particular to the experimental part and further description of WO2008/068280, wherein further details on SEQ ID NO: 114 or 115 is made and e.g., the half-life of a immunoglobulin single variable domain construct containing said sequence in rhesus monkeys is disclosed.

These may comprise of two immunoglobulin single variable domains, such as one immunoglobulin single variable domain directed against HGF and one immunoglobulin single variable domain against serum albumin. Such multispecific constructs will be clear to the skilled person based on the disclosure herein; some preferred, but non-limiting examples of such multispecific immunoglobulin single variable domains are the constructs of SEQ ID NOs: 112 or 113 (see experimental part).

According to another specific, but non-limiting aspect, a polypeptide of the invention comprises or essentially consists of at least one immunoglobulin single variable domain of the invention and at least one other binding unit (i.e., directed against another epitope, antigen, target, protein or polypeptide), which is preferably also an immunoglobulin single variable domain. Such proteins or polypeptides are also referred to herein as "multispecific" proteins or polypeptides or as "multispecific constructs", and these may comprise or consist essentially of two immunoglobulin single variable domains, such as one immunoglobulin single variable domain of the invention directed against HGF and one immunoglobulin single variable domain against serum albumin. Such multispecific constructs will be clear to the skilled person based on the disclosure herein; some preferred, but non-limiting examples of such multispecific immunoglobulin single variable domains are the constructs of SEQ ID NOs: 112 or 113 (see experimental part).

According to yet another specific, but non-limiting aspect, a polypeptide of the invention comprises or essentially consists of at least one immunoglobulin single variable domain of the invention, optionally one or more further immunoglobulin single variable domains, and at least one other amino acid sequence (such as a protein or polypeptide) that confers at least one desired property to the immunoglobulin single variable domain of the invention and/or to the resulting fusion protein. Again, such fusion proteins may provide certain advantages compared to the corresponding monovalent immunoglobulin single variable domains of the invention such as e.g., may provide an increased half-life.

In the above constructs, the one or more immunoglobulin single variable domains and/or other immunoglobulin single variable domains may be directly linked to each other and/or suitably linked to each other via one or more linker sequences. Some suitable but non-limiting examples of such linkers will become clear from the further description herein.

In one embodiment, the linker sequence joining the immunoglobulin single variable domains are described in Table B-5, e.g. SEQ ID NOs: 117 to 126, or as known in the art.

In another preferred embodiment, the invention relates to a trispecific, or multispecific polypeptide, comprising or essentially consisting of at least three ISVDs, wherein two of said at least three ISVDs are directed against a tumor associated antigen (such as, for instance, HGF and EGFR or VEGF) and the other binding moiety is directed against another target or antigen. Preferably this target or antigen is a molecule which can increase the half-life of the polypeptide in vivo (as further described) or a molecule with an effector function such as CD3, the Fc receptor or a complement protein.

In an embodiment, the invention provides trispecific polypeptides comprising or essentially consisting of a Nanobody against EGFR or a Nanobody against VEGF, a Nanobody against HGF and a Nanobody against human serum albumin.

In another preferred embodiment, the invention relates to a tetraspecific, or multispecific polypeptide, comprising or essentially consisting of at least four ISVDs, wherein three of said at least four ISVDs are directed against a tumor associated antigen (such as, for instance, HGF, EGFR and VEGF) and the other binding moiety is directed against another target or antigen. Preferably this target or antigen is a molecule which can increase the half-life of the polypeptide in vivo (as further described) or a molecule with an effector function such as CD3, the Fc receptor or a complement protein.

In an embodiment, the invention provides tetraspecific polypeptides comprising or essentially consisting of a Nanobody against EGFR, a Nanobody against VEGF, a Nanobody against HGF and a Nanobody against human serum albumin.

Furthermore, although it is encompassed within the scope of the invention that the specific order or arrangement of the various Nanobodies in the polypeptides of the invention may have some influence on the properties of the final polypeptide of the invention (including but not limited to the affinity, specificity or avidity for VEGF, EGFR or HGF, respectively, or against the one or more other antigens), said order or arrangement is usually not critical and may be suitably chosen by the skilled person, optionally after some limited routine experiments based on the disclosure herein. Thus, when reference is made to a specific multispecific polypeptide of the invention, it should be noted that this encompasses any order or arrangements of the relevant Nanobodies, unless explicitly indicated otherwise.

According to yet another specific, but non-limiting aspect, a polypeptide of the invention may for example be chosen from the group consisting of immunoglobulin single variable domains that have more than 80%, preferably more than 90%, more preferably more than 95%, such as 99% or more "sequence identity" (as defined herein) with one or more of the immunoglobulin single variable domains of SEQ ID NOs: 112 or 113 (see experimental part), in which the polypeptides are preferably as further defined herein, i.e., in the preferred format of one immunoglobulin single variable domain directed against HGF and one immunoglobulin single variable domain directed against serum albumin.

According to yet another specific, but non-limiting aspect, a polypeptide of the invention may for example be chosen from the group consisting of polypeptides that have more than 80%, preferably more than 90%, more preferably more than 95%, such as 99% or more "sequence identity" (as defined herein) with one or more of the polypeptides of SEQ ID NOs: 6 to 27, preferably SEQ ID NOs: 7, 8, 10, 15, 16, 18 and 20-25, even more preferably SEQ ID NOs: 7 and 18.

Generally, for pharmaceutical use, the polypeptides of the invention may be formulated as a pharmaceutical preparation or composition comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc., wherein the parenteral administration is preferred. Such suitable administration forms—which may be solid, semi-solid or liquid, depending on the manner of administration—as well as Methods and carriers for use in the preparation thereof, will be clear to the skilled person, and are further described herein. Such a pharmaceutical preparation or composition will generally be referred to herein as a "pharmaceutical composition". A pharmaceutical preparation or composition for use in a non-human organism will generally be referred to herein as a "veterinary composition".

Thus, in a further aspect, the invention relates to a pharmaceutical composition that contains at least one amino acid of the invention, at least one polypeptide of the invention or at least one polypeptide of the invention and at least one suitable carrier, diluent or excipient (i.e., suitable for pharmaceutical use), and optionally one or more further active substances.

Generally, the polypeptides of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

The polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (e.g. intravenous, intraperitoneal, subcutaneous, intramuscular, intraluminal, intra-arterial or intrathecal administration) or for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. In one embodiment, the preparation is an aqueous solution or suspension.

The polypeptides of the invention can be administered using methods of delivery known from gene therapy, see, e.g., U.S. Pat. No. 5,399,346, which is incorporated by reference for its gene therapy delivery methods. Using a gene therapy Method of delivery, primary cells transfected with the gene encoding an amino acid sequence, polypeptide of the invention can additionally be transfected with tissue specific promoters to target specific organs, tissue, grafts, tumors, or cells and can additionally be transfected with signal and stabilization sequences for subcellularly localized expression.

Thus, the polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the polypeptide of the invention. Their percentage in the compositions and preparations may, of course, be varied and may conveniently be between about 2 to about 60% of the weight of a given unit dosage form. The amount of the polypeptide of the invention in such therapeutically useful compositions is such that an effective dosage level will be obtained.

For local administration at the site of tumor resection, the polypeptides of the invention may be used in biodegradable polymeric drug delivery systems, slow release poly(lactic-co-glycolic acid) formulations and the like (Hart et al., Cochrane Database Syst Rev. 2008 Jul. 16; (3): CD007294).

In a further preferred aspect of the invention, the polypeptides of the invention, such as a polypeptide consisting essentially of one monovalent anti-human HGF immunoglobulin single variable domain and of one monovalent anti-human serum albumin immunoglobulin single variable domain linked by a GS linker, may have a beneficial distribution and kinetics profile in solid tumors compared to conventional antibodies, such as, e.g. IgG.

The tablets, troches, pills, capsules, and the like may also contain binders, excipients, disintegrating agents, lubricants and sweetening or flavoring agents, for example those mentioned on pages 143-144 of WO 08/020079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides of the invention, sucrose or fructose as a sweetening agent, methyl- and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The polypeptides of the invention may also be administered intravenously or intraperitoneally by infusion or injection. Particular examples are as further described on pages 144 and 145 of WO 08/020079 or in PCT/EP2010/062975 (entire document).

For topical administration, the polypeptides of the invention may be applied in pure form, i.e., when they are liquids. However, it will generally be desirable to administer them to the skin as compositions or formulations, in combination with a dermatologic acceptable carrier, which may be a solid or a liquid. Particular examples are as further described on page 145 of WO 08/020079.

Generally, the concentration of the polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the polypeptides of the invention required for use in treatment will vary not only with the particular polypeptide selected but also with the route of administration, the nature of the condition being treated and the age and condition of the patient and will be ultimately at the discretion of the attendant physician or clinician. Also the dosage of the polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one disease or disorder associated with HGF, said method comprising administering, to a subject in need thereof, a pharmaceutically active amount of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease or disorder that is associated with HGF, with its biological or pharmacological activity, and/or with the biological pathways or signaling in which HGF is involved, said method comprising administering, to a subject in need thereof, a pharmaceutically active amount of an amino acid sequence of the invention, of a polypeptide of the invention and/or of a pharmaceutical composition comprising the same. In an embodiment, the invention relates to a method for the prevention and/or treatment of at least one disease or disorder that can be treated by modulating HGF, its biological or pharmacological activity, and/or the biological pathways or signaling in which HGF is involved, said method comprising administering, to a subject in need thereof, a pharmaceutically active amount of a polypeptide of the invention, and/or of a pharmaceutical composition comprising the same. In an embodiment, said pharmaceutically effective amount may be an amount that is sufficient to modulate HGF, its biological or pharmacological activity, and/or the biological pathways or signaling in which HGF is involved; and/or an amount that provides a level of the polypeptide of the invention in the circulation that is sufficient to modulate HGF, its biological or pharmacological activity, and/or the biological pathways or signaling in which HGF is involved.

In an embodiment the invention relates to a method for the prevention and/or treatment of at least one disease or disorder that can be prevented and/or treated by administering a polypeptide of the invention, or a nucleotide construct of the invention encoding the same, and/or of a pharmaceutical composition comprising the same, to a patient. In an embodiment, the method comprises administering a pharmaceutically active amount of a polypeptide of the invention, or a nucleotide construct of the invention encoding the same, and/or of a pharmaceutical composition comprising the same to a subject in need thereof.

In an embodiment the invention relates to a method for the prevention and/or treatment of at least one disease or disorder that can be prevented and/or treated by inhibiting binding of HGF to c-Met in specific cells or in a specific tissue of a subject to be treated (and in particular, by inhibiting binding of HGF to c-Met in cancer cells or in a tumor present in the subject to be treated), said method comprising administering a pharmaceutically active amount of a polypeptide of the invention, or a nucleotide construct of the invention encoding the same, and/or of a pharmaceutical composition comprising the same, to a subject in need thereof.

In an embodiment, the invention relates to a method for the prevention and/or treatment of at least one disease or disorder chosen from the group consisting of the diseases and disorders listed herein, said method comprising administering, to a subject in need thereof, a polypeptide of the invention, or a nucleotide construct of the invention encoding the same, and/or of a pharmaceutical composition comprising the same.

In an embodiment, the invention relates to a method for immunotherapy, and in particular for passive immunotherapy, which method comprises administering, to a subject suffering from or at risk of the diseases and disorders mentioned herein, a pharmaceutically active amount of a polypeptide of the invention, or a nucleotide construct of the invention encoding the same, and/or of a pharmaceutical composition comprising the same.

In the above methods, the amino acid sequences, polypeptides of the invention and/or the compositions comprising the same can be administered in any suitable manner, depending on the specific pharmaceutical formulation or composition to be used. Thus, the polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more polypeptides of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency of the specific polypeptide of the invention to be used, the specific route of administration and the specific pharmaceutical formulation or composition used, the polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

In an embodiment, a single contiguous polypeptide of the invention will be used. In one embodiment two or more polypeptides of the invention are provided in combination.

The polypeptides of the invention may be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgment.

In particular, the polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician, and generally include the cytostatic and preferably cytotoxic active principles usually applied for the treatment of the tumor to be treated.

Specifically contemplated combinations for use with the polypeptides of the invention for oncology include, but are not limited to, e.g., RON antagonists, CXCR4 antagonists such as e.g. AMD3100, other chemokine receptor antagonists, taxol; gemcitabine; cisplatin; cIAP inhibitors (such as inhibitors to cIAP1, cIAP2 and/or XIAP); MEK inhibitors including but not limited to, e.g., U0126, PD0325901; bRaf inhibitors including but not limited to, e.g., RAF265; and mTOR inhibitors including but not limited to, e.g., RAD001; VEGF inhibitors including but not limited to e.g. bevacizumab, sutinib and sorafenib; ERBB inhibitors, such as, for instance, EGFR-inhibitors, including but not limited to specific small molecule kinase inhibitors, e.g. erlotinib, gefitinib; antibodies, e.g. cetuximab, nimotuzumab, panitumumab, necitumumab, IMC-C225 (Erbitux, Imclone), EMD72000 (Merck Darmstadt), ABX-EGF (Abgenix), h-R3 (theraCIM, YM Biosciences) and Humax-EGFR (Genmab); dual- or multispecific small molecule kinase inhibitors, e.g. lapatinib (EGFR&HER2), vandetanib (EGFR, RET, VEGFR2), neratinib (EGFR, HER2, HER4) and PF-299804 (EGFR, HER2, HER4), HER2-inhibitors including but not limited to e.g. trastuzumab and lapatinib; HER3-inhibitors; HER4 inhibitors; PDGFR, FGFR, src, JAK, STAT and/or GSK3 inhibitors; selective estrogen receptor modulators including but not limited to tamoxifen; estrogen receptor downregulators including but not limited to fulvestrant. Specific contemplated combinations for use with the polypeptides of the invention for e.g. inflammatory and other conditions also include, but are not limited to, e.g., interferon beta 1 alpha and beta, IFN alpha 2b; natalizumab; TNF alpha antagonists including but not limited to e.g. infliximab, adalimumab, certolizumab pegol, etanercept; disease-modifying antirheumatic drugs such as e.g. methotrexate (MTX); glucocorticoids including but not limited to e.g. dexamethasone, hydrocortisone; nonsteroidal anti-inflammatory drugs including but not limited to e.g. ibuprofen, sulindac; IL-6 or IL-6R inhibitors including but not limited to e.g. RoActemra, ALD518. In addition combinations for use with the polypeptides of the invention for oncology indications include but are not limited to non-targeted chemotherapeutics such as cytotoxics and/or cytostatics. The invention also comprises products and/or compositions comprising the polypeptides of the invention in combination with other antibodies and/or chemical compounds directed against other growth factors involved in tumor progression or metastasis and/or compounds and/or anticancer agents or agents conjugated with toxins and their use for the prevention and/or the treatment of certain cancers.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of polypeptide of the invention in the preparation of a pharmaceutical composition for prevention and/or treatment of at least one disease and disorder associated with HGF; and/or for use in one or more of the methods of treatment mentioned herein.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases and disorders mentioned herein.

The invention relates to the use of a polypeptide of the invention, or a nucleotide encoding the same, in the preparation of a pharmaceutical composition for the prevention and/or treatment of at least one disease or disorder that can be prevented and/or treated by administering a polypeptide of the invention, or a nucleotide encoding the same, and/or a pharmaceutical composition of the same to a patient.

More in particular, the invention relates to the use of a polypeptide of the invention, or a nucleotide encoding the same, in the preparation of a pharmaceutical composition for the prevention and/or treatment of diseases and disorders associated with HGF, and in particular for the prevention and treatment of one or more of the diseases and disorders listed herein.

Again, in such a pharmaceutical composition, the one or more polypeptide(s) of the invention, or nucleotide(s) encoding the same, and/or a pharmaceutical composition of the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in an a single cell or multi-cellular organism, and in particular in a mammal, and more in particular in a human being, such as in a human being that is at risk of or suffers from a disease or disorder of the invention).

In the context of the present invention, "modulating" or "to modulate" generally means reducing or inhibiting the activity of HGF and in particular human HGF (SEQ ID NO: 1), as measured using a suitable in vitro, cellular or in vivo assay (such as those mentioned herein). In particular, reducing or inhibiting the activity of HGF and in particular human HGF (SEQ ID NO: 1), as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to activity of HGF and in particular human HGF (SEQ ID NO: 1) in the same assay under the same conditions but without the presence of the polypeptide of the invention.

Modulating may for example involve reducing or inhibiting the binding of HGF to one of its substrates or receptors and/or competing with other ligands, substrate for binding to c-Met. Alternatively, modulating may involve inhibiting the internalization, inducing internalization in order to reduce c-Met level and as such reducing signaling, homodimerization of c-Met and/or promoting of shedding of c-Met and thus may inhibit HGF dependent c-Met activation.

The invention further relates to methods for preparing or generating the immunoglobulin single variable domains, polypeptides, nucleic acids, host cells, products and compositions described herein. Some preferred but non-limiting examples of such methods will become clear from the further description herein.

Generally, these methods may comprise the steps of:
a) providing a set, collection or library of immunoglobulin single variable domains; and
b) screening said set, collection or library of immunoglobulin single variable domains for immunoglobulin single variable domains that can bind to and/or have affinity for HGF and in particular human HGF (SEQ ID NO: 1); and
c) isolating the amino acid sequence(s) that can bind to and/or have affinity for HGF and in particular human HGF (SEQ ID NO: 1).

In such a method, the set, collection or library of immunoglobulin single variable domains may be any suitable set, collection or library of immunoglobulin single variable domains. For example, the set, collection or library of immunoglobulin single variable domains may be a set, collection or library of immunoglobulin sequences (as described herein), such as a naive set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of immunoglobulin single variable domains may be a set, collection or library of heavy or light chain variable domains (such as VL-, VH- or VHH domains, preferably VHH domains). For example, the set, collection or library of immunoglobulin single variable domains may be a set, collection or library of domain antibodies or single domain antibodies, or may be a set, collection or library of immunoglobulin single variable domains that are capable of functioning as a domain antibody or single domain antibody.

In a preferred aspect of this method, the set, collection or library of immunoglobulin single variable domains may be an immune set, collection or library of immunoglobulin sequences, for example derived from a mammal that has been suitably immunized with HGF and in particular human HGF (SEQ ID NO: 1) or with a suitable antigenic determinant based thereon or derived there from, such as an antigenic part, fragment, region, domain, loop or other epitope thereof. In one particular aspect, said antigenic determinant may be an extracellular part, region, domain, loop or other extracellular epitope(s).

In the above methods, the set, collection or library of immunoglobulin single variable domains may be displayed on a phage, phagemid, ribosome or suitable micro-organism (such as yeast), such as to facilitate screening. Suitable methods, techniques and host organisms for displaying and screening (a set, collection or library of) immunoglobulin single variable domains will be clear to the person skilled in the art, for example on the basis of the further disclosure herein. Reference is also made to the review by Hoogenboom in Nature Biotechnology, 23:1105-1116 (2005).

In another aspect, the method for generating immunoglobulin single variable domains comprises at least the steps of:
a) providing a collection or sample of cells expressing immunoglobulin single variable domains;
b) screening said collection or sample of cells for cells that express an amino acid sequence that can bind to and/or have affinity for HGF and in particular human HGF (SEQ ID NO: 1); and
c) either (i) isolating said amino acid sequence; or (ii) isolating from said cell a nucleic acid sequence that encodes said amino acid sequence, followed by expressing said amino acid sequence.

In another aspect, the method for generating an amino acid sequence directed against HGF and in particular human HGF (SEQ ID NO: 1) may comprise at least the steps of:
a) providing a set, collection or library of nucleic acid sequences encoding immunoglobulin single variable domains;
b) screening said set, collection or library of nucleic acid sequences for nucleic acid sequences that encode an amino acid sequence that can bind to and/or has affinity for HGF and in particular human HGF (SEQ ID NO: 1); and
c) isolating said nucleic acid sequence, followed by expressing said amino acid sequence.

In such a method, the set, collection or library of nucleic acid sequences encoding immunoglobulin single variable domains may for example be a set, collection or library of nucleic acid sequences encoding a naive set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

In another aspect, the method for generating an amino acid sequence directed against HGF and in particular human HGF (SEQ ID NO: 1) may comprise at least the steps of:
a) providing a set, collection or library of nucleic acid sequences encoding immunoglobulin single variable domains;
b) screening said set, collection or library of nucleic acid sequences for nucleic acid sequences that encode an amino acid sequence that can bind to and/or has affinity for HGF and in particular human HGF (SEQ ID NO: 1) and that is cross-blocked or is cross blocking a immunoglobulin single variable domain or polypeptide of the invention, e.g. SEQ ID NOs: 6 to 27, preferably SEQ ID NOs: 7, 8, 10, 15, 16, 18 and 20-25, even more preferably SEQ ID NOs: 7 and 18; and
c) isolating said nucleic acid sequence, followed by expressing said amino acid sequence.

In preferred aspect, the method for generating an amino acid sequence directed against HGF and in particular human HGF (SEQ ID NO: 1) may comprise at least the steps of:
a) providing a set, collection or library of immunoglobulin single variable domains; and
b) screening said set, collection or library of immunoglobulin single variable domains for immunoglobulin single variable domains that can bind to and/or have affinity for HGF and in particular human HGF (SEQ ID NO: 1); and
c) isolating the amino acid sequence(s) that can bind to and/or have affinity for HGF and in particular human HGF (SEQ ID NO: 1).

In such a method, the set, collection or library of immunoglobulin single variable domains may be any suitable set, collection or library of immunoglobulin single variable domains. For example, the set, collection or library of immunoglobulin single variable domains may be a set, collection or library of immunoglobulin sequences (as described herein), such as a naive set, collection or library of immunoglobulin sequences; a synthetic or semi-synthetic set, collection or library of immunoglobulin sequences; and/or a set, collection or library of immunoglobulin sequences that have been subjected to affinity maturation. In a preferred aspect, the set, collection or library of immunoglobulin single variable domains may be a set, collection or library of immunoglobulin sequences (as described herein), such as a synthetic set, collection or library of immunoglobulin sequences. In the above methods, the set, collection or library of immunoglobulin single variable domains may be displayed on a phage, phagemid, ribosome or suitable micro-organism (such as yeast), such as to facilitate screening. Suitable methods, techniques and host organisms for displaying and screening (a set, collection or library of) immunoglobulin single variable domains will be clear to the person skilled in the art such as e.g. described by Knappik et al., J. Mol. Biol. 2000 Feb. 11, 296:57-86.

Suitable methods, techniques and host organisms for displaying and screening (a set, collection or library of) immunoglobulin single variable domains will be clear to the person skilled in the art, for example on the basis of the further disclosure herein. Reference is also made to the review by Hoogenboom in Nature Biotechnology, 23:1105-1116 (2005).

The invention also relates to immunoglobulin single variable domains that are obtained by the above methods, or alternatively by a method that comprises the one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Also, following the steps above, one or more immunoglobulin single variable domains of the invention may be suitably humanized, camelized or otherwise sequence optimized (e.g. sequence optimized for manufacturability, stability and/or solubility); and/or the amino acid sequence(s) thus obtained may be linked to each other or to one or more other suitable immunoglobulin single variable domains (optionally via one or more suitable linkers) so as to provide a polypeptide of the invention. Also, a nucleic acid sequence encoding an amino acid sequence of the invention may be suitably humanized, camelized or otherwise sequence optimized (e.g. sequence optimized for manufacturability, stability and/or solubility) and suitably expressed; and/or one or more nucleic acid sequences encoding an amino acid sequence of the invention may be linked to each other or to one or more nucleic acid sequences that encode other suitable immunoglobulin single variable domains (optionally via nucleotide sequences that encode one or more suitable linkers), after which the nucleotide sequence thus obtained may be suitably expressed so as to provide a polypeptide of the invention.

The invention further relates to applications and uses of the immunoglobulin single variable domains, compounds, constructs, polypeptides, nucleic acids, host cells, products and compositions described herein, as well as to methods for the diagnosis, prevention and/or treatment for diseases and disorders associated with HGF and in particular human HGF (SEQ ID NO: 1). Some preferred but non-limiting applications and uses will become clear from the further description herein.

The invention also relates to the immunoglobulin single variable domains, compounds, constructs, polypeptides, nucleic acids, host cells, products and compositions described herein for use in therapy.

In particular, the invention also relates to the immunoglobulin single variable domains, compounds, constructs, polypeptides, nucleic acids, host cells, products and compositions described herein for use in therapy of a disease or disorder that can be prevented or treated by administering, to a subject in need thereof, of (a pharmaceutically effective amount of) an amino acid sequence, compound, construct, ISVD or polypeptide as described herein.

More in particular, the invention relates to the immunoglobulin single variable domains, compounds, constructs, polypeptides, nucleic acids, host cells, products and compositions described herein for use in therapy of cancer.

Polypeptides of the invention and immunoglobulin single variable domains (that form part of the polypeptides of the invention) may be altered in order to further improve potency or other desired properties.

Generally, an immunoglobulin single variable domain can be defined as a polypeptide with the formula 1

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively (cf. above).

Some particularly preferred, but non-limiting combinations of CDR sequences, as well as preferred combinations of CDR sequences and framework sequences, are mentioned in Table B-2 below, which lists the CDR sequences and framework sequences that are present in a number of preferred (but non-limiting) immunoglobulin single variable domains of the invention. As will be clear to the skilled person, a combination of CDR1, CDR2 and CDR3 sequences that occur in the same clone (i.e., CDR1, CDR2 and CDR3 sequences that are mentioned on the same line or row in Table B-2) will usually be preferred (although the invention in its broadest sense is not limited thereto, and also comprises other suitable combinations of the CDR sequences mentioned in Table B-2). Also, a combination of CDR sequences and framework sequences that occur in the same clone (i.e. CDR sequences and framework sequences that are mentioned on the same line or row in Table B-2) will usually be preferred (although the invention in its broadest sense is not limited thereto, and also comprises other suitable combinations of the CDR sequences and framework sequences mentioned in Table B-2, as well as combinations of such CDR sequences and other suitable framework sequences, e.g., as further described herein).

Also, in the immunoglobulin single variable domains of the invention that comprise the combinations of CDRs mentioned in Table B-2, each CDR can be replaced by a CDR chosen from the group consisting of immunoglobulin single variable domains that have at least 80%, preferably at least 90%, more preferably at least 95%, even more preferably at least 99% sequence identity (as defined herein) with the mentioned CDRs, in which:

i) any amino acid substitution in such a CDR is preferably, and compared to the corresponding CDR sequence mentioned in Table B-2, a conservative amino acid substitution (as defined herein); and/or
ii) any such CDR sequence preferably only contains amino acid substitutions, and no amino acid deletions or insertions, compared to the corresponding CDR sequence mentioned in Table B-2; and/or
iii) any such CDR sequence is a CDR that is derived by means of a technique for affinity maturation known per se, and in particular starting from the corresponding CDR sequence mentioned in Table B-2.

However, as will be clear to the skilled person, the (combinations of) CDR sequences, as well as (the combinations of) CDR sequences and framework sequences mentioned in Table B-2 will generally be preferred.

Thus, in the immunoglobulin single variable domains of the invention, at least one of the CDR1, CDR2 and CDR3 sequences present is suitably chosen from the group consisting of the CDR1, CDR2 and CDR3 sequences, respectively, listed in Table B-2; or from the group of CDR1, CDR2 and CDR3 sequences, respectively, that have at least 80%, preferably at least 90%, more preferably at least 95%, even more preferably at least 99% "sequence identity" (as defined herein) with at least one of the CDR1, CDR2 and CDR3 sequences, respectively, listed in Table B-2; and/or from the group consisting of the CDR1, CDR2 and CDR3 sequences, respectively, that have 3, 2 or only 1 "amino acid difference(s)" (as defined herein) with at least one of the CDR1, CDR2 and CDR3 sequences, respectively, listed in Table B-2.

In this context, by "suitably chosen" is meant that, as applicable, a CDR1 sequence is chosen from suitable CDR1 sequences (i.e., as defined herein), a CDR2 sequence is chosen from suitable CDR2 sequences (i.e., as defined herein), and a CDR3 sequence is chosen from suitable CDR3 sequence (i.e. as defined herein), respectively. More in particular, the CDR sequences are preferably chosen such that the immunoglobulin single variable domains of the invention bind to HGF and in particular human HGF (SEQ ID NO: 1) with an affinity (suitably measured and/or expressed as a EC50 value, or alternatively as an $IC_{50}$ value, as further described herein in various in vitro and/or in vivo potency or other assays) that is as defined herein.

In particular, in the immunoglobulin single variable domains of the invention, at least the CDR3 sequence present is suitably chosen from the group consisting of the CDR3 sequences listed in Table B-2 or from the group of CDR3 sequences that have at least 80%, preferably at least 90%, more preferably at least 95%, even more preferably at least 99% sequence identity with at least one of the CDR3 sequences listed in Table B-2; and/or from the group consisting of the CDR3 sequences that have 3, 2 or only 1 amino acid difference(s) with at least one of the CDR3 sequences listed in Table B-2.

Preferably, in the immunoglobulin single variable domains of the invention, at least two of the CDR1, CDR2 and CDR3 sequences present are suitably chosen from the group consisting of the CDR1, CDR2 and CDR3 sequences, respectively, listed in Table B-2 or from the group consisting of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-2; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table B-2.

In particular, in the immunoglobulin single variable domains of the invention, at least the CDR3 sequence present is suitably chosen from the group consisting of the CDR3 sequences listed in Table B-2 or from the group of CDR3 sequences that have at least 80%, preferably at least 90%, more preferably at least 95%, even more preferably at least 99% sequence identity with at least one of the CDR3 sequences listed in Table B-2, respectively; and at least one of the CDR1 and CDR2 sequences present is suitably chosen from the group consisting of the CDR1 and CDR2 sequences, respectively, listed in Table B-2 or from the group of CDR1 and CDR2 sequences, respectively, that have at least 80%, preferably at least 90%, more preferably at least 95%, even more preferably at least 99% sequence identity with at least one of the CDR1 and CDR2 sequences, respectively, listed in Table B-2; and/or from the group consisting of the CDR1 and CDR2 sequences, respectively, that have 3, 2 or only 1 amino acid difference(s) with at least one of the CDR1 and CDR2 sequences, respectively, listed in Table B-2.

Most preferably, in the immunoglobulin single variable domains of the invention, all three CDR1, CDR2 and CDR3 sequences present are suitably chosen from the group consisting of the CDR1, CDR2 and CDR3 sequences, respectively, listed in Table B-2 or from the group of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-2; and/or from the group consisting of the CDR1, CDR2 and CDR3 sequences, respectively, that have 3, 2 or only 1 amino acid difference(s) with at least one of the CDR1, CDR2 and CDR3 sequences, respectively, listed in Table B-2.

Even more preferably, in the immunoglobulin single variable domains of the invention, at least one of the CDR1, CDR2 and CDR3 sequences present is suitably chosen from the group consisting of the CDR1, CDR2 and CDR3 sequences, respectively, listed in Table B-2. Preferably, in this aspect, at least one or preferably both of the other two CDR sequences present are suitably chosen from CDR sequences that have at least 80%, preferably at least 90%, more preferably at least 95%, even more preferably at least 99% sequence identity with at least one of the corresponding CDR sequences, respectively, listed in Table B-2; and/or from the group consisting of the CDR sequences that have 3, 2 or only 1 amino acid difference(s) with at least one of the corresponding sequences, respectively, listed in Table B-2.

In particular, in the immunoglobulin single variable domains of the invention, at least the CDR3 sequence present is suitably chosen from the group consisting of the CDR3 listed in Table B-2. Preferably, in this aspect, at least one and preferably both of the CDR1 and CDR2 sequences present are suitably chosen from the groups of CDR1 and CDR2 sequences, respectively, that have at least 80%, preferably at least 90%, more preferably at least 95%, even more preferably at least 99% sequence identity with the CDR1 and CDR2 sequences, respectively, listed in Table B-2; and/or from the group consisting of the CDR1 and CDR2 sequences, respectively, that have 3, 2 or only 1 amino acid difference(s) with at least one of the CDR1 and CDR2 sequences, respectively, listed in Table B-2.

Even more preferably, in the immunoglobulin single variable domains of the invention, at least two of the CDR1, CDR2 and CDR3 sequences present are suitably chosen from the group consisting of the CDR1, CDR2 and CDR3 sequences, respectively, listed in Table B-2. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-2; and/or from the group consisting of CDR sequences that have 3, 2 or only 1 amino acid difference(s) with at least one of the corresponding sequences listed in Table B-2.

In particular, in the immunoglobulin single variable domains of the invention, at least the CDR3 sequence is suitably chosen from the group consisting of the CDR3 sequences listed in Table B-2, and either the CDR1 sequence or the CDR2 sequence is suitably chosen from the group consisting of the CDR1 and CDR2 sequences, respectively, listed in Table B-2. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-2; and/or from the group consisting of CDR sequences that have 3, 2 or only 1 amino acid difference(s) with the corresponding CDR sequences listed in Table B-2.

Even more preferably, in the immunoglobulin single variable domains of the invention, all three CDR1, CDR2 and CDR3 sequences present are suitably chosen from the group consisting of the CDR1, CDR2 and CDR3 sequences, respectively, listed in Table B-2.

Also, generally, the combinations of CDR's listed in Table B-2 (i.e., those mentioned on the same line or row in Table B-2) are preferred. Thus, it is generally preferred that, when a CDR in a immunoglobulin single variable domain of the invention is a CDR sequence mentioned in Table B-2 or is suitably chosen from the group of CDR sequences that have at least 80%, preferably at least 90%, more preferably at least 95%, even more preferably at least 99% sequence identity with a CDR sequence listed in Table B-2; and/or from the group consisting of CDR sequences that have 3, 2 or only 1 amino acid difference(s) with a CDR sequence listed in Table B-2, that at least one and preferably both of the other CDR's are suitably chosen from the CDR sequences that belong to the same combination in Table B-2 (i.e., mentioned on the same line or row in Table B-2) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDRs mentioned in Table B-2, e.g., mentioned on the same row in Table B-2.

Thus, by means of non-limiting examples, a polypeptide of the invention can for example comprise a CDR1 sequence that has more than 80% sequence identity with one of the CDR1 sequences mentioned in Table B-2, a CDR2 sequence that has 3, 2 or 1 amino acid difference with one of the CDR2 sequences mentioned in Table B-2 (but belonging to a different combination, e.g., mentioned on different rows in Table B-2), and a CDR3 sequence.

Some preferred immunoglobulin single variable domains of the invention may for example comprise: (1) a CDR1 sequence that has more than 80% sequence identity with one of the CDR1 sequences mentioned in Table B-2; a CDR2 sequence that has 3, 2 or 1 amino acid difference with one of the CDR2 sequences mentioned in Table B-2 (but belonging to a different combination, e.g. mentioned on different rows in Table B-2); and a CDR3 sequence that has more than 80% sequence identity with one of the CDR3 sequences mentioned in Table B-2 (but belonging to a different combination, e.g. mentioned on different rows in Table B-2); or (2) a CDR1 sequence that has more than 80% sequence identity with one of the CDR1 sequences mentioned in Table B-2; a CDR2 sequence, and one of the CDR3 sequences listed in Table B-2; or (3) a CDR1 sequence; a CDR2 sequence that has more than 80% sequence identity with one of the CDR2 sequence listed in Table B-2; and a CDR3 sequence that has 3, 2 or 1 amino acid differences with the CDR3 sequence mentioned in Table B-2 that belongs to the same combination as the CDR2 sequence, e.g., mentioned on the same rows in Table B-2.

Some particularly preferred immunoglobulin single variable domains of the invention may for example comprise: (1) a CDR1 sequence that has more than 80% sequence identity with one of the CDR1 sequences mentioned in Table B-2; a CDR2 sequence that has 3, 2 or 1 amino acid difference with the CDR2 sequence mentioned in Table B-2 that belongs to the same combination; and a CDR3 sequence that has more than 80% sequence identity with the CDR3 sequence mentioned in Table B-2 that belongs to the same combination; (2) a CDR1 sequence; a CDR2 listed in Table B-2 and a CDR3 sequence listed in Table B-2 (in which the CDR2 sequence and CDR3 sequence may belong to different combinations).

Some even more preferred immunoglobulin single variable domains of the invention may for example comprise: (1) a CDR1 sequence that has more than 80% sequence identity with one of the CDR1 sequences mentioned in Table B-2; the CDR2 sequence listed in Table B-1 that belongs to the same combination; and a CDR3 sequence mentioned in Table B-2 that belongs to a different combination (e.g. mentioned on different rows in Table B-2); or (2) a CDR1 sequence mentioned in Table B-2; a CDR2 sequence that has 3, 2 or 1 amino acid differences with the CDR2 sequence mentioned in Table B-2 that belongs to the same combination; and a CDR3 sequence that has more than 80% sequence identity with the CDR3 sequence listed in Table B-2 that belongs to the same or a different combination.

Particularly preferred immunoglobulin single variable domains of the invention may for example comprise a CDR1 sequence mentioned in Table B-2, a CDR2 sequence that has more than 80% sequence identity with the CDR2 sequence mentioned in Table B-2 that belongs to the same combination; and the CDR3 sequence mentioned in Table B-2 that belongs to the same combination.

In an even more preferred immunoglobulin single variable domains of the invention, the CDR1, CDR2 and CDR3 sequences present are suitably chosen from one of the combinations of CDR1, CDR2 and CDR3 sequences, respectively, listed in Table B-2. Most preferably CDR1 is SEQ ID NO: 40.

According to another preferred, but non-limiting aspect of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In another preferred, but non-limiting aspect, the invention relates to a immunoglobulin single variable domain in which the CDR sequences (as defined herein) have more than 80%, preferably more than 90%, more preferably more than 95%, such as 99% or more sequence identity (as defined herein) with the CDR sequences of at least one of the immunoglobulin single variable domains of SEQ ID NOs: 6 to 27, preferably SEQ ID NOs: 7, 8, 10, 15, 16, 18 and 20-25, even more preferably SEQ ID NOs: 7 and 18.

Another preferred, but non-limiting aspect of the invention relates to humanized variants of the immunoglobulin single variable domains of SEQ ID NOs: 6 to 27, preferably SEQ ID NOs: 7, 8, 10, 15, 16, 18 and 20-25, even more preferably SEQ ID NOs: 7 and 18, that comprise, compared to the corresponding native $V_{HH}$ sequence, at least one humanizing substitution (as defined herein), and in particular at least one humanizing substitution in at least one of its framework sequences (as defined herein).

It will be clear to the skilled person that the immunoglobulin single variable domains that are mentioned herein as "preferred" (or "more preferred", "even more preferred", etc.) are also preferred (or more preferred, or even more preferred, etc.) for use in the polypeptides described herein. Thus, polypeptides that comprise or essentially consist of one or more "preferred" immunoglobulin single variable domains of the invention will generally be preferred, and polypeptides that comprise or essentially consist of one or more "more preferred" immunoglobulin single variable domains of the invention will generally be more preferred, etc.

Another aspect of this invention relates to a nucleic acid that encodes an amino acid sequence of the invention (such as an immunoglobulin single variable domain of the invention) or a polypeptide of the invention comprising the same. Again, as generally described herein for the nucleic acids of the invention, such a nucleic acid may be in the form of a genetic construct, as defined herein.

In another preferred, but non-limiting aspect, the invention relates to nucleic acid sequences of immunoglobulin single variable domain in which the sequences (as defined herein) have more than 80%, preferably more than 90%, more preferably more than 95%, such as 99% or more sequence identity (as defined herein) with the sequences of at least one of nucleic acid sequence encoding the immunoglobulin single variable domains SEQ ID NOs: 6 to 27, preferably SEQ ID NOs: 7, 8, 10, 15, 16, 18 and 20-25, even more preferably SEQ ID NOs: 7 and 18.

In another aspect, the invention relates to nucleic acid sequences that comprise the nucleic acid sequences of immunoglobulin single variable domain in which the sequences (as defined herein) have more than 80%, preferably more than 90%, more preferably more than 95%, such as 99% or more sequence identity (as defined herein) with the sequences of at least one of nucleic acid sequence encoding the immunoglobulin single variable domains SEQ ID NOs: 6 to 27, preferably SEQ ID NOs: 7, 8, 10, 15, 16, 18 and 20-25, even more preferably SEQ ID NOs: 7 and 18.

In another aspect, the invention relates to a host or host cell which expresses or that is capable of expressing an amino acid sequence (such as an immunoglobulin single variable domain) of the invention and/or a polypeptide of the invention comprising the same; and/or which contains a nucleic acid of the invention. Some preferred but non-limiting examples of such hosts or host cells will become clear from the further description herein.

As will be clear to the skilled person, one particularly useful method for preparing a polypeptide of the invention generally comprises the steps of:
i) the expression, in a suitable host cell or host organism (also referred to herein as a "host of the invention") or in another suitable expression system of a nucleic acid that encodes said amino acid sequence, polypeptide of the invention (also referred to herein as a "nucleic acid of the invention"), optionally followed by:
ii) isolating and/or purifying the polypeptide of the invention thus obtained.

In particular, such a method may comprise the steps of:
i) cultivating and/or maintaining a host of the invention under conditions that are such that said host of the invention expresses and/or produces at least one polypeptide of the invention; optionally followed by:
ii) isolating and/or purifying the polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the immunoglobulin single variable domains for the polypeptides of the invention given herein, and/or can be isolated from a suitable natural source. To provide analogs, nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a polypeptide of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g., to create cassettes and/or regions that may easily be digested and/or ligated using suitable restriction enzymes), and/or the introduction of mutations by means of a PCR reaction using one or more "mismatched" primers, using for example a sequence of a naturally occurring form of HGF and in particular human HGF (SEQ ID NO: 1) as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art and as described on pages 131-134 of WO 08/020079 (incorporated herein by reference). Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g., in a suitable host cell, host organism and/or expression system).

In a preferred but non-limiting aspect, a genetic construct of the invention comprises
i) at least one nucleic acid of the invention; operably connected to
ii) one or more regulatory elements, such as a promoter and optionally a suitable terminator; and optionally also
iii) one or more further elements of genetic constructs known per se;

in which the terms "operably connected" and "operably linked" have the meaning given on pages 131-134 of WO 08/020079; and in which the "regulatory elements", "promoter", "terminator" and "further elements" are as described on pages 131-134 of WO 08/020079; and in which the genetic constructs may further be as described on pages 131-134 of WO 08/020079.

The nucleic acids of the invention and/or the genetic constructs of the invention may be used to transform a host cell or host organism, i.e. for expression and/or production of the polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example those described on pages 134 and 135 of WO 08/020079, as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457, WO 96/34103 and WO 99/42077.

The immunoglobulin single variable domains, and polypeptides of the invention can for example also be produced in the milk of transgenic mammals, for example in the milk of rabbits, cows, goats or sheep (see for example U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombyx mori*.

Furthermore, the immunoglobulin single variable domains, and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of immunoglobulin single variable domains is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of immunoglobulin single variable domains or immunoglobulin single variable domain-containing protein therapeutics include strains of *E. coli, Pichia pastoris, S. cerevisiae* that are suitable for large scale expression/production/fermentation, and in particular for large scale pharmaceutical (i.e. GMP grade) expression/ production/fermentation. Suitable examples of such strains will be clear to the skilled person. Such strains and production/expression systems are also made available by companies such as Richter Helm (Hamburg, Germany) or CMC Biologics (Soeborg, Denmark).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a immunoglobulin single variable domain-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached), will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as E. coli do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired polypeptide to be obtained.

Thus, according to one non-limiting aspect of the invention, the polypeptide of the invention is glycosylated. According to another non-limiting aspect of the invention, the polypeptide of the invention is non-glycosylated.

According to one preferred, but non-limiting aspect of the invention, the polypeptide of the invention is produced in a bacterial cell, in particular a bacterial cell suitable for large scale pharmaceutical production, such as cells of the strains mentioned above.

According to another preferred, but non-limiting aspect of the invention, the polypeptide of the invention is produced in a yeast cell, in particular a yeast cell suitable for large scale pharmaceutical production, such as cells of the species mentioned above.

According to yet another preferred, but non-limiting aspect of the invention, the polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

As further described on pages 138 and 139 of WO 08/020079, when expression in a host cell is used to produce the immunoglobulin single variable domains, and the polypeptides of the invention, the immunoglobulin single variable domains, and polypeptides of the invention can be produced either intracellullarly (e.g., in the cytosol, in the periplasm or in inclusion bodies) and then isolated from the host cells and optionally further purified; or can be produced extracellularly (e.g. in the medium in which the host cells are cultured) and then isolated from the culture medium and optionally further purified. Thus, according to a non-limiting aspect of the invention, the polypeptide of the invention is an amino acid sequence, polypeptide that has been produced intracellularly and that has been isolated from the host cell, and in particular from a bacterial cell or from an inclusion body in a bacterial cell. According to another non-limiting aspect of the invention, the amino acid sequence, or polypeptide of the invention is an amino acid sequence, or polypeptide that has been produced extracellularly, and that has been isolated from the medium in which the host cell is cultivated.

Some preferred, but non-limiting promoters for use with these host cells include those mentioned on pages 139 and 140 of WO 08/020079.

Some preferred, but non-limiting secretory sequences for use with these host cells include those mentioned on page 140 of WO 08/020079.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), a polypeptide of the invention (and in case of a host organism: in at least one cell, part, tissue or organ thereof). The invention also includes further generations, progeny and/or offspring of the host cell or host organism of the invention, which may for instance be obtained by cell division or by sexual or asexual reproduction.

To produce/obtain expression of the immunoglobulin single variable domains of the invention, the transformed host cell or transformed host organism may generally be kept, maintained and/or cultured under conditions such that the (desired) amino acid sequence, or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the immunoglobulin single variable domains of the invention may be expressed in a constitutive manner, in a transient manner, or only when suitably induced.

It will also be clear to the skilled person that the amino acid sequence, or polypeptide of the invention may (first) be generated in an immature form (as mentioned above), which may then be subjected to post-translational modification, depending on the host cell/host organism used. Also, the amino acid sequence, or polypeptide of the invention may be glycosylated, again depending on the host cell/host organism used.

The amino acid sequence, or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, or polypeptide of the invention) and/or preparative immunological techniques (i.e. using antibodies against the amino acid sequence to be isolated).

The entire contents of all of the references (including literature references, issued patents, published patent applications, and co-pending patent applications) cited throughout this application are hereby expressly incorporated by reference, in particular for the teaching that is referenced herein.

The invention will now be further described by means of the following non-limiting preferred aspects, figures and examples:

EXAMPLES

Example 1: Identification of Anti-HGF ISVDs 1.1 Immunization and Selection of Neutralizing Anti-HGF Nanobodies Two llamas (No. 085 and No. 092; *Llama glama*) were immunized with 100 and 50 µg doses of human HGF (Peprotech, cat#100-39) according to the scheme outlined in Table 1. Proteins were administered in Stimune adjuvant (Cedi Diagnostics, Lelystad, The Netherlands). Blood was collected from these animals as indicated in Table 1.

TABLE 1

| Immunization protocol | | | |
|---|---|---|---|
| Day | Llama 085 | Llama 092 | Tissue collection |
| 0 | 100 µg | 100 µg | 100 ml naive blood (PBL$_N$) 50 ml pre-immune blood (NC0) 10 ml pre-immune blood |
| 7 | 100 µg | 100 µg | — |
| 14 | 50 µg | 50 µg | — |
| 21 | 50 µg | 50 µg | — |
| 28 | 50 µg | 50 µg | 10 ml immune blood |
| 35 | 50 µg | 50 µg | — |

TABLE 1-continued

| Immunization protocol | | | |
|---|---|---|---|
| Day | Llama 085 | Llama 092 | Tissue collection |
| 39 | | | 150 ml immune blood (PBL1) lymph node bow biopsy |
| 43 | | | 150 ml immune blood (PBL2) |
| 50 | 50 µg | 50 µg | — |
| 57 | | | 100 ml immune blood (NC1) |

The animal experiments were conducted with the approval of the Ethical Committee of the Faculty of Veterinary Medicine (University of Ghent, Belgium). Anti-HGF serum titers were evaluated using human HGF in an ELISA type of method, essentially as described before (Roovers et al., Cancer Immunol Immunother. 2007 56(3):303-317). The results are depicted in FIG. 1.

1.2 Library Construction

Anti-HGF Nanobodies were isolated using phage display, essentially as described previously (Roovers et al., Cancer Immunol Immunother. 2007 56(3):303-317). Briefly: Peripheral blood mononuclear cells were prepared from blood samples using Ficoll-Hypaque according to the manufacturer's instructions. Next, total RNA was extracted from these cells and used as starting material for RT-PCR to amplify Nanobodies encoding gene fragments. These fragments were cloned into phagemid vector pAX50. Phage was prepared according to standard methods (Roovers et al., Cancer Immunol Immunother. 2007 56(3):303-317.) and stored after filter sterilization at 4° C. for further use. Phage library size from both animals was $0.7 \times 10^8$ and $2.1 \times 10^8$, and percentages of insert 100 and 91.3%, respectively.

Phage libraries from llama No. 085 and No. 092 were used for one round of selection on human HGF. An overview of the different experimental conditions used in different selection strategies are shown in Table 2. HGF antigen was either immobilized directly in a microtiter plate or was captured on a monoclonal antibody directed against the alpha or beta chain of HGF. For direct immobilization HGF from R&D Systems (294-HG/CF; SEQ ID NO: 2) or Peprotech (100-39; SEQ ID NO: 3) was incubated in a Nunc Maxisorp plate at concentrations between 50 nM and 0.5 nM. In the capturing approach, different concentrations of HGF (from 5 nM to 0.05 nM) were added to microtiter wells coated with either MAB294 (R&D systems) or sc-53301 (Santa Cruz). Bound phage was eluted by addition of trypsin and rescued via infection of *E. coli*.

In another selection approach, phage was incubated in-solution with different concentrations (5 nM to 0.5 nM) of biotinylated HGF (biotinylated at Ablynx according to standard procedures), captured on streptavidin-coupled Dynabeads (Invitrogen) and eluted using trypsin. Phage eluates were rescued via infection of *E. coli*.

TABLE 2

| Experimental conditions used in different selection strategies | | | | | |
|---|---|---|---|---|---|
| Method 1 | Antigen 1 | Elution 1 | Method 3 | Antigen 3 | Elution 3 |
| Passive plate immobilization | HGF at 50 nM | Trypsin | streptavidin-coupled Dynabeads | Biotinylated HGF at 5 nM | Trypsin |
| Passive plate immobilization | HGF at 5 nM | Trypsin | streptavidin-coupled Dynabeads | Biotinylated HGF at 0.5 nM | Trypsin |

TABLE 2-continued

| Experimental conditions used in different selection strategies | | | | | |
|---|---|---|---|---|---|
| Passive plate immobilization | HGF at 0.5 nM | Trypsin | streptavidin-coupled Dynabeads | Biotinylated HGF at 0.05 nM | Trypsin |

| Method 2 | Antigen 2 | Elution 2 |
|---|---|---|
| Passive plate immobilization | Monoclonal antibody at 5 nM | Trypsin |
| Passive plate immobilization | Monoclonal antibody at 0.5 nM | Trypsin |
| Passive plate immobilization | Monoclonal antibody at 0.05 nM | Trypsin |

Selection outputs were analyzed for enrichment factor (# phage present in eluate relative to control). Based on these results the best selections were chosen for further analysis. Individual colonies were picked and grown in 96 deep well plates (1 ml volume). Nanobody expression was induced by addition of IPTG. Periplasmic extracts (volume: ~80 μl) were prepared according to standard methods (see for example the prior art and applications filed by applicant cited herein) Nanobodies were expressed as tagged proteins containing both c-myc and His6.

1.3 Selective Binding of the Nanobodies to Human HGF in ELISA

As a primary screen, Nanobody containing periplasmic extracts were analyzed for their ability to bind HGF. HGF from R&D Systems (reference number 294-HG/CF) was coated on ELISA plates at 21 μg/mL. Plates were washed and subsequently blocked using PBS with 1% casein. Periplasmic extracts of individual clones, prediluted 1/10 in PBS/0.1% casein/0.05% Tween, were added and plates were incubated at RT for 2 hours. Binding to immobilized HGF was detected using mouse anti-c-myc monoclonal antibody, followed by a horseradish peroxidase conjugated rabbit-anti-mouse (human and bovine serum protein pre-absorbed) monoclonal antibody for detection. Individual clones were scored as putative HGF binders if the clones showed high optical densities in the assay. Overall, more than 90% of the clones were able to bind HGF (data not shown).

1.4 Inhibition of Human HGF/c-Met-Fc Interaction in Alphascreen

Periplasmic extracts were then analyzed for their ability to block the interaction of human HGF (R&D systems) with c-Met-Fc (R&D systems; SEQ ID NO: 5). To this end, an AlphaScreen™ assay (Perkin Elmer) was set up and used as a screening assay.

Figure 2:
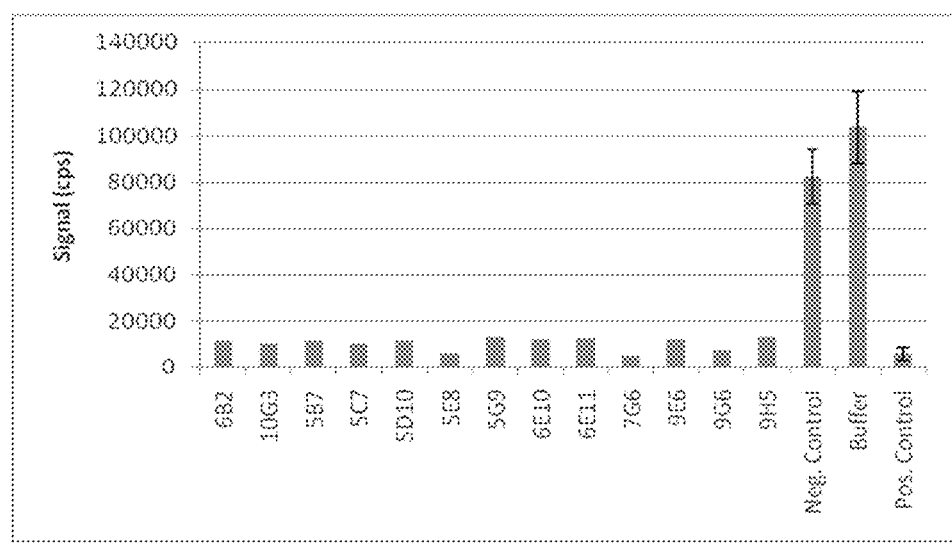
FIG. 2 Screen of periplasmic extracts using AlphaScreen™. The individual clones show a reduced signal when the HGF/c-Met interaction is blocked.

In brief, 5 μl of 1/5 prediluted periplasmic extract of individual Nanobody clones were incubated with 3 nM biotinylated HGF, 2 nM c-Met-Fc, streptavidin coated donor beads and anti-human IgG1 Fc Nanobody covalently coupled AlphaScreen acceptor beads. Monoclonal antibody clone 24612 (R&D systems) known to inhibit the HGF/c-Met-Fc interaction, was used as a positive control. Assays were read in an Envision AlphaScreen™ option fitted multimode reader (Perkin Elmer). Individual clones were scored as putative HGF/c-Met-Fc interaction inhibiting if the presence of the periplasmic extract decreased the fluorescent signal of the acceptor beads. Both inhibitory and non-inhibitory clones were identified. A 10-fold reduction in signal with respect to the negative control (irrelevant periplasmic extract and buffer) was used to select the HGF/c-Met inhibiting Nanobodies. As a positive control, anti-HGF monoclonal antibody (R&D systems, clone 24612) was included. FIG. 2 depicts an example of screen of periplasmic extracts using AlphaScreen.

1.5 Off-Rate Determination of HGF Binding Nanobodies

Off-rate constants ($K_{off}$) of individual Nanobodies were determined by surface plasmon resonance on a Biacore T100 instrument.

Human HGF (R&D) was amine-coupled to a CM5 sensor chip at a density of 2500 relative units. Remaining reactive groups were inactivated using ethanolamine. Nanobody binding was assessed at a single dilution of periplasmic extract, whereas c-Met was tested with a single concentration of 10 nM. Each sample was injected for 2 min at a flow rate of 45 μl/min to allow for binding to chip-bound antigen. Next, binding buffer without Nanobody was sent over the chip at the same flow rate to allow dissociation of bound Nanobody. After 10 min, remaining bound analyte was removed by injecting regeneration solution (1M NaCl, 50 mM NaOH). Binding/dissociation curves were used to calculate $k_{off}$ values, which are shown in Table 3.

TABLE 3

| Off-rate screening of unpurified Nanobodies using BIAcore | | | | | |
|---|---|---|---|---|---|
| Clone | kd (s⁻¹) | Clone | kd (s⁻¹) | Clone | kd (s⁻¹) |
| 1A1 | 1.89E−02 | 2A1 | 4.51E−03 | 6F6 | 5.45E−03 |
| 1A7 | 3.21E−03 | 2A3 | 2.19E−03 | 6G6 | 1.78E−03 |
| 1B4 | 3.13E−03 | 2A4 | 2.62E−03 | 6H6 | 1.39E−02 |
| 1B9 | 1.05E−02 | 2A9 | 3.27E−03 | 6B6 | 9.37E−06 |
| 1B11 | 2.82E−03 | 2B3 | 3.14E−03 | 5B7 | 1.75E−03 |
| 1C6 | 6.50E−03 | 2B7 | 3.26E−03 | 5C7 | 1.90E−03 |
| 1C7 | 2.86E−03 | 2B9 | 3.20E−03 | 5E8 | 1.63E−03 |
| 1C8 | 3.25E−03 | 2B11 | 1.78E−03 | 5G9 | 8.00E−04 |
| 1D7 | 3.41E−03 | 2C1 | 2.18E−03 | 5D10 | 1.99E−03 |
| 1D8 | 3.36E−03 | 2C3 | 3.31E−03 | 6B2 | 7.74E−04 |
| 1D10 | 3.42E−03 | 2C5 | 2.56E−03 | 6E10 | 3.24E−04 |
| 1E2 | 3.12E−03 | 2C9 | 3.28E−03 | 6E11 | 1.68E−03 |
| 1E4 | 3.63E−03 | 2C11 | 2.68E−03 | 8G3 | 1.95E−03 |
| 1E7 | 3.49E−03 | 2D2 | 2.62E−03 | 8C10 | 8.35E−05 |
| 1E8 | 3.61E−03 | 2E7 | 3.23E−03 | 9E3 | 1.72E−03 |
| 1E9 | 3.14E−03 | 2F5 | 2.15E−03 | 9B5 | 1.43E−03 |
| 1E11 | 3.24E−03 | 2G8 | 2.32E−03 | 9H5 | 1.55E−03 |
| 1F3 | 3.45E−03 | 2H8 | 3.29E−03 | 9E6 | 2.18E−03 |
| 1F6 | 6.57E−03 | 2H11 | 3.11E−03 | 9G6 | 1.07E−03 |
| 1F7 | 3.36E−03 | 2F11 | 3.15E−03 | 9A10 | 2.61E−03 |
| 1F8 | 3.45E−03 | 6A6 | 1.64E−03 | 10G3 | 3.77E−04 |
| 1F10 | 1.08E−02 | 7G6 | 9.36E−04 | c-Met | 5.09E−03 |
| 1G1 | 3.44E−03 | 6C6 | 2.75E−02 | c-Met | 4.38E−03 |
| 1G5 | 3.78E−03 | 6D6 | 2.30E−04 | | |
| 1H8 | 3.37E−03 | 6E6 | 1.70E−03 | | |

Figure 3:
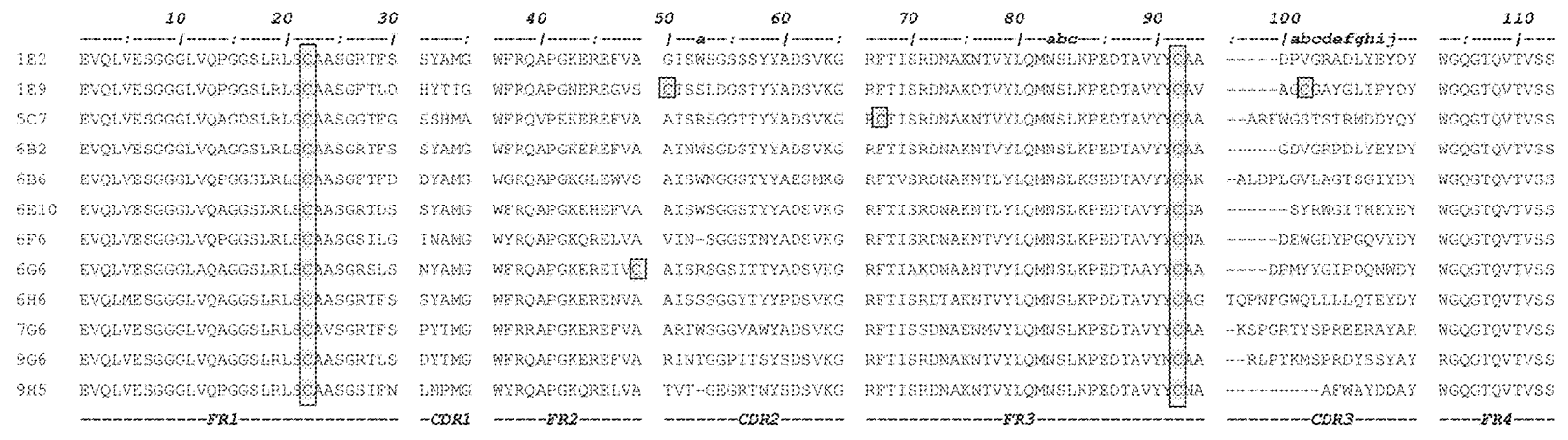

1.6 HGF-Inhibiting Nanobody Expression and Purification 12 inhibitors of the HGF/c-Met interaction were selected for further characterization. The aligned sequences are given in FIG. 3. Selected Nanobody inhibitors were expressed in the periplasmic space of E. coli as c-myc, His6-tagged proteins in a culture volume of 50 mL. Expression was induced by addition of 1 mM IPTG and allowed to continue for 4 h at 37° C. After spinning the cell cultures, periplasmic extracts were prepared by freeze-thawing the pellets. These extracts were used as starting material for immobilized metal affinity chromatography (IMAC). Nanobodies were eluted from the column with 250 mM imidazole and subsequently subjected to gel filtration to PBS. The purified Nanobody proteins were subsequently analyzed for purity and molecular weight on Coomassie-stained SDS-PAGE gels, run under reducing conditions (data not shown).

1.7 Affinity Determination of Nanobodies Binding HGF

Affinity constants ($K_d$) of individual purified Nanobody clones were determined by surface plasmon resonance on a Biacore T100 instrument essentially as described above. Kd, ka and kd values for HGF binding of selected Nanobody clones are summarized in Table 4. The average was taken of an analysis performed on R&D material and Peprotech material.

TABLE 4 kinetic and affinity constants of anti-HGF Nanobodies

| Clone | ka (1/Ms) | kd (1/s) | Kd (nM) |
|---|---|---|---|
| 1E2 | 7.52 (±0.55) * $10^4$ | 1.00 (±0.52) * $10^{-4}$ | 1.36 ± 0.78 |
| 6E10 | 4.99 (±0.55) * $10^4$ | 5.50 (±7.07) * $10^{-5}$ | 1.14 ± 1.59 |
| 6B2 | 2.78 (±0.45) * $10^4$ | 2.15 (±0.30) * $10^{-6}$ | 0.08 ± 0.02 |
| 1E9 | 9.20 (±5.95) * $10^4$ | 5.20 (±0.04) * $10^{-4}$ | 7.16 ± 4.59 |
| 6G6 | 7.53 (±0.66) * $10^5$ | 5.73 (±4.88) * $10^{-3}$ | 7.37 ± 5.85 |
| 7G6 | 1.06 (±0.24) * $10^6$ | 6.91 (±0.67) * $10^{-4}$ | 0.67 ± 0.09 |

The dissociation curves of some of the clones were bi-phasic. Therefore the dissociation curves were split into 2 parts ranging from 125 to 185 seconds and 300 to 720 seconds after the injection start. The fitted off-rates are respectively kd1 and kd2 and the corresponding values are given in Table 5.

TABLE 5 off-rates of anti-HGF Nanobodies which showed a heterogeneous dissociation profile

| Clone | kd1 (1/s) | kd2 (1/s) |
|---|---|---|
| 9H5 | 2.41 (±1.36) * $10^{-3}$ | 9.52 (±8.60) * $10^{-4}$ |
| 9G6 | 2.37 (±1.32) * $10^{-3}$ | 1.02 (±0.29) * $10^{-3}$ |
| 5C7 | 6.05 (±0.35) * $10^{-3}$ | 8.21 (±0.64) * $10^{-4}$ |
| 6H6 | 3.13 (±0.39) * $10^{-3}$ | 3.32 (±0.70) * $10^{-3}$ |
| 6F6 | 5.77 (±0.30) * $10^{-3}$ | 2.13 (±0.23) * $10^{-3}$ |

1.8 Inhibition of Human HGF/c-Met-Fc Interaction in AlphaScreen™

Figure 4:
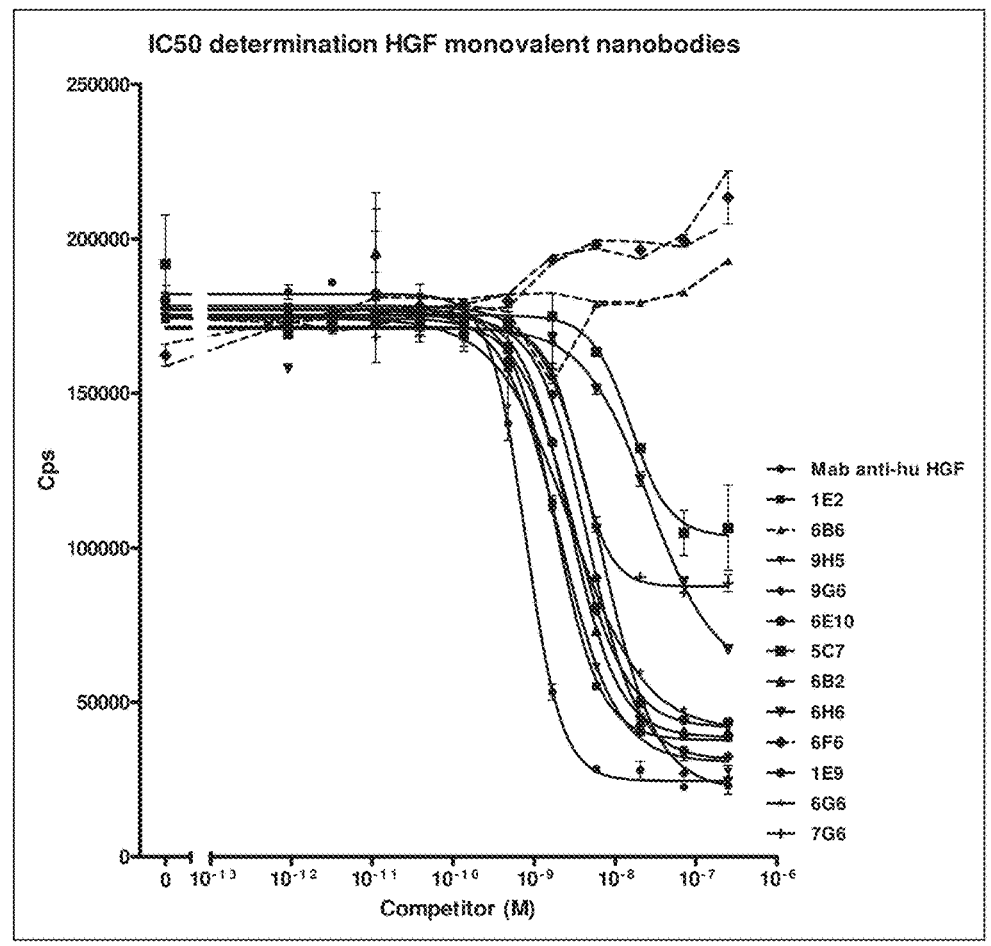
FIG. 4 IC50 determination using AlphaScreen™.

Serial dilutions of purified Nanobodies were then analyzed for their ability to block the interaction of human HGF with c-Met-Fc using the same AlphaScreen™ assay as described above (1.4). Representative data are shown in FIG. 4. At last 8 Nanobodies have been identified which inhibit the HGF/c-Met interaction with $IC_{50}$ values ranging from 1.8 nM-26.7 nM and bind to HGF with an affinity constant ranging from about 100 pM up to about 10 nM. Table 6 gives a summary of the obtained results on these 8 anti-HGF Nanobodies.

TABLE 6

Summary of obtained results on several anti-HGF candidates.

| Clone | IC50 (nM) | $K_d$ (nM) | kd ($s^{-1}$) |
|---|---|---|---|
| 1E2 | 1.8 | 1.36 ± 0.78 | 1 × 10e−4 |
| 9H5 | 2.1 | heterogeneous | 1 × 10e−3 |
| 9G6 | 6.6 | heterogeneous | 1 × 10e−3 |
| 6E10 | 3.0 | 1.14 ± 1.59 | 5 × 10e−5 |
| 6B2 | 2.8 | 0.08 ± 0.02 | 1 × 10e−5 |
| 6H6 | 26.7 | heterogeneous | 3 × 10e−3 |
| 1E9 | 4.5 | 7.16 ± 4.59 | 5 × 10e−4 |
| 6G6 | 2.8 | 7.37 ± 5.85 | 6 × 10e−3 |

1.9 Formatting Nanobodies of the Invention

To test whether selected Nanobodies have potential as anticancer agents, a strategy to increase the serum half-life is preferred (as for example described in patent application WO 04/041865), since the serum half-life of a mono- or bivalent Nanobody (approximately 15 or 30 KDa, respectively) is not optimal for this therapeutic indication.

Human serum albumin specific Nanobody ALB, cross reactive with mouse serum albumin, was chosen. Here we describe the construction of bispecific Nanobodies consisting of an anti-HGF Nanobody and a serum albumin binding immunoglobulin single variable domain (ALB), all separated by a 9 (GS) amino acid linker peptide and resulting in constructs 1E2-9GS-ALB and 6E10-9GS-ALB. Cloning was performed such that said Nanobodies are translationally fused at their C-terminus to an anti-human serum albumin (HSA) binding Nanobody (ALB), separated by a 9GS-linker (amino acid sequence GGGGSGGGS (SEQ ID NO:119). The constructs have an additional C-terminal 3×FLAG and His$_6$-tag (SEQ ID NO: 116).

1.10 Trispecifc Nanobodies of the Invention

Nanobodies 1E2-9GS-ALB-35GS-αEGFR, αEGFR-9GS-ALB-35GS-1E2, 6E10-9GS-ALB-35GS-αEGFR and αEGFR-9GS-ALB-35GS-6E10 are cloned into the same expression plasmid and fused to the same ALB Nanobody as described in Example 1.9, but such that the HGF binding Nanobodies are translationally fused at either their C-terminus or N-terminus to αEGFR Nanobodies, separated by the Alb8 Nanobody and a 35GS-linker. The αEGFR Nanobodies are described in WO 05/044858, WO 04/041867 and/or WO07/042289. As above, these constructs carry C-terminal 3×FLAG and His$_6$-tags.

Nanobodies 1E2-9GS-ALB-35GS-αVEGF, αVEGF-9GS-ALB-35GS-1E2, 6E10-9GS-ALB-35GS-αVEGF and αVEGF-9GS-ALB-35GS-6E10 are cloned into the same expression plasmid and fused to the same ALB Nanobody as described in Example 1.9, but such that the HGF binding Nanobodies are translationally fused at either their N-terminus or C-terminus to αVEGF Nanobodies, separated by the ALB Nanobody and a 35GS-linker. The αVEGF Nanobodies are described in WO 08/101985. As above, these constructs carry C-terminal 3×FLAG and Hiss-tags.

Example 2: α-HGF ISVDs in Tumor Therapy: Materials and Methods 2.1 Materials

All reagents where purchased from Sigma-Aldrich (St. Louis, Mo.) unless otherwise stated. With respect to the preparation of the $^{89}$Zr-labeled Nanobody constructs, no special measures were taken regarding working under strict metal-free conditions. Df-Bz-NCS was purchased from Macrocyclics (cat. No. B705). [$^{89}$Zr]Zr-oxalate in 1.0 M oxalic acid (≤0.15 GBq/nmol) was from IBA molecular (cf. www.iba.be/molecular).

2.2 Cell Line

The glioblastoma cell line U87 MG, which contains an autocrine HGF-loop, was obtained from the American Type Culture Collection (www.ATCC.com) and cultured in DMEM supplemented with 5% FBS. All cells were cultured at 37° C. with 5% $CO_2$.

2.3 Preparation of $^{89}$Zr-1E2-ALB and $^{89}$Zr-6E10-ALB

For preparation of the $^{89}$Zr conjugates, the $^{89}$Zr was coupled to the Nanobody by use of the bifunctional chelate p-isothiocyanatobenzyl desferrioxamine (Df-Bz-NCS), essentially as described by Vosjan et al., "Conjugation and radiolabeling of monoclonal antibodies with zirconium-89 for PET imaging using the bifunctional chelate p-isothiocyanatobenzyl-desferrioxamine" (Vosjan M J, Perk L R, Visser G W, Budde M, Jurek P, Kiefer G E, van Dongen G A. Nat Protoc. 2010; 5(4):739-43). In short, 1-2 mg αHGF-Nanobody was premodified with a 3-fold molar excess of Df-Bz-NCS. After PD-10 column purification the premodified Nanobody was labeled with $^{89}$Zr (37 MBq) in 0.25 M HEPES buffer pH 7.0 at room temperature in a total volume of 2 mL. The $^{89}$Zr-Df-Bz-NCS-Nanobody was purified by PD-10 column using 0.25 M NaOAc with 5 mg mL$^{-1}$ gentisic acid, pH 5.5, as eluent.

2.4 Quality Control of $^{89}$Zr-1E2-ALB and $^{89}$Zr-6E10-ALB

All radioactive conjugates were analyzed by instant thin layer chromatography (ITLC) to determine the labeling efficiency and radiochemical purity. The integrity of the Nanobody was analyzed by high performance liquid chromatography (HPLC) and sodium dodecyl sulphate-polyacrylamide gel electrophoresis (SDS-PAGE) followed by phosphor imaging (Storm820, GE Healthcare). Immunoreactivity was determined by a HGF-coated enzyme-linked immunosorbent assay essentially as described by Collingridge (Collingridge et al., "The development of [(124)I] iodinated-VG76e: a novel tracer for imaging vascular endothelial growth factor in vivo using positron emission tomography." Cancer Res 2002; 20:5912-9).

2.5 Biodistribution Study

The distribution of $^{89}$Zr-labeled αHGF-Nanobodies was examined in nude mice (HSD: Athymic Nude-Foxn1$^{nu}$, 20-30 g; Harlan Laboratories, Horst, The Netherlands) inoculated subcutaneously with 2×10$^6$ U87 MG cells at two lateral sides. All animal experiments were done according to NIH Principles of Laboratory Animal Care and Dutch national law ("Wet op de dierproeven", Stb 1985, 336). Mice bearing U87 MG xenografts (size ~100 mm$^3$) were injected with 0.37 MBq $^{89}$Zr-Df-Bz-NCS-1E2-ALB or 0.37 MBq $^{89}$Zr-Df-Bz-NCS-6E10-ALB via the retro-orbital plexus. Unlabeled Nanobody was added to the injection mixture to obtain a final dose of 30 μg per mouse. At 1, 2, 3 or 7 days post injection (p.i.) five mice per group were anesthetized, bled, killed and dissected. Blood, tumor and normal tissues were weighed and radioactivity was measured in a gamma counter (Wallac, Turku, Finland). Radioactivity uptake for each sample was calculated as the percentage of the injected dose per gram of tissue (% ID/g).

In addition, a Nanobody dose-diminishing study was performed. To this end, 5, 10, 20 and 30 μg of $^{89}$Zr-labeled 1E2-ALB (0.23-0.83 MBq) was injected in mice bearing U87 MG xenografts, at 3 days p.i. 5 mice per group were examined as described above.

2.6 Blood Kinetics in Mice

Blood concentrations of αHGF-Nanobodies were examined in two groups of two mice. One group of tumor-bearing mice received 0.37 MBq $^{89}$Zr-1E2-ALB (30 μg) while the other group received 0.37 MBq $^{89}$Zr-6E10-ALB (30 μg). Blood was collected at 1 and 3 h, and at 1, 2, 3 and 7 days p.i. by tail laceration and radioactivity was measured in a gamma counter. Radioactivity for each sample was calculated as the percentage of the injected dose per gram of blood (% ID/g).

2.7 Therapy Study

The therapeutic effectiveness of the αHGF-Nanobodies was studied in the same nude mice model as described for the biodistribution study.

To this end, 7 groups of 6 mice with established U87 MG xenografts were evaluated. At the start of this study mean tumor size was ~100 mm$^3$, and was similar for the different treatment groups. All mice received i.p. treatment 3 times a week for 5 weeks. Group 1 was the control group and received 200 μl of saline solution per dose. Group 2, 3 and 4, received 10, 30 and 100 μg of Nanobody 1E2-ALB, respectively. Group 5, 6 and 7 received 10, 30 and 100 μg of Nanobody 6E10-ALB, respectively. Body weight and tumor volume were measured 3 times a week up to 70 days after end of treatment.

2.8 Statistical Analysis

Biodistribution and therapy experiments were statistically analyzed using SPSS 15.0 software. Differences in tissue uptake between injected conjugates as well as differences in average tumor volume between the various treatment groups were statistically analyzed for each different time point using Student t-test for unpaired data. Survival was calculated using Kaplan-Meier curves. Two-sided significance levels were calculated and P<0.05 was considered statistically significant.

Example 3: Radiolabeling and Quality Control of $^{89}$Zr-1E2-ALB and $^{89}$Zr-6E10-ALB Labeling of both Nanobodies with $^{89}$Zr resulted in overall labeling yields of 75-90%, after PD-10 column purification. Radiochemical purity was always >97% as determined with ITLC and confirmed with HPLC. Integrity of the Nanobodies was optimal as determined by HPLC and SDS-PAGE. Immunoreactivity of $^{89}$Zr-1E2-ALB and $^{89}$Zr-6E10-ALB was determined by HGF-coated ELISA and was similar to that of the reference $^{131}$I-labeled αHGF-Nanobodies (~50%).

Example 4: Biodistribution Study

Figure 5A:
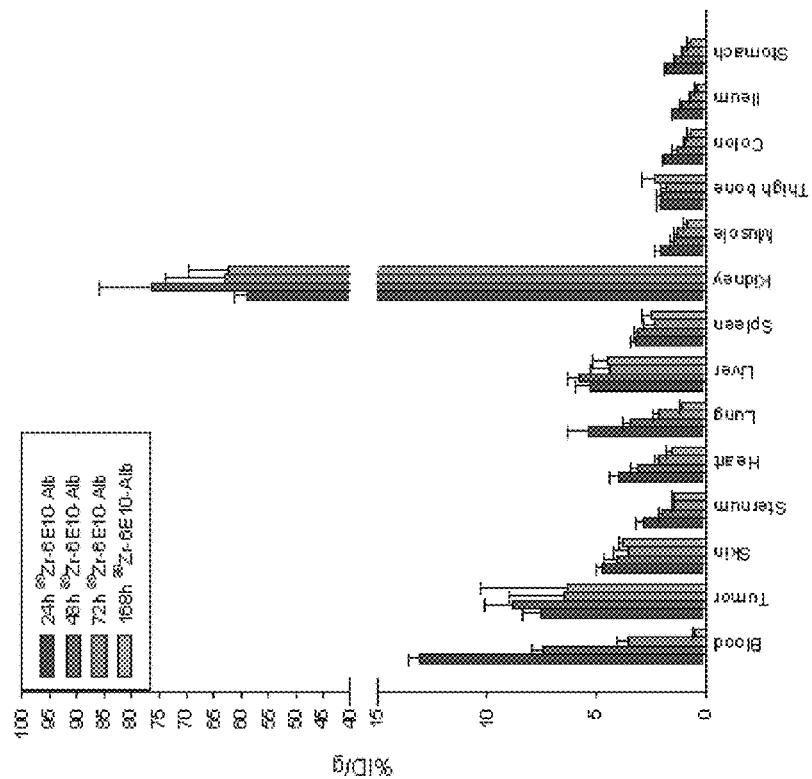
FIGS. 5A-5B Biodistribution of αHGF Nanobodies $^{89}$Zr-1E2-ALB (FIG. 5A) and $^{89}$Zr-6E10-ALB (FIG. 5B) in nude mice bearing U87 MG xenografts at 24, 48, 72 and 168 h p.i.
Figure 5B:
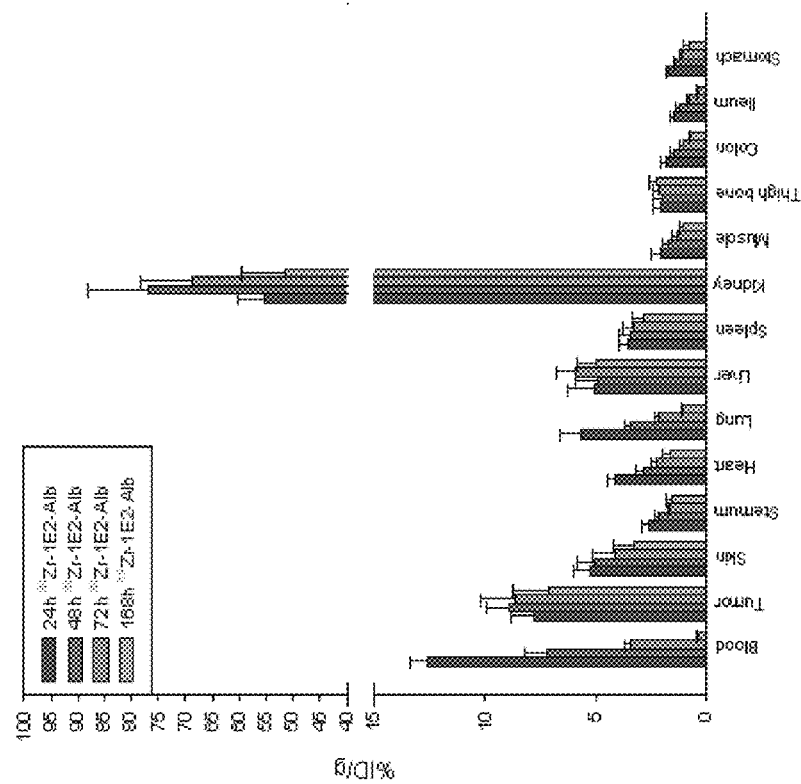

For biodistribution, studies nude mice bearing U87 MG xenografts were injected with either 0.39±0.01 MBq $^{89}$Zr-1E2-ALB or 0.37±0.01 MBq $^{89}$Zr-6E10-ALB. Biodistribution at 1, 2, 3, or 7 days p.i. is shown in FIGS. 5A-5B. Both α-HGF-Nanobodies showed similar biodistributions with selective tumor uptake; no significant differences were observed (P>0.01). While blood levels gradually decreased over time, tumor uptake remained relatively stable. Blood levels were 12.6±0.7, 7.2±1.0, 3.4±0.3, and 0.3±0.1% ID/g for $^{89}$Zr-1E2-ALB and 13.1±0.6, 7.4±0.6, 3.5±0.5, and 0.5±0.1% ID/g for $^{89}$Zr-6E10-ALB at 1, 2, 3, and 7 days p.i., respectively. Tumor uptake at these time points was 7.8±1.1, 8.9±1.0, 8.7±1.5, and 7.2±1.6% ID/g for $^{89}$Zr-1E2-ALB, and 7.5±0.8, 8.8±1.3, 6.5±2.5, and 6.3±4.0% ID/g at 1, 2, 3, and 7 days p.i., respectively for $^{89}$Zr-6E10-ALB. Tumor uptake was higher than in normal organs, except for kidneys. The latter is typical for small proteins, which are rapidly cleared via the kidneys.

Example 5: Dose-Diminishing Study

Figure 6:
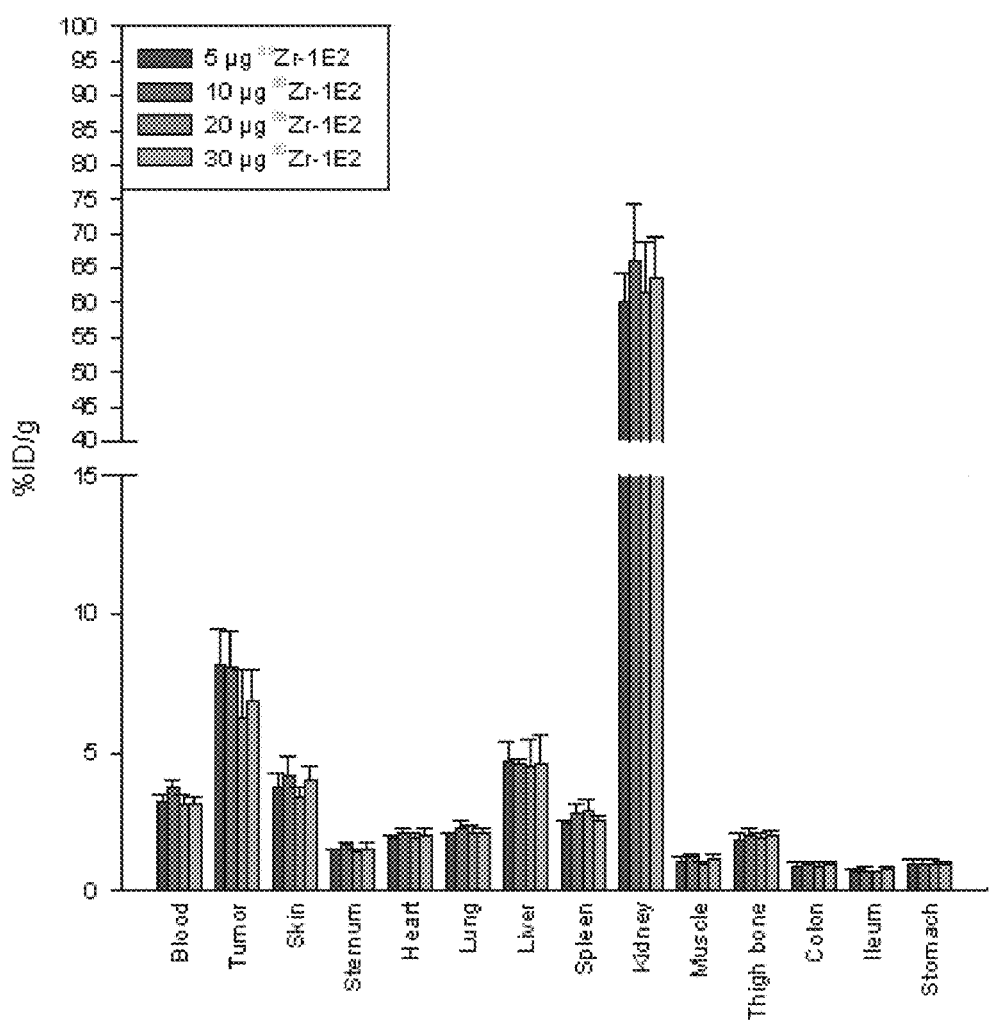
FIG. 6 Biodistribution of αHGF Nanobody 1E2-ALB labeled with the residualizing PET isotope $^{89}$Zr or the non residualizing radio isotope $^{131}$I, in nude mice bearing U87 MG xenografts at 72 h p.i.

A dose-diminishing study was performed with $^{89}$Zr-1E2-ALB to determine the optimal Nanobody dose for in vivo imaging. Nude mice bearing U87 MG xenografts were injected with 0.32±0.01, 0.47±0.01, 0.47±0.01, or 0.83±0.01 MBq $^{89}$Zr-1E2-ALB, containing 5, 10, 20 or 30 µg 1E2-ALB, respectively. Three days p.i. similar biodistribution was seen for all dose groups (FIG. 6). No significant differences were observed in tumor uptake, being 8.2±1.2, 8.1±1.3, 6.3±1.7, 6.9±1.1% ID/g for the 5, 10, 20, and 30 µg dose groups, respectively. High uptake in kidneys was observed for all dose groups. Also no significant differences were observed between the different dose groups (P>0.01).

Example 6: Blood Kinetics in Mice

Figure 7:
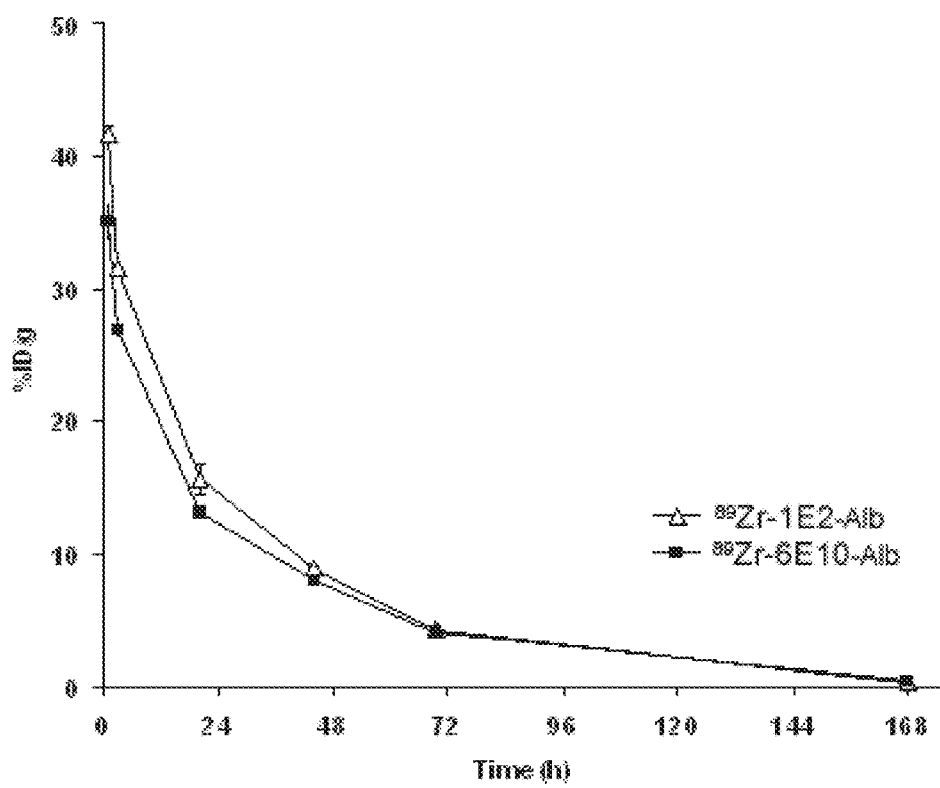
FIG. 7 Bloodkinetics of $^{89}$Zr labeled αHGF Nanobodies.

Blood kinetics of 0.39±0.01 MBq $^{89}$Zr-1E2-ALB (30 µg) and 0.37±0.01 MBq $^{89}$Zr-6E10-ALB (30 µg) appeared to be similar (FIG. 7). Blood levels of Nanobody constructs were 41.7±0.6 and 35.1±1.48% ID/g 1 h after injection, for $^{89}$Zr-1E2-ALB and $^{89}$Zr-6E10-ALB, respectively. This slowly decreased from 4.3±0.1 to 0.3±0.1% ID/g between 72 and 168 h p.i. for $^{89}$Zr-1E2-ALB and from 4.2±0.1 to 0.5±0.1% ID/g for $^{89}$Zr-6E10-ALB.

Example 7: Therapy Study

Figure 8A:
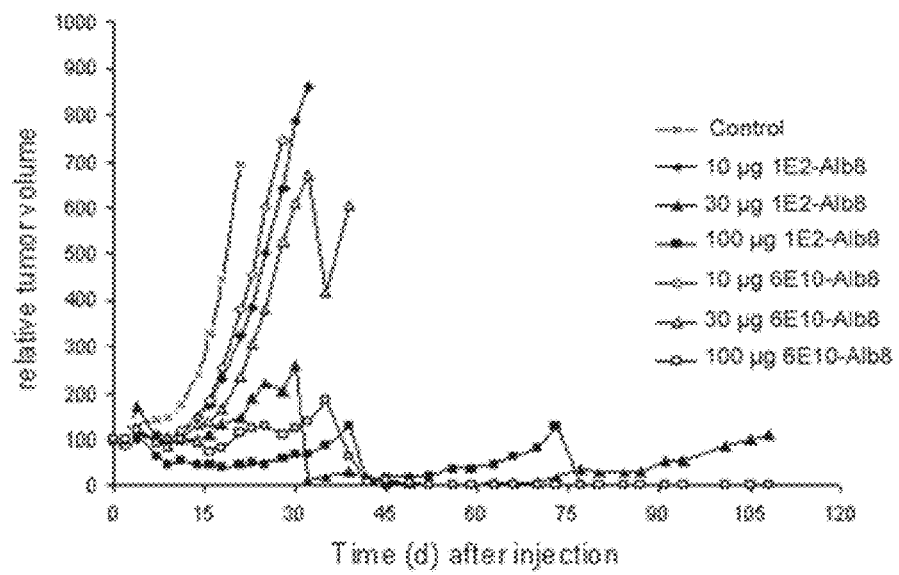
Figure 8B:
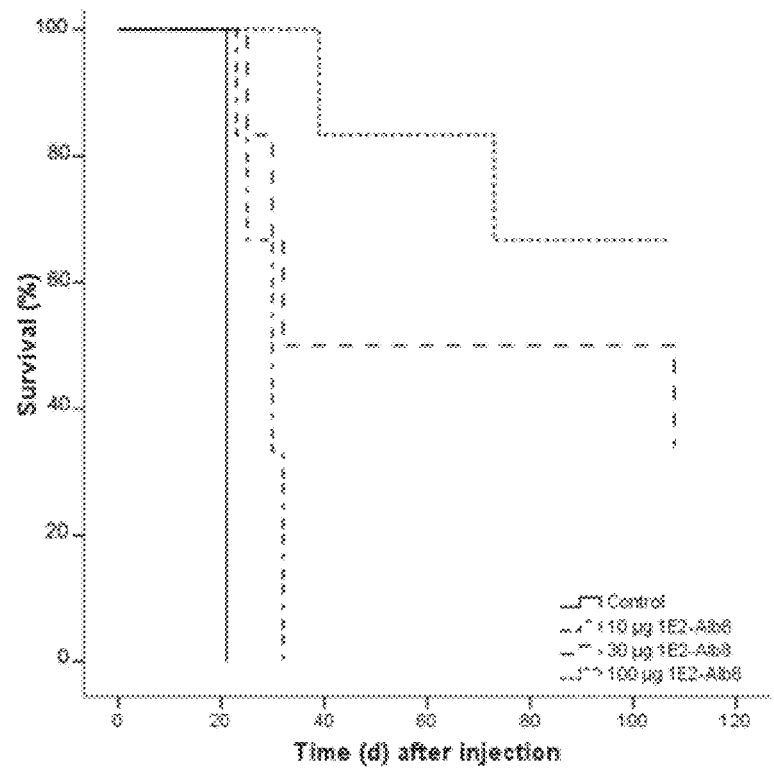

Mice who received Nanobodies showed tumor growth delay in comparison to the control PBS-group (group 1) (FIG. 8A). Within the treatment schedule of 35 days all control mice were sacrificed due to the large volumes of the tumors. Mice who received α-HGF-Nanobodies responded to treatment; mice who received the lowest dose (group 2 and 5; 10 µg) had minimal benefit while the highest dose groups (group 4 and 7; 100 µg) showed significant tumor growth delay with 4 out of 6 mice (7 out of 11 tumors) being cured in group 4 (1E2-ALB), and 3 out of 6 mice (6 out of 11 tumors) being cured in group 7 (6E10-ALB). In the intermediate dose groups, no cures were observed in group 6 (6E10-ALB), while 3 out of 6 mice (5 out of 11 tumors) were cured in group 3 (1E2-ALB) (FIG. 8B).

At the end of treatment (day 35), only mice in the intermediate and highest dose groups were alive, and followed till day 108 after start of treatment. At the end of the study 4 out of 6 mice (66%) were cured in group 4 (100 µg 1E2-ALB), and 3 out of 6 mice (50%) in group 7 (100 µg 6E10-ALB), while 2 out of 6 mice (33%) were cured in group 3 (30 µg 1E2-ALB). In contrast, all mice in group 5 (30 µg 6E10-ALB) faced re-growth of tumors during follow up (FIG. 8C).

Example 8: Comparison with Contemporaneous Anti-HGF Antibodies

In 2001, Cao et al. (Proc Natl Acad Sci USA 2001; 98:7443-8) reported the first in vivo results with monoclonal antibodies that bind to HGF. A mixture of 3 antibodies (200 µg/mouse every day until day 20) was injected in mice, which were injected one day before start of therapy with C-127 cells or U118 cells. All mice showed growth inhibition as compared to the control groups. In an established U118 tumor model, mice received a mixture of A-1 and A-7 3 times a week for 10 weeks, tumor growth delay was seen. Cao et al. needed a combination of 3 monoclonal antibodies to achieve neutralizing activity to HGF in glioma xenograft tumors, and suggested that the complex heterodimeric structure of HGF makes it necessary to simultaneously target multiple HGF epitopes by combining mAbs. Moreover, no cures were observed.

AMG102 (rilotumumab; Amgen, Inc.) was identified in an extensive screen, resulting in 3 potential candidates, of which each recognized a different epitope. Although AMG102 had intermediate affinity for HGF [as judged by binding affinity], it was the only mAb identified that completely blocked the binding of HGF to c-Met (Kim et al. 2006 Clin Cancer Res 12:1292-1298). Nevertheless, Schöffski and colleagues demonstrated that no significant growth inhibition occurred with AMG102 in metastatic renal cell carcinoma (Schöffski et al. 2010 BJU Int doi:10.1111/j.1464). Similarly, HGF and its receptor c-Met have been implicated in the pathogenesis of glioblastoma (GBM), but Wen and colleagues showed in a phase II study that AMG102 monotherapy treatment at doses up to 20 mg/kg was not associated with significant antitumor activity in the selected patient groups (Wen et al. 2011 Neuro-Oncology doi:10.1093/neuonc/noq198). Hence, merely blocking the binding of HGF to c-Met does not warrant tumor inhibition.

The monoclonal antibody AV-299 (also known as SCH900105), which is developed by Aveo pharmaceuticals/Schering Plough, is not published in any peer reviewed journal, but only discussed on posters. No substantive information is available of AV-299, such as its sequence. Nevertheless, the information on these posters is not consistent.

It can be concluded that the monovalent Nanobodies of the present invention outperform the contemporaneous monoclonal antibodies, which are bivalent.

Example 9: In Vitro Efficacy of Nanobodies 1E2 and 6E10 Against HGF-Driven Proliferation in Multiple Myeloma Cell Lines The in vitro efficacy of Nanobodies 1E2 and 6E10 on HGF induced proliferation is assessed in c-Met positive human multiple myeloma cells. Both HGF autocrine (ANBL-6) as well as paracrine (INA-6, IH-1 and OH-2) multiple myeloma cell lines are analyzed according to Hov et al. (Hov et al. 2004; Clin Cancer Res 10, 6686-6694; and Hov et al., 2009; Eur J Haematology 82, 277-287).

Example 10: Analysis of Efficacy of Trispecific HGF/EGFR Nanobodies on PI3K Signaling The c-Met as well as the EGFR can signal via the PI3K pathway which conveys mitogenic signals. To demonstrate simultaneous targeting of the EGFR and c-Met receptor phosphorylation of AKT, a downstream target in the PI3K pathway, can be monitored. To this end, unstimulated cells, cells treated with EGF or HGF or cells treated with both cytokines are in parallel incubated with unspecific, parental control or bispecific Nanobodies, Nanobodies 1E2 and 6E10 are each coupled to Nanobodies inhibiting EGFR as described in Example 1.10. Alternatively, one can also assess cells which overexpress EGFR and/or have an autocrine HGF loop which activates c-Met signaling. AKT is a major downstream signaling component of the PI3K pathway and phosphorylation of this protein is a key indicator of signaling via this pathway.

Example 11: Analysis of Efficacy of Trispecific HGF/EGFR Nanobodies on MAPK Signaling EGFR and c-Met receptor can signal via the MAPK pathway. To demonstrate targeting of the EGFR and c-Met receptor, phosphorylation of ERK1/2, a major downstream target in the MAPK pathway, can be monitored. To this end, unstimulated cells, cells treated with EGF or HGF or cells treated with both cytokines are in parallel incubated with unspecific, monospecific, or bispecific Nanobodies essentially according to Example 1.10. Alternatively, one can also assess cells which overexpress EGFR and/or have an autocrine HGF loop which activates c-Met signaling.

Example 12: Analysis of Efficacy of Trispecific HGF/EGFR Nanobodies on Inhibiting Proliferation A431 cells display high cell surface levels of EGFR and medium high cell surface expression of c-Met as was independently confirmed in others studies.

Inhibition of A431 proliferation by bispecific HGF/EGFR Nanobodies essentially according to Example 1.10 can be measured in CellTiterGlow™ assay after 48 hours.

Example 13: In Vitro Analysis of Migration of Cells after Treatment with Trispecific Nanobodies Active c-Met signaling is involved in cell migration and invasion. Efficacy of the trispecific Nanobody can be determined by measuring inhibition of HGF-induced migration. For this purpose, the HGF-inducible cell line A549 is treated with HGF in the presence or absence of the bispecific Nanobody, monospecific Nanobodies against HGF and inhibitors of EGFR. Alternatively, the migration of cells through an 8 µm pore is measured in a time dependent manner on an Acea Real Time analyzer using CIM-plates as a read out.

Example 14: Analysis of Efficacy of Trispecific HGF/VEGF Nanobodies in a KP4 Pancreatic Xenograft Tumor Model KP4 cells are cultured in growth media that consists of RPMI 1640 media (Invitrogen), 2 mM L-glutamine, and 10% fetal bovine serum. To prepare cells for inoculation into mice, cells are trypsinized and subsequently washed with ten milliliters of sterile IX phosphate buffered saline (PBS). A subset of cells is counted by trypan blue exclusion and the remainder of cells is resuspended in 100 µl of sterile IX PBS to a concentration of $5 \times 10^7$ cells per milliliter. Mice are inoculated subcutaneously in the right sub-scapular region with $5 \times 10^6$ KP4 cells. Tumors are monitored until they reach a mean volume of 230 mm.

Mice are randomized into 5 groups of ten mice each and treatment is initiated. Mice in Group 1 are treated with monospecific HGF Nanobody. Mice in Group 2 are treated with monospecific αVEGF Nanobody. Mice in Group 3 are treated with a trispecific HGF/αVEGF Nanobody essentially according to Example 1.10. Mice in Group 4 are treated with a monospecific αVEGF Nanobody as well as a monospecific HGF Nanobody. Mice in Group 5 are treated with a negative control (unrelated Nanobody). Tumor volumes are measured twice per week and animals are monitored for 25 days.

Example 15: Analysis of Efficacy of Trispecific HGF/αVEGF Nanobodies in a NSCLC Xenograft Tumor Model Human NSCLC cells (A549, DSMZ, Braunschweig, Germany) are cultured in growth media that consists of RPMI 1640 media (Invitrogen), 2 mM L-glutamine, and 10% fetal bovine serum. To prepare cells for inoculation into mice, cells are trypsinized and subsequently washed with ten milliliters of sterile IX phosphate buffered saline (PBS). A subset of cells is counted by trypan blue exclusion and the remainder of cells is resuspended in 100 µl of sterile IX PBS to a concentration of $5 \times 10^7$ cells per milliliter. Mice are inoculated subcutaneously in the right sub-scapular region with $5 \times 10^6$ human A549 cells. Tumors are monitored until they reach a mean volume of 200 mm.

Mice are randomized into 5 groups of ten mice each and treatment is initiated. Mice in Group 1 are treated with monospecific HGF Nanobody according to the invention. Mice in Group 2 are treated with monospecific αVEGF Nanobody. Mice in Group 3 are treated with a trispecific HGF/αVEGF Nanobody essentially according to Example 1.10. Mice in Group 4 are treated with a monospecific αVEGF Nanobody as well as a monospecific HGF Nanobody according to the invention. Mice in Group 5 are treated with a negative control (unrelated Nanobody). Tumor volumes are measured twice per week and animals are monitored for 25 days.

Example 16: Analysis of Efficacy of Tetraspecific HGF/VEGF/EGFR Nanobodies in a NSCLC Xenograft Tumor Model Human NSCLC cells (A549, DSMZ, Braunschweig, Germany) are cultured in growth media that consists of RPMI 1640 media (Invitrogen), 2 mM L-glutamine, and 10% fetal bovine serum. To prepare cells for inoculation into mice, cells are trypsinized and subsequently washed with ten milliliters of sterile IX phosphate buffered saline (PBS). A subset of cells is counted by trypan blue exclusion and the remainder of cells is resuspended in 100 µl of sterile IX PBS to a concentration of $5 \times 10^7$ cells per milliliter. Mice are inoculated subcutaneously in the right sub-scapular region with $5 \times 10^6$ human A549 cells. Tumors are monitored until they reach a mean volume of 200 mm.

Mice are randomized into 6 groups of ten mice each and treatment is initiated. Mice in Group 1 are treated with a monospecific HGF Nanobody according to the invention. Mice in Group 2 are treated with monospecific αVEGF Nanobody. Mice in Group 3 are treated with a monospecific αEGFR Nanobody. Mice in Group 4 are treated with a monospecific αVEGF Nanobody, a monospecific αEGFR Nanobody as well as a monospecific HGF Nanobody according to the invention. Mice in Group 5 are treated with a tetraspecific HGF/αVEGF/αEGFR/ALB Nanobody. Mice in Group 6 are treated with a negative control (unrelated Nanobody). Tumor volumes are measured twice per week and animals are monitored for 25 days.

Sequence Tables:

TABLE B-1

Prior art sequences

| Name | SEQ ID NO | Amino acid sequences |
|---|---|---|
| human HGF (hHGF) | 1 | MWVTKLLPALLLQHVLLHLLLLPIAIPYAEGQRKRRNTIHEFKKSAKT TLIKIDPALKIKTKKVNTADQCANRCTRNKGLPFTCKAFVFDKARKQC LWFPFNSMSSGVKKEFGHEFDLYENKDYIRNCIIHRHKFLPERYPDKG FDDETTECIQGQGEGYRGTVNTIWNGIPCQRWDSQYPHEHDMTPENFK CKDLRENYCRNPDGSESPWCFTTDPNIRVGYCSQIPNCDMSHGQDCYR GNGKNYMGNLSQTRSGLTCSMWDKNMEDLHRHIFWEPDASKLNENYCR NPDDDAHGPWCYTGNPLIPWDYCPISRCEGDTTPTIVNLDHPVISCAK TKQLRVVNGIPTRTNIGWMVSLRYRNKHICGGSLIKESWVLTARQCFP SRDLKDYEAWLGIHDVHGRGDEKCKQVLNVSQLVYGPEGSDLVLMKLA RPAVLDDFVSTIDLPNYGCTIPEKTSCSVYGWGYTGLINYDGLLRVAH LYIMGNEKCSQHHRGKVTLNESEICAGAEKIGSGPCEGDYGGPLVCEQ HKMRMVLGVIVPGRGCAIPNRPGIFVRVAYYAKWIHKIILTYKVPQSN YCRNPDGQPRPWCYTLDPHTRWEYCAIKTCADNTMNDTDVPLGKGRSY KGTVRGEEGGPWCFTSNPEVRYEVCDIPQCSEVECMTCNGESYRGLMD HTESGHICQRWDHQTPSITKSGIKCQPWSSMIPHEHSFLPSSYRGKDL QENYCRNP |
| rec-hHGF (Peprotech) | 2 | QRKRRNTIHEFKKSAKTTLIKIDPALKIKTKKVNTADQCANRCTRNKG LPFTCKAFVFDKARKQCLWFPFNSMSSGVKKEFGHEFDLYENKDYIRN CIIGKGRSYKGTVSITKSGIKCQPWSSMIPHEHSFLPSSYRGKDLQEN YCRNPRGEEGGPWCFTSNPEVRYEVCDIPQCSEVECMTCNGESYRGLM DHTESGKICQRWDHQTPHRHKFLPERYPDKGFDDNYCRNPDGQPRPWC YTLDPHTRWEYCAIKTCADNTMNDTDVPLETTECIQGQGEGYRGTVNT IWNGIPCQRWDSQYPHEHDMTPENFKCKDLRENYCRNPDGSESPWCFT TDPNIRVGYCSQIPNCDMSHGQDCYRGNGKNYMGNLSQTRSGLTCSMW DKNMEDLHRHIFWEPDASKLNENYCRNPDDDAHGPWCYTGNPLIPWDY CPISRCEGDTTPTIVNLDHPVISCAKTKQLRVVNGIPTRTNIGWMVSL RYRNKHICGGSLIKESWVLTARQCFPSRDLKDYEAWLGIHDVHGRGDE KCKQVLNVSQLVYGPEGSDLVLMKLARPAVLDDFVSTIDLPNYGCTIP EKTSCSVYGWGYTGLINYDGLLRVAHLYIMGNEKCSQHHRGKVTLNES EICAGAEKIGSGPCEGDYGGPLVCEQHKMRMVLGVIVPGRGCAIPNRP GIFVRVAYYAKWIHKIILTYKVPQS |
| rec hHGF (R & D systems) | 3 | QRKRRNTIHEFKKSAKTTLIKIDPALKIKTKKVNTADQCANRCTRNKG LPFTCKAFVFDKARKQCLWFPFNSMSSGVKKEFGHEFDLYENKDYIRN CIIGKGRSYKGTVSITKSGIKCQPWSSMIPHEHSFLPSSYRGKDLQEN YCRNPRGEEGGPWCFTSNPEVRYEVCDIPQCSEVECMTCNGESYRGLM DHTESGKICQRWDHQTPHRHKFLPERYPDKGFDDNYCRNPDGQPRPWC YTLDPHTRWEYCAIKTCADNTMNDTDVPLETTECIQGQGEGYRGTVNT IWNGIPCQRWDSQYPHEHDMTPENFKCKDLRENYCRNPDGSESPWCFT TDPNIRVGYCSQIPNCDMSHGQDCYRGNGKNYMGNLSQTRSGLTCSMW DKNMEDLHRHIFWEPDASKLNENYCRNPDDDAHGPWCYTGNPLIPWDY CPISRCEGDTTPTIVNLDHPVISCAKTKQLRVVNGIPTRTNIGWMVSL RYRNKHICGGSLIKESWVLTARQCFPSRDLKDYEAWLGIHDVHGRGDE KCKQVLNVSQLVYGPEGSDLVLMKLARPAVLDDFVSTIDLPNYGCTIP EKTSCSVYGWGYTGLINYDGLLRVAHLYIMGNEKCSQHHRGKVTLNES EICAGAEKIGSGPCEGDYGGPLVCEQHKMRMVLGVIVPGRGCAIPNRP GIFVRVAYYAKWIHKIILTYKVPQS |
| Human c-Met or hc-Met | 4 | MKAPAVLAPGILVLLFTLVQRSNGECKEALAKSEMNVNMKYQLPNFTA ETPIQNVILHEHHIFLGATNYIYVLNEEDLQKVAEYKTGPVLEHPDCF PCQDCSSKANLSGGVWKDNINMALVVDTYYDDQLISCGSVNRGTCQRH VFPHNGTADIQSEVGICFSPQIEEPSQCPDCVVSALGAKVLSSVKDRF INFFVGNTINSSYFPDHPLHSISVRRLKETKDGFMFLTDQSYIDVLPE FRDSYPIKYVHAFESNNFIYFLTVQRETLDAQTFHTRIIRFCSINSGL HSYMEMPLECILTEKRKKRSTKKEVFNILQAAYVSKPGAQLARQIGAS LNDDILFGVFAQSKPDSAEPMDRSAMCAFPIKYVNDFFNKIVNKNNVR CLQHFYGPNHEHCFNRTLLRNSSGCEARRDEYRTEFTTALQRVDLFMG QFSEVLLTSISTFIKGDLTIANLGTSEGRFMQVVVSRSGPSTPHVNFL LDSHPVSPEVIVEHTLNQNGYTLVITGKKITKIPLNGLGCRHFQSCSQ CLSAPPFVQCGWCHDKCVRSEECLSGTWTQQICLPAIYKVFPNSAPLE GGTRLTICGWDEGFRRNNKFDLKKTRVLLGNESCTLTLSESTMNTLKC TVGPAMNKHFNMSIIISNGHGTTQYSTFSYVDPVITSISPKYGPMAGG TLLTLTGNYLNSGNSRHISIGGKTCTLKSVSNSILECYTPAQTISTEF AVKLKIDLANRETSIFSYREDPIVYEIHPTKSFISGGSTITGVGKNLN SVSVPRMVINVHEAGRNFTVACQHRSNSEIICCTTPSLQQLNLQLPLK TKAFFMLDGILSKYFDLIYVHNPVFKPFEKPVMISMGNENVLEIKGND IDPEAVKGEVLKVGNKSCENIHLHSEAVLCTVPNDLLKLNSELNIEWK QAISSTVLGKVIVQPDQNFTGLIAGVVSISTALLLLLGFFLWLKKRKQ IKDLGSELVRYDARVHTPHLDRLVSARSVSPTTEMVSNESVDYRATFP EDQFPNSSQNGSCRQVQYPLTDMSPILTSGDSDISSPLLQNTVHIDLS ALNPELVQAVQHVVIGPSSLIVHFNEVIGRGHFGCVYHGTLLDNDGKK |

TABLE B-1-continued

Prior art sequences

| Name | SEQ ID NO | Amino acid sequences |
|---|---|---|
| | | IHCAVKSLNRITDIGEVSQFLTEGIIINKDFSHPNVLSLLGICLRSEGS PLVVLPYMKHGDLRNFIRNETHNPTVKDLIGFGLQVAKGMKYLASKKF VHRDLAARNCMLDEKFTVKVADFGLARDMYDKEYYSVHNKTGAKLPVK WMALESLQTQKFTTKSDVWSFGVLLWELMTRGAPPYPDVNTFDITVYL LQGRRLLQPEYCPDPLYEVMLKCWHPKAEMRPSFSELVSRISAIFSTF IGEHYVHVNATYVNVKCVAPYPSLLSSEDNADDEVDTRPASFWETS |
| recombinant human c-Met/Fc chimera (R & D systems) | 5 | ECKEALAKSEMNVNMKYQLPNFTAETPIQNVILHEHHIFLGATNYIYV LNEEDLQKVAEYKTGPVLEHPDCFPCQDCSSKANLSGGVWKDNINMAL VVDTYYDDQLISCGSVNRGTCQRHVEPHNHTADIQSEVHCIFSPQIEE PSQCPDCVVSALGAKVLSSVKDRFINFFVGNTINSSYFPDHPLHSISV RRLKETKDGFMFLTDQSYIDVLPEFRDSYPIKYVHAFESNNFIYFLTV QRETLDAQTFHTRIIRFCSINSGLHSYMEMPLECILTEKRKKRSTKKE VFNILQAAYVSKPGAQLARQIGASLNDDILFGVFAQSKPDSAEPMDRS AMCAFPIKYVNDFFNKINNKNNVRCLQHFYGPNHEHCFNRTLLRNSSG CEARRDEYRTEFTTALQRVDLFMGQFSEVLLTSISTFIKGDLTIANLG TSEGRFMQVVVSRSGPSTPHVNFLLDSHPVSPEVIVEHTLNQNGYTLV ITGKKITKIPLNGLGCRHFQSCSQCLSAPPFVQCGWCHDKCVRSEECL SGTWTQQICLPAIYKVFPNSAPLEGGTRLTICGWDFGFRRNNKFDLKK TRVLLGNESCTLTLSESTMNTLKCTVGPAMNKHFNMSIIISNGHGTTQ YSTFSYVDPVITSISPKYGPMAGGTLLTLTGNYLNSGNSRHISIGKKT CTLKSVSNSILECYTPAQTISTEFAVKLKIDLANRETSIFSYREDPIV YEIHPTKSFISGGSTITGVGKNLNSVSVPRMVINVHEAGRNFTVACQH RSNSEIICCTTPSLQQLNLQLPLKTKAFFMLDGILSKYFDLIYVHNPV FKPFEKPVMISMGNENVLEIKGNDIDPEAVKGEVLKVGNKSCENIHLH SEAVLCTVPNDLLKLNSELNIEWKQAISSTVLGKVIVQPDQNFIHIEG RMDPKSCDKTHTCPPCPAPELLGGPSVFLFPPKPKDTLMISRTPEVTC VVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSLSPGKHHHHHH |
| Alb11 | 114 | EVQLVESGGGLVQPGNSLRLSCAASGFTFSSFGMSWVRQAPGKGLEVA SSISGSGSDTLYADSVKGRFTISRDNAKTTLYLQMNSLRPEDTAVYYC TIGGSLSRSSQGTLVTVSS |
| Alb8 | 115 | EVQLVESGGGLVQPGNSLRLSCAASGFTFSSFGMSWVRQAPGKGLEWV SSISGSGSDTLYADSVKGRFTISRDNAKTTLYLQMNSLRPEDTAVYYC TIGGSLSRSSQGTLVTVSSAAAEQKLISEEDLNGAAHHHHHH |
| Tag-1 or 3xFLAG-His$_6$ | 116 | GAADYKDHDGDYKDHDIDYKDDDDKGAAHHHHHH |

TABLE B-2

Sequences for CDRs and frameworks, plus preferred combinations as provided in for formula I, i.e. FR1-CDR1-FR2-CDR2-FR3-CDR3-FR4 (the following terms: "ID" refers to the given SEQ ID NO. Preferred combinations of FR and CDR sequences for each Nanobody construct are used interchangeably throughout the application)

| Clone* | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 1E2: | 7 | EVQLVESGGGLVQPG GSLRLSCAASGRTFS | 28 | SYAMG | 40 | WFRQAPG KEREFVA | 52 | GISWSGSSS YYADSVKG | 64 | RFTISRDNAKNTVYLQ MNSLKPEDTAVYYCAA | 76 | DPVGRADLY EYDY | 88 | WGQGTQ VTVSS | 100 |
| 1E9: | 8 | EVQLVESGGGLVQPG GSLRLSCAASGFTLD | 29 | HYTIG | 41 | WFRQAPG NEREGVS | 53 | CISSLDGST YYADSVKG | 65 | RFTISRDNAKDTVYLQ MNSLKPEDTAVYYCAV | 77 | AGCGAYGLI PYDY | 89 | WGQGTQ VTVSS | 101 |
| 5C7: | 10 | EVQLVESGGGLVQAG DSLRLSCAASGGTFG | 30 | SSHMA | 42 | WFRQVPE KEREFVA | 54 | AISRSGGTT YYADSVKG | 66 | RCTISRDNAKNTVYLQ MNSLKPEDTAVYYCAA | 78 | ARFWGSTST RMDDYQY | 90 | WGQGTQ VTVSS | 102 |
| 6B2: | 15 | EVQLVESGGGLVQAG GSLRLSCAASGRTFS | 31 | SYAMG | 43 | WFRQAPG KEREFVA | 55 | AINWSGDST YYADSVKG | 67 | RFTISRDNAKNTVYLQ MNSLKPEDTAVYYCAA | 79 | GDVGRPDLY EYDY | 91 | WGQGTQ VTVSS | 103 |
| 6B6: | 16 | EVQLVESGGGLVQPG GSLRLSCAASGFTFD | 32 | DYAMS | 44 | WGRQAPG KGLEWVS | 56 | AISWNGGST YYAESMKG | 68 | RFTVSRDNAKNTLYLQ MNSLKSEDTAVYYCAK | 80 | ALDPLGVLA GTSGIYDY | 92 | WGQGTQ VTVSS | 104 |
| 6E10: | 18 | EVQLVESGGGLYQAG GSLRLSCAASGRTDS | 33 | SYAMG | 45 | WFRQAPG KEHEFVA | 57 | AISWSGGST YYADSVKG | 69 | RFTISRDNAKNTLYLQ MNSLKPEDTAVYYCGA | 81 | SYRWGITHE YEY | 93 | WGQGTQ VTVSS | 105 |

TABLE B-2-continued

Sequences for CDRs and frameworks, plus preferred combinations as provided in for formula I, i.e. FR1-CDR1-FR2-CDR2-FR3-CDR3-FR4 (the following terms: "ID" refers to the given SEQ ID NO. Preferred combinations of FR and CDR sequences for each Nanobody construct are used interchangeably throughout the application)

| Clone* | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 6F6: | 20 | EVQLVESGGGLVQPG GSLRLSCAASGSILG | 34 | INAMG | 46 | WYRQAPG KQRELVA | 58 | VIN-SGGST NYADSVKG | 70 | RFTISRDNAKNTVYLQ MNSLKPEDTAVYYCNA | 82 | DEWGDYPGQ VYDY | 94 | WGQGTQ VTVSS | 106 |
| 6G6: | 21 | EVQLVESGGGLAQAG GSLRLSCAASGRSLS | 35 | NYAMG | 47 | WFRQAPG KEREIVC | 59 | AISRSGSIT TYADSVKG | 71 | RFTIAKDNAANTVYLQ MNSLKPEDTAAYYCAA | 83 | DPMYYGIPD QNWDY | 95 | WGQGTQ VTVSS | 107 |
| 6H6: | 22 | EVQLMESGGGLVQAG GSLRLSCAASGRTFS | 36 | SYAMG | 48 | WFRQAPG KERENVA | 60 | AISSSGGYT YYPDSVKG | 72 | RFTISRDTAKNTVYLQ MNSLKPDDTAVYYCAG | 84 | TQPNFGWQL LLLQTEYDY | 96 | WGQGTQ VTVSS | 108 |
| 7G6: | 23 | EVQLVESGGGLVQAG GSLRLSCAVSGRTFS | 37 | PYTMG | 49 | WFRRAPG KEREFVA | 61 | ARTWSGGVA WYADSVKG | 73 | RFTISSDNAENMVYLQ MNSLKPEDTAVYYCAA | 85 | KSPGRTYSP REERAYAR | 97 | WGQGTQ VTVSS | 109 |
| 9G6: | 24 | EVQLVESGGGLVQAG GSLRLSCAASGRTLS | 38 | DYTMG | 50 | WFRQAPG KEREFVA | 62 | RINTGGPIT SYSDSVKG | 74 | RFTISRDNAKNTVYLQ MNSLKPEDTAVYNCAA | 86 | RLPTKMSPR DYSSYAY | 98 | RGQGTQ VTVSS | 110 |
| 9H5: | 25 | EVQLVESGGGLVQPG GSLRLSCAASGSIFN | 39 | LNPMG | 51 | WYRQAPG KQRELVA | 63 | TVT-GEGRT NYSDSVKG | 75 | RFTISRDNAKNTVYLQ MNSLKPEDTAVYYCNA | 87 | AFWAYDDAY | 99 | WGQGTQ VTVSS | 111 |

TABLE B-3

Amino acid sequences of immunoglobulin single variable sequences of the invention

| Name of clone | SEQ ID NO: | Amino acid sequences |
|---|---|---|
| 1C7: | 6 | EVQLVESGGGLVQAGGSLRLSCAASGRTFSSYAMGWFRQAPGK EREFVAGISWSGGSTTYADSVKGRFTISRDNAKNTVYLRMNSL KPEDTAVYYCAADPVGRADLYEYDYWGQGTQVTVSS |
| 1E2: | 7 | EVQLVESGGGLVQPGGSLRLSCAASGRTFSSYAMGWFRQAPGK EREFVAGISWSGSSSYYADSVKGRFTISRDNAKNTVYLQMNSL KPEDTAVYYCAADPVGRADLYEYDYWGQGTQVTVSS |
| 1E9: | 8 | EVQLVESGGGLVQPGGSLRLSCAASGFTLDHYTIGWFRQAPGN EREGVSCISSLDGSTYYADSVKGRFTISRDNAKDTVYLQMNSL KPEDTAVYYCAVAGCGAYGLIPYDYWGQGTQVTVSS |
| 5B7: | 9 | EVQLVESGGGLAQAGGSLRLSCAASGRSLSNYAMGWFRQAPGK EREIVCAISRSGSITTYADSVKGRFTIAKDNAANTVYLQMNSL KPEDTAAYYCAADPMYYGIPDQNWDYWGQGTQVTVSS |
| 5C7: | 10 | EVQLVESGGGLVQAGDSLRLSCAASGGTFGSSHMAWFRQVPEK EREFVAAISRSGGTTYYADSVKGRCTISRDNAKNTVYLQMNSL KPEDTAVYYCAAARFWGSTSTRMDDYQYWGQGTQVTVSS |
| 5D10: | 11 | EVQLVESGGGLAQAGGSLRLSCAASGRSLSNYAMGWFRQAPGK EREIVCAISRSGSITTYADSVKGRFTIAKDNAANTVYLQMNSL KPEDTAAYYCAADPMYYGIPDQNWDYWGQGTQVTVSS |
| 5E8: | 12 | EVQLVESGGGLAQAGGSLRLSCAASGRSLSNYAMGWFRQAPGK EREIVCAISRSGSITTYADSVKGRFTIAKDNAANTVYLQMNSL KPEDTAAYYCAADPMYYGIPDQNWDYWGQGTQVTVSS |
| 5G9: | 13 | EVQLVESGGGLVQTGGSLTLSCAASGRTFSPYAAGWFRHAPGK EREFVTAITWSGGSTYYADSVKGRFTISRDNAKNTVYLQMNSL KPEDTAVYYCAASYRWGITHEFDYWGQGTQVTVSS |
| 6A6: | 14 | EVQLVESGGGLAQAGGSLRLSCAASGRSLSNYAMGWFRQAPGK EREIVCAISRSGSITTYADSVKGRFTIAKDNAANTVYLQMNSL KPEDTAAYYCAADPMYYGIPDQNWDYWGQGTQVTVSS |
| 6B2: | 15 | EVQLVESGGGLVQAGGSLRLSCAASGRTFSSYAMGWFRQAPGK EREFVAAINWSGDSTYYADSVKGRFTISRDNAKNTVYLQMNSL KPEDTAVYYCAAGDVGRPDLYEYDYWGQGTQVTVSS |
| 6B6: | 16 | EVQLVESGGGLVQPGGSLRLSCAASGFTFDDYAMSWGTQAPGK GLEWVSAISWNGGSTYYAESMKGRFTVSRDNAKNTLYLQMNSL KSEDTAVYYCAKALDPLGVLAGTSGIYDYWGQGTQVTVSS |
| 6E6: | 17 | EVQLVESGGGLAQAGGSLRLSCAASGRSLSNYAMGWFRQAPGK EREIVCAISRSGSITTYADSVKGRFTIAKDNAANTVYLQMNSL KPEDTAAYYCAADPMYYGIPDQNWDYWGQGTQVTVSS |
| 6E10: | 18 | EVQLVESGGGLVQAGGSLRLSCAASGRTDSSYAMGWFRQAPGK EHEFVAAISWSGGSTYYADSVKGRFTISRDNAKNTLYLQMNSL KPEDTAVYYCGASYRWGITHEYEYWGQGTQVTVSS |
| 6E11: | 19 | EVQLVESGGGLAQAGGSLRLSCAASGRSLSNYAMGWFRQAPGK EREIVCAISRSGSITTYADSVKGRFTIAKDNAANTVYLQMNSL KPEDTAAYYCAADPMYYGIPDQNWDYWGQGTQVTVSS |
| 6F6: | 20 | EVQLVESGGGLVQPGGSLRLSCAASGSILGINAMGWYRQAPGK QRELVAVINSGGSTNYADSVKGRFTISRDNAKNTVYLQMNSLK PEDTAVYYCNADEWGDYPGQVYDYWGQGTQVTVSS |
| 6G6: | 21 | EVQLVESGGGLAQAGGSLRLSCAASGRSLSNYAMGWFRQAPGK EREIVCAISRSGSITTYADSVKGRFTIAKDNAANTVYLQMNSL KPEDTAAYYCAADPMYYGIPDQNWDYWGQGTQVTVSS |
| 6H6: | 22 | EVQLMESGGGLVQAGGSLRLSCAASGRTFSSYAMGWFRQAPGK ERENVAAISSSGGYTYYPDSVKGRFTISRDTAKNTVYLQMNSL KPDDTAVYYCAGTQPNFGWQLLLLQTEYDYWGQGTQVTVSS |
| 7G6: | 23 | EVQLVESGGGLVQAGGSLRLSCAVSGRTFSPYTMGWFRRAPGK EREFVAARTWSGGVAWYADSVKGRFTISSDNAENMVYLQMNSL KPEDTAVYYCAAKSPGRTYSPREERAYARWGQGTQVTVSS |
| 9G6: | 24 | EVQLVESGGGLVQAGGSLRLSCAASGRTLSDYTMGWFRQAPGK EREFVARINTGGPITSYSDSVKGRFTISRDNAKNIVYLQMNSL KPEDTAVYNCAARLPTKMSPRDYSSYAYRGQGTQVTVSS |
| 9H5: | 25 | EVQLVESGGGLVQPGGSLRLSCAASGSIFNLNPMGWYRQAPGK QRELVATVTGEGRTNYSDSVKGRFTISRDNAKNTVYLQMNSLK PEDTAVYYCNAAFWAYDDAYWGQGTQVTVSS |
| 9E6: | 26 | EVQLVESGGGLAQAGGSLRLSCAASGRSLSNYAMGWFRQAPGK EREIVCAISRSGSITTYADSVKGRFTIAKDNAANTVYLQMNSL KPEDTAAYYCAADPMYYGIPDQNWDYWGQGTQVTVSS |

TABLE B-3-continued

Amino acid sequences of immunoglobulin single variable sequences of the invention

| Name of clone | SEQ ID NO: | Amino acid sequences |
|---|---|---|
| 10G3 | 27 | EVQLVESGGGLVQAGGSLRLSCADSGRTFSSYAMGWFRQAPGK EREFVAGVNWSGDSTYYADSVKGRFTISRDNAKNTVYLQMNSL KPEDAAVYYCAADPVGRADLYEYDYWGQGTQVTVSS |

TABLE B4

Polypeptide sequences of the invention

| Name of clone | SEQ ID NO: | Amino acid sequences |
|---|---|---|
| 1E2-ALB | 112 | EVQLVESGGGLVQPGGSLRLSCAASGRTFSSYAMGWFRQAPGK EREFVAGISWSGSSSYYADSVKGRFTISRDNAKNTVYLQMNSL KPEDTAVYYCAADPVGRADLYEYDYWGQGTQVTVSSGGGGSGG GSEVQLVESGGGLVQPGNSLRLSCAASGFTFSSFGMSWVRQAP GKGLEWVSSISGSGSDTLYADSVKGRFTISRDNAKTTLYLQMN SLRPEDTAVYYCTIGGSLSRSSQGTLVTVSSGAADYKDHDGDY KDHDIDYKDDDDKGAAHHHHHH |
| 6E10-ALB | 113 | EVQLVESGGGLVQAGGSLRLSCAASGRTFSSYAMGWFRQAPGK EHEFVAAISWSGSSTYYADSVKGRFTISRDNAKNTLYLQMNSL KPEDTAVYYCEASYRWGITHEYEYWGQGTQVTVSSGGGGSGGG SEVQLVESGGGLVQPGNSLRLSCAASGFTFSSFGMSWVRQAPG KGLEWVSSISGSGSDTLYADSVKGRFTISRDNAKTTLYLQMNS LRPEDTAVYYCTIGGSLSRSSQGTLVTVSSGAADYKDHDGDYK DHDIDYKDDDDKGAAHHHHHH |

TABLE B-5

Linker sequences of the invention

| Name of linker | SEQ ID NO: | Amino acid sequences |
|---|---|---|
| 5GS | 117 | GGGGS |
| 6GS | 118 | SGGSGGS |
| 9GS | 119 | GGGGSGGGS |
| 10GS | 120 | GGGGSGGGGS |
| 15GS | 121 | GGGGSGGGGSGGGGS |
| 18GS | 122 | GGGGSGGGGSGGGGGGGS |
| 20GS | 123 | GGGGSGGGGSGGGGSGGGGS |
| 25GS | 124 | GGGGSGGGGSGGGGSGGGGSGGGGS |
| 30GS | 125 | GGGGSGGGGSGGGGSGGGGSGGGGSGGGGS |
| 35GS | 126 | GGGGSGGGGSGGGGSGGGGSGGGGSGGGGSGGGGS |

The invention claimed is:

1. An immunoglobulin single variable domain (ISVD) that binds HGF (SEQ ID NO: 1) with a Kd of less than 50 nM and more than $10^{-12}$ M and comprising an amino acid sequence of formula 1:

FR1-CDR1-FR2-CDR2-FR3-CDR3-FR4     (1);

wherein FR1 to FR4 refer to framework regions 1 to 4 and are framework regions (FRs) of an immunoglobulin single variable domain; and
wherein the CDR1 is SEQ ID NO: 45, CDR2 is SEQ ID NO: 69, and CDR3 is SEQ ID NO: 93.

2. A fusion polypeptide comprising a first ISVD according to claim 1 fused to a second ISVD.

3. The fusion polypeptide according to claim 2, wherein the first ISVD has the amino acid sequence of SEQ ID NO: 18.

4. The fusion polypeptide according to claim 2, wherein the second ISVD is an ISVD that binds human serum albumin.

5. The fusion polypeptide according to claim 4, wherein the ISVD that binds human serum albumin is Alb8 (SEQ ID NO: 115) or Alb11 (SEQ ID NO: 114).

6. The fusion polypeptide according to claim 4, wherein the fusion polypeptide has the amino acid sequence of SEQ ID NO: 113.

7. A pharmaceutical composition comprising the fusion polypeptide according to claim 2 and a pharmaceutically acceptable excipient.

8. A pharmaceutical composition comprising an ISVD according to claim 1 and a pharmaceutically acceptable excipient.

* * * * *

SEQUENCE LISTING

<160> NUMBER OF SEQ ID NOS: 130

<210> SEQ ID NO 1
<211> LENGTH: 728
<212> TYPE: PRT
<213> ORGANISM: Homo sapiens

<400> SEQUENCE: 1

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile His Arg His Lys Phe Leu Pro Glu Arg Tyr Pro Asp Lys Gly
    130                 135                 140
```

-continued

```
Phe Asp Asp Glu Thr Thr Glu Cys Ile Gln Gly Gln Gly Glu Gly Tyr
145                 150                 155                 160

Arg Gly Thr Val Asn Thr Ile Trp Asn Gly Ile Pro Cys Gln Arg Trp
            165                 170                 175

Asp Ser Gln Tyr Pro His Glu His Asp Met Thr Pro Glu Asn Phe Lys
            180                 185                 190

Cys Lys Asp Leu Arg Glu Asn Tyr Cys Arg Asn Pro Asp Gly Ser Glu
            195                 200                 205

Ser Pro Trp Cys Phe Thr Thr Asp Pro Asn Ile Arg Val Gly Tyr Cys
            210                 215                 220

Ser Gln Ile Pro Asn Cys Asp Met Ser His Gly Gln Asp Cys Tyr Arg
225                 230                 235                 240

Gly Asn Gly Lys Asn Tyr Met Gly Asn Leu Ser Gln Thr Arg Ser Gly
                245                 250                 255

Leu Thr Cys Ser Met Trp Asp Lys Asn Met Glu Asp Leu His Arg His
                260                 265                 270

Ile Phe Trp Glu Pro Asp Ala Ser Lys Leu Asn Glu Asn Tyr Cys Arg
                275                 280                 285

Asn Pro Asp Asp Asp Ala His Gly Pro Trp Cys Tyr Thr Gly Asn Pro
290                 295                 300

Leu Ile Pro Trp Asp Tyr Cys Pro Ile Ser Arg Cys Glu Gly Asp Thr
305                 310                 315                 320

Thr Pro Thr Ile Val Asn Leu Asp His Pro Val Ile Ser Cys Ala Lys
                325                 330                 335

Thr Lys Gln Leu Arg Val Val Asn Gly Ile Pro Thr Arg Thr Asn Ile
                340                 345                 350

Gly Trp Met Val Ser Leu Arg Tyr Arg Asn Lys His Ile Cys Gly Gly
                355                 360                 365

Ser Leu Ile Lys Glu Ser Trp Val Leu Thr Ala Arg Gln Cys Phe Pro
370                 375                 380

Ser Arg Asp Leu Lys Asp Tyr Glu Ala Trp Leu Gly Ile His Asp Val
385                 390                 395                 400

His Gly Arg Gly Asp Glu Lys Cys Lys Gln Val Leu Asn Val Ser Gln
                405                 410                 415

Leu Val Tyr Gly Pro Glu Gly Ser Asp Leu Val Leu Met Lys Leu Ala
                420                 425                 430

Arg Pro Ala Val Leu Asp Asp Phe Val Ser Thr Ile Asp Leu Pro Asn
                435                 440                 445

Tyr Gly Cys Thr Ile Pro Glu Lys Thr Ser Cys Ser Val Tyr Gly Trp
                450                 455                 460

Gly Tyr Thr Gly Leu Ile Asn Tyr Asp Gly Leu Leu Arg Val Ala His
465                 470                 475                 480

Leu Tyr Ile Met Gly Asn Glu Lys Cys Ser Gln His His Arg Gly Lys
                485                 490                 495

Val Thr Leu Asn Glu Ser Glu Ile Cys Ala Gly Ala Glu Lys Ile Gly
                500                 505                 510

Ser Gly Pro Cys Glu Gly Asp Tyr Gly Gly Pro Leu Val Cys Glu Gln
                515                 520                 525

His Lys Met Arg Met Val Leu Gly Val Ile Val Pro Gly Arg Gly Cys
                530                 535                 540

Ala Ile Pro Asn Arg Pro Gly Ile Phe Val Arg Val Ala Tyr Tyr Ala
545                 550                 555                 560

Lys Trp Ile His Lys Ile Ile Leu Thr Tyr Lys Val Pro Gln Ser Asn
```

```
                        565                 570                 575

Tyr Cys Arg Asn Pro Asp Gly Gln Pro Arg Pro Trp Cys Tyr Thr Leu
                580                 585                 590

Asp Pro His Thr Arg Trp Glu Tyr Cys Ala Ile Lys Thr Cys Ala Asp
                595                 600                 605

Asn Thr Met Asn Asp Thr Asp Val Pro Leu Gly Lys Gly Arg Ser Tyr
                610                 615                 620

Lys Gly Thr Val Arg Gly Glu Gly Gly Pro Trp Cys Phe Thr Ser
625                 630                 635                 640

Asn Pro Glu Val Arg Tyr Glu Val Cys Asp Ile Pro Gln Cys Ser Glu
                645                 650                 655

Val Glu Cys Met Thr Cys Asn Gly Glu Ser Tyr Arg Gly Leu Met Asp
                660                 665                 670

His Thr Glu Ser Gly Lys Ile Cys Gln Arg Trp Asp His Gln Thr Pro
                675                 680                 685

Ser Ile Thr Lys Ser Gly Ile Lys Cys Gln Pro Trp Ser Ser Met Ile
                690                 695                 700

Pro His Glu His Ser Phe Leu Pro Ser Ser Tyr Arg Gly Lys Asp Leu
705                 710                 715                 720

Gln Glu Asn Tyr Cys Arg Asn Pro
                725

<210> SEQ ID NO 2
<211> LENGTH: 697
<212> TYPE: PRT
<213> ORGANISM: Artificial Sequence
<220> FEATURE:
<223> OTHER INFORMATION: recombinant

<400> SEQUENCE: 2

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
                20                  25                  30

Val Asn Thr Ala Asp Gln Cys Ala Asn Arg Cys Thr Arg Asn Lys Gly
                35                  40                  45

Leu Pro Phe Thr Cys Lys Ala Phe Val Phe Asp Lys Ala Arg Lys Gln
        50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
                100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
        130                 135                 140

Tyr Cys Arg Asn Pro Arg Gly Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
                180                 185                 190

Asp His Thr Glu Ser Gly Lys Ile Cys Gln Arg Trp Asp His Gln Thr
```

-continued

```
                195                 200                 205
    Pro His Arg His Lys Phe Leu Pro Glu Arg Tyr Pro Asp Lys Gly Phe
    210                 215                 220

Asp Asp Asn Tyr Cys Arg Asn Pro Asp Gly Gln Pro Arg Pro Trp Cys
    225                 230                 235                 240

Tyr Thr Leu Asp Pro His Thr Arg Trp Glu Tyr Cys Ala Ile Lys Thr
                    245                 250                 255

Cys Ala Asp Asn Thr Met Asn Asp Thr Asp Val Pro Leu Glu Thr Thr
                    260                 265                 270

Glu Cys Ile Gln Gly Gln Gly Glu Gly Tyr Arg Gly Thr Val Asn Thr
                275                 280                 285

Ile Trp Asn Gly Ile Pro Cys Gln Arg Trp Asp Ser Gln Tyr Pro His
    290                 295                 300

Glu His Asp Met Thr Pro Glu Asn Phe Lys Cys Lys Asp Leu Arg Glu
    305                 310                 315                 320

Asn Tyr Cys Arg Asn Pro Asp Gly Ser Glu Ser Pro Trp Cys Phe Thr
                    325                 330                 335

Thr Asp Pro Asn Ile Arg Val Gly Tyr Cys Ser Gln Ile Pro Asn Cys
                    340                 345                 350

Asp Met Ser His Gly Gln Asp Cys Tyr Arg Gly Asn Gly Lys Asn Tyr
                355                 360                 365

Met Gly Asn Leu Ser Gln Thr Arg Ser Gly Leu Thr Cys Ser Met Trp
    370                 375                 380

Asp Lys Asn Met Glu Asp Leu His Arg His Ile Phe Trp Glu Pro Asp
    385                 390                 395                 400

Ala Ser Lys Leu Asn Glu Asn Tyr Cys Arg Asn Pro Asp Asp Asp Ala
                    405                 410                 415

His Gly Pro Trp Cys Tyr Thr Gly Asn Pro Leu Ile Pro Trp Asp Tyr
                    420                 425                 430

Cys Pro Ile Ser Arg Cys Glu Gly Asp Thr Thr Pro Thr Ile Val Asn
                435                 440                 445

Leu Asp His Pro Val Ile Ser Cys Ala Lys Thr Lys Gln Leu Arg Val
    450                 455                 460

Val Asn Gly Ile Pro Thr Arg Thr Asn Ile Gly Trp Met Val Ser Leu
    465                 470                 475                 480

Arg Tyr Arg Asn Lys His Ile Cys Gly Gly Ser Leu Ile Lys Glu Ser
                    485                 490                 495

Trp Val Leu Thr Ala Arg Gln Cys Phe Pro Ser Arg Asp Leu Lys Asp
                    500                 505                 510

Tyr Glu Ala Trp Leu Gly Ile His Asp Val His Gly Arg Gly Asp Glu
                515                 520                 525

Lys Cys Lys Gln Val Leu Asn Val Ser Gln Leu Val Tyr Gly Pro Glu
    530                 535                 540

Gly Ser Asp Leu Val Leu Met Lys Leu Ala Arg Pro Ala Val Leu Asp
    545                 550                 555                 560

Asp Phe Val Ser Thr Ile Asp Leu Pro Asn Tyr Gly Cys Thr Ile Pro
                    565                 570                 575

Glu Lys Thr Ser Cys Ser Val Tyr Gly Trp Gly Tyr Thr Gly Leu Ile
                    580                 585                 590

Asn Tyr Asp Gly Leu Leu Arg Val Ala His Leu Tyr Ile Met Gly Asn
                595                 600                 605

Glu Lys Cys Ser Gln His His Arg Gly Lys Val Thr Leu Asn Glu Ser
    610                 615                 620
```

```
Glu Ile Cys Ala Gly Ala Glu Lys Ile Gly Ser Gly Pro Cys Glu Gly
625                 630                 635                 640

Asp Tyr Gly Gly Pro Leu Val Cys Glu Gln His Lys Met Arg Met Val
                645                 650                 655

Leu Gly Val Ile Val Pro Gly Arg Gly Cys Ala Ile Pro Asn Arg Pro
            660                 665                 670

Gly Ile Phe Val Arg Val Ala Tyr Tyr Ala Lys Trp Ile His Lys Ile
        675                 680                 685

Ile Leu Thr Tyr Lys Val Pro Gln Ser
    690                 695

<210> SEQ ID NO 3
<211> LENGTH: 697
<212> TYPE: PRT
<213> ORGANISM: Artificial Sequence
<220> FEATURE:
<223> OTHER INFORMATION: recombinant

<400> SEQUENCE: 3

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
130                 135                 140

Tyr Cys Arg Asn Pro Arg Gly Glu Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
            180                 185                 190

Asp His Thr Glu Ser Gly Lys Ile Cys Gln Arg Trp Asp His Gln Thr
        195                 200                 205

Pro His Arg His Lys Phe Leu Pro Glu Arg Tyr Pro Asp Lys Gly Phe
210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
            260                 265                 270

Glu Cys Ile Gln Gly Gln Gly Gly Tyr Arg Gly Thr Val Asn Thr
        275                 280                 285
```

-continued

```
Ile Trp Asn Gly Ile Pro Cys Gln Arg Trp Asp Ser Gln Tyr Pro His
    290                 295                 300
Glu His Asp Met Thr Pro Glu Asn Phe Lys Cys Lys Asp Leu Arg Glu
305                 310                 315                 320
Asn Tyr Cys Arg Asn Pro Asp Gly Ser Glu Ser Pro Trp Cys Phe Thr
                325                 330                 335
Thr Asp Pro Asn Ile Arg Val Gly Tyr Cys Ser Gln Ile Pro Asn Cys
            340                 345                 350
Asp Met Ser His Gly Gln Asp Cys Tyr Arg Gly Asn Gly Lys Asn Tyr
        355                 360                 365
Met Gly Asn Leu Ser Gln Thr Arg Ser Gly Leu Thr Cys Ser Met Trp
    370                 375                 380
Asp Lys Asn Met Glu Asp Leu His Arg His Ile Phe Trp Glu Pro Asp
385                 390                 395                 400
Ala Ser Lys Leu Asn Glu Asn Tyr Cys Arg Asn Pro Asp Asp Asp Ala
                405                 410                 415
His Gly Pro Trp Cys Tyr Thr Gly Asn Pro Leu Ile Pro Trp Asp Tyr
            420                 425                 430
Cys Pro Ile Ser Arg Cys Glu Gly Asp Thr Thr Pro Thr Ile Val Asn
        435                 440                 445
Leu Asp His Pro Val Ile Ser Cys Ala Lys Thr Lys Gln Leu Arg Val
    450                 455                 460
Val Asn Gly Ile Pro Thr Arg Thr Asn Ile Gly Trp Met Val Ser Leu
465                 470                 475                 480
Arg Tyr Arg Asn Lys His Ile Cys Gly Gly Ser Leu Ile Lys Glu Ser
                485                 490                 495
Trp Val Leu Thr Ala Arg Gln Cys Phe Pro Ser Arg Asp Leu Lys Asp
            500                 505                 510
Tyr Glu Ala Trp Leu Gly Ile His Asp Val His Gly Arg Gly Asp Glu
        515                 520                 525
Lys Cys Lys Gln Val Leu Asn Val Ser Gln Leu Val Tyr Gly Pro Glu
    530                 535                 540
Gly Ser Asp Leu Val Leu Met Lys Leu Ala Arg Pro Ala Val Leu Asp
545                 550                 555                 560
Asp Phe Val Ser Thr Ile Asp Leu Pro Asn Tyr Gly Cys Thr Ile Pro
                565                 570                 575
Glu Lys Thr Ser Cys Ser Val Tyr Gly Trp Gly Tyr Thr Gly Leu Ile
            580                 585                 590
Asn Tyr Asp Gly Leu Leu Arg Val Ala His Leu Tyr Ile Met Gly Asn
        595                 600                 605
Glu Lys Cys Ser Gln His His Arg Gly Lys Val Thr Leu Asn Glu Ser
    610                 615                 620
Glu Ile Cys Ala Gly Ala Glu Lys Ile Gly Ser Gly Pro Cys Glu Gly
625                 630                 635                 640
Asp Tyr Gly Gly Pro Leu Val Cys Glu Gln His Lys Met Arg Met Val
                645                 650                 655
Leu Gly Val Ile Val Pro Gly Arg Gly Cys Ala Ile Pro Asn Arg Pro
            660                 665                 670
Gly Ile Phe Val Arg Val Ala Tyr Tyr Ala Lys Trp Ile His Lys Ile
        675                 680                 685
Ile Leu Thr Tyr Lys Val Pro Gln Ser
    690                 695
```

<210> SEQ ID NO 4
<211> LENGTH: 1390
<212> TYPE: PRT
<213> ORGANISM: Homo sapiens

<400> SEQUENCE: 4

```
Met Lys Ala Pro Ala Val Leu Ala Pro Gly Ile Leu Val Leu Leu Phe
  1               5                  10                  15

Thr Leu Val Gln Arg Ser Asn Gly Glu Cys Lys Glu Ala Leu Ala Lys
                 20                  25                  30

Ser Glu Met Asn Val Asn Met Lys Tyr Gln Leu Pro Asn Phe Thr Ala
             35                  40                  45

Glu Thr Pro Ile Gln Asn Val Ile Leu His Glu His His Ile Phe Leu
 50                  55                  60

Gly Ala Thr Asn Tyr Ile Tyr Val Leu Asn Glu Glu Asp Leu Gln Lys
 65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
            370                 375                 380
```

-continued

```
Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
            405                 410                 415

Arg Thr Glu Phe Thr Thr Ala Leu Gln Arg Val Asp Leu Phe Met Gly
        420                 425                 430

Gln Phe Ser Glu Val Leu Leu Thr Ser Ile Ser Thr Phe Ile Lys Gly
    435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800
```

```
Cys Thr Thr Pro Ser Leu Gln Gln Leu Asn Leu Gln Leu Pro Leu Lys
            805                 810                 815

Thr Lys Ala Phe Phe Met Leu Asp Gly Ile Leu Ser Lys Tyr Phe Asp
        820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser  Val Asp Tyr Arg Ala  Thr Phe Pro
        995                 1000                1005

Glu Asp  Gln Phe Pro Asn Ser  Ser Gln Asn Gly Ser  Cys Arg Gln
    1010                1015                1020

Val Gln  Tyr Pro Leu Thr Asp  Met Ser Pro Ile Leu  Thr Ser Gly
    1025                1030                1035

Asp Ser  Asp Ile Ser Ser Pro  Leu Leu Gln Asn Thr  Val His Ile
    1040                1045                1050

Asp Leu  Ser Ala Leu Asn Pro  Glu Leu Val Gln Ala  Val Gln His
    1055                1060                1065

Val Val  Ile Gly Pro Ser Ser  Leu Ile Val His Phe  Asn Glu Val
    1070                1075                1080

Ile Gly  Arg Gly His Phe Gly  Cys Val Tyr His Gly  Thr Leu Leu
    1085                1090                1095

Asp Asn  Asp Gly Lys Lys Ile  His Cys Ala Val Lys  Ser Leu Asn
    1100                1105                1110

Arg Ile  Thr Asp Ile Gly Glu  Val Ser Gln Phe Leu  Thr Glu Gly
    1115                1120                1125

Ile Ile  Met Lys Asp Phe Ser  His Pro Asn Val Leu  Ser Leu Leu
    1130                1135                1140

Gly Ile  Cys Leu Arg Ser Glu  Gly Ser Pro Leu Val  Val Leu Pro
    1145                1150                1155

Tyr Met  Lys His Gly Asp Leu  Arg Asn Phe Ile Arg  Asn Glu Thr
    1160                1165                1170

His Asn  Pro Thr Val Lys Asp  Leu Ile Gly Phe Gly  Leu Gln Val
    1175                1180                1185

Ala Lys  Gly Met Lys Tyr Leu  Ala Ser Lys Lys Phe  Val His Arg
    1190                1195                1200

Asp Leu  Ala Ala Arg Asn Cys  Met Leu Asp Glu Lys  Phe Thr Val
```

```
              1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 5
<211> LENGTH: 1152
<212> TYPE: PRT
<213> ORGANISM: Artificial Sequence
<220> FEATURE:
<223> OTHER INFORMATION: chimera

<400> SEQUENCE: 5

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
                20                  25                  30

Leu His Glu His His Ile Phe Leu Gly Ala Thr Asn Tyr Ile Tyr Val
            35                  40                  45

Leu Asn Glu Glu Asp Leu Gln Lys Val Ala Glu Tyr Lys Thr Gly Pro
        50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
```

```
            165                 170                 175
Ile Asn Ser Ser Tyr Phe Pro Asp His Pro Leu His Ser Ile Ser Val
            180                 185                 190
Arg Arg Leu Lys Glu Thr Lys Asp Gly Phe Met Phe Leu Thr Asp Gln
            195                 200                 205
Ser Tyr Ile Asp Val Leu Pro Glu Phe Arg Asp Ser Tyr Pro Ile Lys
            210                 215                 220
Tyr Val His Ala Phe Glu Ser Asn Asn Phe Ile Tyr Phe Leu Thr Val
225                 230                 235                 240
Gln Arg Glu Thr Leu Asp Ala Gln Thr Phe His Thr Arg Ile Ile Arg
            245                 250                 255
Phe Cys Ser Ile Asn Ser Gly Leu His Ser Tyr Met Glu Met Pro Leu
            260                 265                 270
Glu Cys Ile Leu Thr Glu Lys Arg Lys Arg Ser Thr Lys Lys Glu
            275                 280                 285
Val Phe Asn Ile Leu Gln Ala Ala Tyr Val Ser Lys Pro Gly Ala Gln
            290                 295                 300
Leu Ala Arg Gln Ile Gly Ala Ser Leu Asn Asp Asp Ile Leu Phe Gly
305                 310                 315                 320
Val Phe Ala Gln Ser Lys Pro Asp Ser Ala Glu Pro Met Asp Arg Ser
            325                 330                 335
Ala Met Cys Ala Phe Pro Ile Lys Tyr Val Asn Asp Phe Phe Asn Lys
            340                 345                 350
Ile Val Asn Lys Asn Asn Val Arg Cys Leu Gln His Phe Tyr Gly Pro
            355                 360                 365
Asn His Glu His Cys Phe Asn Arg Thr Leu Leu Arg Asn Ser Ser Gly
            370                 375                 380
Cys Glu Ala Arg Arg Asp Glu Tyr Arg Thr Glu Phe Thr Thr Ala Leu
385                 390                 395                 400
Gln Arg Val Asp Leu Phe Met Gly Gln Phe Ser Glu Val Leu Leu Thr
            405                 410                 415
Ser Ile Ser Thr Phe Ile Lys Gly Asp Leu Thr Ile Ala Asn Leu Gly
            420                 425                 430
Thr Ser Glu Gly Arg Phe Met Gln Val Val Ser Arg Ser Gly Pro
            435                 440                 445
Ser Thr Pro His Val Asn Phe Leu Leu Asp Ser His Pro Val Ser Pro
            450                 455                 460
Glu Val Ile Val Glu His Thr Leu Asn Gln Asn Gly Tyr Thr Leu Val
465                 470                 475                 480
Ile Thr Gly Lys Lys Ile Thr Lys Ile Pro Leu Asn Gly Leu Gly Cys
            485                 490                 495
Arg His Phe Gln Ser Cys Ser Gln Cys Leu Ser Ala Pro Pro Phe Val
            500                 505                 510
Gln Cys Gly Trp Cys His Asp Lys Cys Val Arg Ser Glu Glu Cys Leu
            515                 520                 525
Ser Gly Thr Trp Thr Gln Gln Ile Cys Leu Pro Ala Ile Tyr Lys Val
            530                 535                 540
Phe Pro Asn Ser Ala Pro Leu Glu Gly Gly Thr Arg Leu Thr Ile Cys
545                 550                 555                 560
Gly Trp Asp Phe Gly Phe Arg Arg Asn Asn Lys Phe Asp Leu Lys Lys
            565                 570                 575
Thr Arg Val Leu Leu Gly Asn Glu Ser Cys Thr Leu Thr Leu Ser Glu
            580                 585                 590
```

```
Ser Thr Met Asn Thr Leu Lys Cys Thr Val Gly Pro Ala Met Asn Lys
        595                 600                 605

His Phe Asn Met Ser Ile Ile Ile Ser Asn Gly His Gly Thr Thr Gln
610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
                645                 650                 655

Tyr Leu Asn Ser Gly Asn Ser Arg His Ile Ser Ile Gly Gly Lys Thr
                660                 665                 670

Cys Thr Leu Lys Ser Val Ser Asn Ser Ile Leu Glu Cys Tyr Thr Pro
                675                 680                 685

Ala Gln Thr Ile Ser Thr Glu Phe Ala Val Lys Leu Lys Ile Asp Leu
                690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
                725                 730                 735

Thr Gly Val Gly Lys Asn Leu Asn Ser Val Ser Val Pro Arg Met Val
                740                 745                 750

Ile Asn Val His Glu Ala Gly Arg Asn Phe Thr Val Ala Cys Gln His
                755                 760                 765

Arg Ser Asn Ser Glu Ile Ile Cys Cys Thr Thr Pro Ser Leu Gln Gln
                770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
                820                 825                 830

Val Leu Glu Ile Lys Gly Asn Asp Ile Asp Pro Glu Ala Val Lys Gly
                835                 840                 845

Glu Val Leu Lys Val Gly Asn Lys Ser Cys Glu Asn Ile His Leu His
                850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr His Ile Glu Gly
                900                 905                 910

Arg Met Asp Pro Lys Ser Cys Asp Lys Thr His Thr Cys Pro Pro Cys
                915                 920                 925

Pro Ala Pro Glu Leu Leu Gly Gly Pro Ser Val Phe Leu Phe Pro Pro
                930                 935                 940

Lys Pro Lys Asp Thr Leu Met Ile Ser Arg Thr Pro Glu Val Thr Cys
945                 950                 955                 960

Val Val Val Asp Val Ser His Glu Asp Pro Glu Val Lys Phe Asn Trp
                965                 970                 975

Tyr Val Asp Gly Val Glu Val His Asn Ala Lys Thr Lys Pro Arg Glu
                980                 985                 990

Glu Gln Tyr Asn Ser Thr Tyr Arg  Val Val Ser Val Leu  Thr Val Leu
                995                 1000                1005
```

```
His Gln Asp Trp Leu Asn Gly Lys Glu Tyr Lys Cys Lys Val Ser
    1010                1015                1020

Asn Lys Ala Leu Pro Ala Pro Ile Glu Lys Thr Ile Ser Lys Ala
    1025                1030                1035

Lys Gly Gln Pro Arg Glu Pro Gln Val Tyr Thr Leu Pro Pro Ser
    1040                1045                1050

Arg Asp Glu Leu Thr Lys Asn Gln Val Ser Leu Thr Cys Leu Val
    1055                1060                1065

Lys Gly Phe Tyr Pro Ser Asp Ile Ala Val Glu Trp Glu Ser Asn
    1070                1075                1080

Gly Gln Pro Glu Asn Asn Tyr Lys Thr Thr Pro Pro Val Leu Asp
    1085                1090                1095

Ser Asp Gly Ser Phe Phe Leu Tyr Ser Lys Leu Thr Val Asp Lys
    1100                1105                1110

Ser Arg Trp Gln Gln Gly Asn Val Phe Ser Cys Ser Val Met His
    1115                1120                1125

Glu Ala Leu His Asn His Tyr Thr Gln Lys Ser Leu Ser Leu Ser
    1130                1135                1140

Pro Gly Lys His His His His His His
    1145                1150

<210> SEQ ID NO 6
<211> LENGTH: 122
<212> TYPE: PRT
<213> ORGANISM: Artificial Sequence
<220> FEATURE:
<223> OTHER INFORMATION: ISVD derived sequence

<400> SEQUENCE: 6

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Gly Ile Ser Trp Ser Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Arg Met Asn Ser Leu Lys Pro Glu Asp Thr Ala Val Tyr Tyr Cys
                85                  90                  95

Ala Ala Asp Pro Val Gly Arg Ala Asp Leu Tyr Glu Tyr Asp Tyr Trp
            100                 105                 110

Gly Gln Gly Thr Gln Val Thr Val Ser Ser
        115                 120

<210> SEQ ID NO 7
<211> LENGTH: 122
<212> TYPE: PRT
<213> ORGANISM: Artificial Sequence
<220> FEATURE:
<223> OTHER INFORMATION: ISVD derived sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30
```

```
Ala Met Gly Trp Phe Arg Gln Ala Pro Gly Lys Glu Arg Glu Phe Val
        35                  40                  45

Ala Gly Ile Ser Trp Ser Gly Ser Ser Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Asp Pro Val Gly Arg Ala Asp Leu Tyr Glu Tyr Asp Tyr Trp
             100                 105                 110

Gly Gln Gly Thr Gln Val Thr Val Ser Ser
            115                 120

<210> SEQ ID NO 8
<211> LENGTH: 122
<212> TYPE: PRT
<213> ORGANISM: Artificial Sequence
<220> FEATURE:
<223> OTHER INFORMATION: ISVD derived sequence

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Asp His Tyr
             20                  25                  30

Thr Ile Gly Trp Phe Arg Gln Ala Pro Gly Asn Glu Arg Glu Gly Val
        35                  40                  45

Ser Cys Ile Ser Ser Leu Asp Gly Ser Thr Tyr Tyr Ala Asp Ser Val
 50                  55                  60

Lys Gly Arg Phe Thr Ile Ser Arg Asp Asn Ala Lys Asp Thr Val Tyr
 65                  70                  75                  80

Leu Gln Met Asn Ser Leu Lys Pro Glu Asp Thr Ala Val Tyr Tyr Cys
                 85                  90                  95

Ala Val Ala Gly Cys Gly Ala Tyr Gly Leu Ile Pro Tyr Asp Tyr Trp
             100                 105                 110

Gly Gln Gly Thr Gln Val Thr Val Ser Ser
            115                 120

<210> SEQ ID NO 9
<211> LENGTH: 123
<212> TYPE: PRT
<213> ORGANISM: Artificial Sequence
<220> FEATURE:
<223> OTHER INFORMATION: ISVD derived sequence

<400> SEQUENCE: 9

Glu Val Gln Leu Val Glu Ser Gly Gly Gly Leu Ala Gln Ala Gly Gly
 1               5                  10                  15

Ser Leu Arg Leu Ser Cys Ala Ala Ser Gly Arg Ser Leu Ser Asn Tyr
             20                  25                  30

Ala Met Gly Trp Phe Arg Gln Ala Pro Gly Lys Glu Arg Glu Ile Val
        35                  40                  45

Cys Ala Ile Ser Arg Ser Gly Ser Ile Thr Thr Tyr Ala Asp Ser Val
 50                  55                  60

Lys Gly Arg Phe Thr Ile Ala Lys Asp Asn Ala Ala Asn Thr Val Tyr
 65                  70                  75                  80

Leu Gln Met Asn Ser Leu Lys Pro Glu Asp Thr Ala Ala Tyr Tyr Cys
```

```
                    85                  90                  95
Ala Ala Asp Pro Met Tyr Tyr Gly Ile Pro Asp Gln Asn Trp Asp Tyr
            100                 105                 110

Trp Gly Gln Gly Thr Gln Val Thr Val Ser Ser
        115                 120
```

<210> SEQ ID NO 10
<211> LENGTH: 125
<212> TYPE: PRT
<213> ORGANISM: Artificial Sequence
<220> FEATURE:
<223> OTHER INFORMATION: ISVD derived sequence

<400> SEQUENCE: 10

```
Glu Val Gln Leu Val Glu Ser Gly Gly Gly Leu Val Gln Ala Gly Asp
1               5                   10                  15

Ser Leu Arg Leu Ser Cys Ala Ala Ser Gly Gly Thr Phe Gly Ser Ser
            20                  25                  30

His Met Ala Trp Phe Arg Gln Val Pro Glu Lys Glu Arg Glu Phe Val
        35                  40                  45

Ala Ala Ile Ser Arg Ser Gly Gly Thr Thr Tyr Tyr Ala Asp Ser Val
    50                  55                  60

Lys Gly Arg Cys Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Arg Phe Trp Gly Ser Thr Ser Thr Arg Met Asp Asp Tyr
            100                 105                 110

Gln Tyr Trp Gly Gln Gly Thr Gln Val Thr Val Ser Ser
        115                 120                 125
```

<210> SEQ ID NO 11
<211> LENGTH: 123
<212> TYPE: PRT
<213> ORGANISM: Artificial Sequence
<220> FEATURE:
<223> OTHER INFORMATION: ISVD derived sequence

<400> SEQUENCE: 11

```
Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Ser Leu Ser Asn Tyr
            20                  25                  30

Ala Met Gly Trp Phe Arg Gln Ala Pro Gly Lys Glu Arg Glu Ile Val
        35                  40                  45

Cys Ala Ile Ser Arg Ser Gly Ser Ile Thr Thr Tyr Ala Asp Ser Val
    50                  55                  60

Lys Gly Arg Phe Thr Ile Ala Lys Asp Asn Ala Ala Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Asp Pro Met Tyr Tyr Gly Ile Pro Asp Gln Asn Trp Asp Tyr
            100                 105                 110

Trp Gly Gln Gly Thr Gln Val Thr Val Ser Ser
        115                 120
```

<210> SEQ ID NO 12
<211> LENGTH: 123

```
<212> TYPE: PRT
<213> ORGANISM: Artificial Sequence
<220> FEATURE:
<223> OTHER INFORMATION: ISVD derived sequence

<400> SEQUENCE: 12

Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Ser Leu Ser Asn Tyr
            20                  25                  30

Ala Met Gly Trp Phe Arg Gln Ala Pro Gly Lys Glu Arg Glu Ile Val
        35                  40                  45

Cys Ala Ile Ser Arg Ser Gly Ser Ile Thr Thr Tyr Ala Asp Ser Val
    50                  55                  60

Lys Gly Arg Phe Thr Ile Ala Lys Asp Asn Ala Ala Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Asp Pro Met Tyr Tyr Gly Ile Pro Asp Gln Asn Trp Asp Tyr
            100                 105                 110

Trp Gly Gln Gly Thr Gln Val Thr Val Ser Ser
        115                 120

<210> SEQ ID NO 13
<211> LENGTH: 121
<212> TYPE: PRT
<213> ORGANISM: Artificial Sequence
<220> FEATURE:
<223> OTHER INFORMATION: ISVD derived sequence

<400> SEQUENCE: 13

Glu Val Gln Leu Val Glu Ser Gly Gly Gly Leu Val Gln Thr Gly Gly
1               5                   10                  15

Ser Leu Arg Leu Ser Cys Ala Ala Ser Gly Arg Thr Phe Ser Pro Tyr
            20                  25                  30

Ala Ala Gly Trp Phe Arg His Ala Pro Gly Lys Glu Arg Glu Phe Val
        35                  40                  45

Thr Ala Ile Thr Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Tyr Arg Trp Gly Ile Thr His Glu Phe Asp Tyr Trp Gly
            100                 105                 110

Gln Gly Thr Gln Val Thr Val Ser Ser
        115                 120

<210> SEQ ID NO 14
<211> LENGTH: 123
<212> TYPE: PRT
<213> ORGANISM: Artificial Sequence
<220> FEATURE:
<223> OTHER INFORMATION: ISVD derived sequence

<400> SEQUENCE: 14

Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Ser Leu Ser Asn Tyr
```

```
                20                  25                  30
Ala Met Gly Trp Phe Arg Gln Ala Pro Gly Lys Glu Arg Glu Ile Val
            35                  40                  45
Cys Ala Ile Ser Arg Ser Gly Ser Ile Thr Thr Tyr Ala Asp Ser Val
        50                  55                  60
Lys Gly Arg Phe Thr Ile Ala Lys Asp Asn Ala Asn Thr Val Tyr
65                  70                  75                  80
Leu Gln Met Asn Ser Leu Lys Pro Glu Asp Thr Ala Ala Tyr Tyr Cys
                85                  90                  95
Ala Ala Asp Pro Met Tyr Tyr Gly Ile Pro Asp Gln Asn Trp Asp Tyr
            100                 105                 110
Trp Gly Gln Gly Thr Gln Val Thr Val Ser Ser
            115                 120
```

<210> SEQ ID NO 15
<211> LENGTH: 122
<212> TYPE: PRT
<213> ORGANISM: Artificial Sequence
<220> FEATURE:
<223> OTHER INFORMATION: ISVD derived sequence

<400> SEQUENCE: 15

```
Glu Val Gln Leu Val Glu Ser Gly Gly Gly Leu Val Gln Ala Gly Gly
1               5                   10                  15
Ser Leu Arg Leu Ser Cys Ala Ala Ser Gly Arg Thr Phe Ser Ser Tyr
                20                  25                  30
Ala Met Gly Trp Phe Arg Gln Ala Pro Gly Lys Glu Arg Glu Phe Val
            35                  40                  45
Ala Ala Ile Asn Trp Ser Gly Asp Ser Thr Tyr Tyr Ala Asp Ser Val
        50                  55                  60
Lys Gly Arg Phe Thr Ile Ser Arg Asp Asn Ala Lys Asn Thr Val Tyr
65                  70                  75                  80
Leu Gln Met Asn Ser Leu Lys Pro Glu Asp Thr Ala Val Tyr Tyr Cys
                85                  90                  95
Ala Ala Gly Asp Val Gly Arg Pro Asp Leu Tyr Glu Tyr Asp Tyr Trp
            100                 105                 110
Gly Gln Gly Thr Gln Val Thr Val Ser Ser
            115                 120
```

<210> SEQ ID NO 16
<211> LENGTH: 126
<212> TYPE: PRT
<213> ORGANISM: Artificial Sequence
<220> FEATURE:
<223> OTHER INFORMATION: ISVD derived sequence

<400> SEQUENCE: 16

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asp Asp Tyr
                20                  25                  30
Ala Met Ser Trp Gly Arg Gln Ala Pro Gly Lys Gly Leu Glu Trp Val
            35                  40                  45
Ser Ala Ile Ser Trp Asn Gly Gly Ser Thr Tyr Tyr Ala Glu Ser Met
        50                  55                  60
Lys Gly Arg Phe Thr Val Ser Arg Asp Asn Ala Lys Asn Thr Leu Tyr
65                  70                  75                  80
```

```
Leu Gln Met Asn Ser Leu Lys Ser Glu Asp Thr Ala Val Tyr Tyr Cys
                85                  90                  95

Ala Lys Ala Leu Asp Pro Leu Gly Val Leu Ala Gly Thr Ser Gly Ile
            100                 105                 110

Tyr Asp Tyr Trp Gly Gln Gly Thr Gln Val Thr Val Ser Ser
        115                 120                 125

<210> SEQ ID NO 17
<211> LENGTH: 123
<212> TYPE: PRT
<213> ORGANISM: Artificial Sequence
<220> FEATURE:
<223> OTHER INFORMATION: ISVD derived sequence

<400> SEQUENCE: 17

Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Ser Leu Ser Asn Tyr
            20                  25                  30

Ala Met Gly Trp Phe Arg Gln Ala Pro Gly Lys Glu Arg Glu Ile Val
            35                  40                  45

Cys Ala Ile Ser Arg Ser Gly Ser Ile Thr Thr Tyr Ala Asp Ser Val
        50                  55                  60

Lys Gly Arg Phe Thr Ile Ala Lys Asp Asn Ala Ala Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Asp Pro Met Tyr Tyr Gly Ile Pro Asp Gln Asn Trp Asp Tyr
            100                 105                 110

Trp Gly Gln Gly Thr Gln Val Thr Val Ser Ser
        115                 120

<210> SEQ ID NO 18
<211> LENGTH: 121
<212> TYPE: PRT
<213> ORGANISM: Artificial Sequence
<220> FEATURE:
<223> OTHER INFORMATION: ISVD derived sequence

<400> SEQUENCE: 18

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Asp Ser Ser Tyr
            20                  25                  30

Ala Met Gly Trp Phe Arg Gln Ala Pro Gly Lys Glu His Glu Phe Val
            35                  40                  45

Ala Ala Ile Ser Trp Ser Gly Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Gly Ala Ser Tyr Arg Trp Gly Ile Thr His Glu Tyr Gly Tyr Trp Gly
            100                 105                 110

Gln Gly Thr Gln Val Thr Val Ser Ser
        115                 120

<210> SEQ ID NO 19
```

<211> LENGTH: 123
<212> TYPE: PRT
<213> ORGANISM: Artificial Sequence
<220> FEATURE:
<223> OTHER INFORMATION: ISVD derived sequence

<400> SEQUENCE: 19

Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Ser Leu Ser Asn Tyr
            20                  25                  30

Ala Met Gly Trp Phe Arg Gln Ala Pro Gly Lys Glu Arg Glu Ile Val
        35                  40                  45

Cys Ala Ile Ser Arg Ser Gly Ser Ile Thr Thr Tyr Ala Asp Ser Val
    50                  55                  60

Lys Gly Arg Phe Thr Ile Ala Lys Asp Asn Ala Ala Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Asp Pro Met Tyr Tyr Gly Ile Pro Asp Gln Asn Trp Asp Tyr
            100                 105                 110

Trp Gly Gln Gly Thr Gln Val Thr Val Ser Ser
            115                 120

<210> SEQ ID NO 20
<211> LENGTH: 121
<212> TYPE: PRT
<213> ORGANISM: Artificial Sequence
<220> FEATURE:
<223> OTHER INFORMATION: ISVD derived sequence

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Leu Gly Ile Asn
            20                  25                  30

Ala Met Gly Trp Tyr Arg Gln Ala Pro Gly Lys Gln Arg Glu Leu Val
        35                  40                  45

Ala Val Ile Asn Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Glu Trp Gly Asp Tyr Pro Gly Gln Val Tyr Asp Tyr Trp Gly
            100                 105                 110

Gln Gly Thr Gln Val Thr Val Ser Ser
            115                 120

<210> SEQ ID NO 21
<211> LENGTH: 123
<212> TYPE: PRT
<213> ORGANISM: Artificial Sequence
<220> FEATURE:
<223> OTHER INFORMATION: ISVD derived sequence

<400> SEQUENCE: 21

Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Ser Leu Ser Asn Tyr
            20                  25                  30

Ala Met Gly Trp Phe Arg Gln Ala Pro Gly Lys Glu Arg Glu Ile Val
            35                  40                  45

Cys Ala Ile Ser Arg Ser Gly Ser Ile Thr Thr Tyr Ala Asp Ser Val
        50                  55                  60

Lys Gly Arg Phe Thr Ile Ala Lys Asp Asn Ala Ala Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Asp Pro Met Tyr Tyr Gly Ile Pro Asp Gln Asn Trp Asp Tyr
            100                 105                 110

Trp Gly Gln Gly Thr Gln Val Thr Val Ser Ser
            115                 120

<210> SEQ ID NO 22
<211> LENGTH: 127
<212> TYPE: PRT
<213> ORGANISM: Artificial Sequence
<220> FEATURE:
<223> OTHER INFORMATION: ISVD derived sequence

<400> SEQUENCE: 22

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Asn Val
            35                  40                  45

Ala Ala Ile Ser Ser Ser Gly Gly Tyr Thr Tyr Tyr Pro Asp Ser Val
        50                  55                  60

Lys Gly Arg Phe Thr Ile Ser Arg Asp Thr Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Gly Thr Gln Pro Asn Phe Gly Trp Gln Leu Leu Leu Gln Thr
            100                 105                 110

Glu Tyr Asp Tyr Trp Gly Gln Gly Thr Gln Val Thr Val Ser Ser
            115                 120                 125

<210> SEQ ID NO 23
<211> LENGTH: 126
<212> TYPE: PRT
<213> ORGANISM: Artificial Sequence
<220> FEATURE:
<223> OTHER INFORMATION: ISVD derived sequence

<400> SEQUENCE: 23

Glu Val Gln Leu Val Glu Ser Gly Gly Gly Leu Val Gln Ala Gly Gly
1               5                   10                  15

Ser Leu Arg Leu Ser Cys Ala Val Ser Gly Arg Thr Phe Ser Pro Tyr
            20                  25                  30

Thr Met Gly Trp Phe Arg Arg Ala Pro Gly Lys Glu Arg Glu Phe Val
            35                  40                  45

Ala Ala Arg Thr Trp Ser Gly Gly Val Ala Trp Tyr Ala Asp Ser Val
        50                  55                  60

Lys Gly Arg Phe Thr Ile Ser Ser Asp Asn Ala Glu Asn Met Val Tyr
65                  70                  75                  80

```
Leu Gln Met Asn Ser Leu Lys Pro Glu Asp Thr Ala Val Tyr Tyr Cys
                85                  90                  95

Ala Ala Lys Ser Pro Gly Arg Thr Tyr Ser Pro Arg Glu Glu Arg Ala
            100                 105                 110

Tyr Ala Arg Trp Gly Gln Gly Thr Gln Val Thr Val Ser Ser
        115                 120                 125

<210> SEQ ID NO 24
<211> LENGTH: 125
<212> TYPE: PRT
<213> ORGANISM: Artificial Sequence
<220> FEATURE:
<223> OTHER INFORMATION: ISVD derived sequence

<400> SEQUENCE: 24

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Asp Tyr
            20                  25                  30

Thr Met Gly Trp Phe Arg Gln Ala Pro Gly Lys Glu Arg Glu Phe Val
        35                  40                  45

Ala Arg Ile Asn Thr Gly Gly Pro Ile Thr Ser Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Asn Cys
                85                  90                  95

Ala Ala Arg Leu Pro Thr Lys Met Ser Pro Arg Asp Tyr Ser Ser Tyr
            100                 105                 110

Ala Tyr Arg Gly Gln Gly Thr Gln Val Thr Val Ser Ser
        115                 120                 125

<210> SEQ ID NO 25
<211> LENGTH: 117
<212> TYPE: PRT
<213> ORGANISM: Artificial Sequence
<220> FEATURE:
<223> OTHER INFORMATION: ISVD derived sequence

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Asn Leu Asn
            20                  25                  30

Pro Met Gly Trp Tyr Arg Gln Ala Pro Gly Lys Gln Arg Glu Leu Val
        35                  40                  45

Ala Thr Val Thr Gly Glu Gly Arg Thr Asn Tyr Ser Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Ala Phe Trp Ala Tyr Asp Asp Ala Tyr Trp Gly Gln Gly Thr Gln
            100                 105                 110

Val Thr Val Ser Ser
        115
```

-continued

```
<210> SEQ ID NO 26
<211> LENGTH: 123
<212> TYPE: PRT
<213> ORGANISM: Artificial Sequence
<220> FEATURE:
<223> OTHER INFORMATION: ISVD derived sequence

<400> SEQUENCE: 26

Glu Val Gln Leu Val Glu Ser Gly Gly Gly Leu Ala Gln Ala Gly Gly
1               5                   10                  15

Ser Leu Arg Leu Ser Cys Ala Ala Ser Gly Arg Ser Leu Ser Asn Tyr
            20                  25                  30

Ala Met Gly Trp Phe Arg Gln Ala Pro Gly Lys Glu Arg Glu Ile Val
        35                  40                  45

Cys Ala Ile Ser Arg Ser Gly Ser Ile Thr Thr Tyr Ala Asp Ser Val
    50                  55                  60

Lys Gly Arg Phe Thr Ile Ala Lys Asp Asn Ala Ala Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Asp Pro Met Tyr Tyr Gly Ile Pro Asp Gln Asn Trp Asp Tyr
            100                 105                 110

Trp Gly Gln Gly Thr Gln Val Thr Val Ser Ser
        115                 120

<210> SEQ ID NO 27
<211> LENGTH: 122
<212> TYPE: PRT
<213> ORGANISM: Artificial Sequence
<220> FEATURE:
<223> OTHER INFORMATION: ISVD derived sequence

<400> SEQUENCE: 27

Glu Val Gln Leu Val Glu Ser Gly Gly Gly Leu Val Gln Ala Gly Gly
1               5                   10                  15

Ser Leu Arg Leu Ser Cys Ala Asp Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Gly Val Asn Trp Ser Gly Asp Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Ala Ala Val Tyr Tyr Cys
                85                  90                  95

Ala Ala Asp Pro Val Gly Arg Ala Asp Leu Tyr Glu Tyr Asp Tyr Trp
            100                 105                 110

Gly Gln Gly Thr Gln Val Thr Val Ser Ser
        115                 120

<210> SEQ ID NO 28
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 28

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Arg Thr Phe Ser
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 30

Glu Val Gln Leu Val Glu Ser Gly Gly Gly Leu Val Gln Ala Gly Asp
1               5                   10                  15

Ser Leu Arg Leu Ser Cys Ala Ala Ser Gly Gly Thr Phe Gly
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 31

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 33

Glu Val Gln Leu Val Glu Ser Gly Gly Gly Leu Val Gln Ala Gly Gly
```

-continued

```
                1               5                  10                  15
Ser Leu Arg Leu Ser Cys Ala Ala Ser Gly Arg Thr Asp Ser
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 34

Glu Val Gln Leu Val Glu Ser Gly Gly Gly Leu Val Gln Pro Gly Gly
1               5                  10                  15

Ser Leu Arg Leu Ser Cys Ala Ala Ser Gly Ser Ile Leu Gly
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 35

Glu Val Gln Leu Val Glu Ser Gly Gly Gly Leu Ala Gln Ala Gly Gly
1               5                  10                  15

Ser Leu Arg Leu Ser Cys Ala Ala Ser Gly Arg Ser Leu Ser
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 36

Glu Val Gln Leu Met Glu Ser Gly Gly Gly Leu Val Gln Ala Gly Gly
1               5                  10                  15

Ser Leu Arg Leu Ser Cys Ala Ala Ser Gly Arg Thr Phe Ser
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 37

Glu Val Gln Leu Val Glu Ser Gly Gly Gly Leu Val Gln Ala Gly Gly
1               5                  10                  15

Ser Leu Arg Leu Ser Cys Ala Val Ser Gly Arg Thr Phe Ser
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 38
```

-continued

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: ISVD derived sequence

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Asn
            20                  25                  30

<210> SEQ ID NO 40
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 40

Ser Tyr Ala Met Gly
1               5

<210> SEQ ID NO 41
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 41

His Tyr Thr Ile Gly
1               5

<210> SEQ ID NO 42
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 42

Ser Ser His Met Ala
1               5

<210> SEQ ID NO 43
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 43

Ser Tyr Ala Met Gly
1               5

<210> SEQ ID NO 44
<211> LENGTH: 5
<212> TYPE: PRT
<213> ORGANISM: Artificial Sequence

```
<220> FEATURE:
<223> OTHER INFORMATION: ISVD derived sequence

<400> SEQUENCE: 44

Asp Tyr Ala Met Ser
1               5

<210> SEQ ID NO 45
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 45

Ser Tyr Ala Met Gly
1               5

<210> SEQ ID NO 46
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 46

Ile Asn Ala Met Gly
1               5

<210> SEQ ID NO 47
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 47

Asn Tyr Ala Met Gly
1               5

<210> SEQ ID NO 48
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 48

Ser Tyr Ala Met Gly
1               5

<210> SEQ ID NO 49
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 49

Pro Tyr Thr Met Gly
1               5

<210> SEQ ID NO 50
<211> LENGTH: 5
<212> TYPE: PRT
<213> ORGANISM: Artificial Sequence
<220> FEATURE:
```

<223> OTHER INFORMATION: ISVD derived sequence

<400> SEQUENCE: 50

Asp Tyr Thr Met Gly
1               5

<210> SEQ ID NO 51
<211> LENGTH: 5
<212> TYPE: PRT
<213> ORGANISM: Artificial Sequence
<220> FEATURE:
<223> OTHER INFORMATION: ISVD derived sequence

<400> SEQUENCE: 51

Leu Asn Pro Met Gly
1               5

<210> SEQ ID NO 52
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 52

Trp Phe Arg Gln Ala Pro Gly Lys Glu Arg Glu Phe Val Ala
1               5                   10

<210> SEQ ID NO 53
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 53

Trp Phe Arg Gln Ala Pro Gly Asn Glu Arg Glu Gly Val Ser
1               5                   10

<210> SEQ ID NO 54
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 54

Trp Phe Arg Gln Val Pro Glu Lys Glu Arg Glu Phe Val Ala
1               5                   10

<210> SEQ ID NO 55
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 55

Trp Phe Arg Gln Ala Pro Gly Lys Glu Arg Glu Phe Val Ala
1               5                   10

<210> SEQ ID NO 56
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 56

Trp Gly Arg Gln Ala Pro Gly Lys Gly Leu Glu Trp Val Ser
1               5                   10

<210> SEQ ID NO 57
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 57

Trp Phe Arg Gln Ala Pro Gly Lys Glu His Glu Phe Val Ala
1               5                   10

<210> SEQ ID NO 58
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 58

Trp Tyr Arg Gln Ala Pro Gly Lys Gln Arg Glu Leu Val Ala
1               5                   10

<210> SEQ ID NO 59
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 59

Trp Phe Arg Gln Ala Pro Gly Lys Glu Arg Glu Ile Val Cys
1               5                   10

<210> SEQ ID NO 60
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 60

Trp Phe Arg Gln Ala Pro Gly Lys Glu Arg Glu Asn Val Ala
1               5                   10

<210> SEQ ID NO 61
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 61

Trp Phe Arg Arg Ala Pro Gly Lys Glu Arg Glu Phe Val Ala
1               5                   10

<210> SEQ ID NO 62
<211> LENGTH: 14
<212> TYPE: PRT
<213> ORGANISM: Artificial Sequence
<220> FEATURE:
<223> OTHER INFORMATION: ISVD derived sequence

```
<400> SEQUENCE: 62

Trp Phe Arg Gln Ala Pro Gly Lys Glu Arg Glu Phe Val Ala
1               5                   10

<210> SEQ ID NO 63
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 63

Trp Tyr Arg Gln Ala Pro Gly Lys Gln Arg Glu Leu Val Ala
1               5                   10

<210> SEQ ID NO 64
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 64

Gly Ile Ser Trp Ser Gly Ser Ser Ser Tyr Tyr Ala Asp Ser Val Lys
1               5                   10                  15

Gly

<210> SEQ ID NO 65
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 65

Cys Ile Ser Ser Leu Asp Gly Ser Thr Tyr Tyr Ala Asp Ser Val Lys
1               5                   10                  15

Gly

<210> SEQ ID NO 66
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 66

Ala Ile Ser Arg Ser Gly Gly Thr Thr Tyr Tyr Ala Asp Ser Val Lys
1               5                   10                  15

Gly

<210> SEQ ID NO 67
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 67

Ala Ile Asn Trp Ser Gly Asp Ser Thr Tyr Tyr Ala Asp Ser Val Lys
1               5                   10                  15

Gly
```

```
<210> SEQ ID NO 68
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 68

Ala Ile Ser Trp Asn Gly Gly Ser Thr Tyr Tyr Ala Glu Ser Met Lys
1               5                   10                  15

Gly

<210> SEQ ID NO 69
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 69

Ala Ile Ser Trp Ser Gly Gly Ser Thr Tyr Tyr Ala Asp Ser Val Lys
1               5                   10                  15

Gly

<210> SEQ ID NO 70
<211> LENGTH: 16
<212> TYPE: PRT
<213> ORGANISM: Artificial Sequence
<220> FEATURE:
<223> OTHER INFORMATION: ISVD derived sequence

<400> SEQUENCE: 70

Val Ile Asn Ser Gly Gly Ser Thr Asn Tyr Ala Asp Ser Val Lys Gly
1               5                   10                  15

<210> SEQ ID NO 71
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 71

Ala Ile Ser Arg Ser Gly Ser Ile Thr Thr Tyr Ala Asp Ser Val Lys
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 72

Ala Ile Ser Ser Ser Gly Gly Tyr Thr Tyr Tyr Pro Asp Ser Val Lys
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: ISVD derived sequence
```

<400> SEQUENCE: 73

Ala Arg Thr Trp Ser Gly Gly Val Ala Trp Tyr Ala Asp Ser Val Lys
1               5                   10                  15
Gly

<210> SEQ ID NO 74
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 74

Arg Ile Asn Thr Gly Gly Pro Ile Thr Ser Tyr Ser Asp Ser Val Lys
1               5                   10                  15
Gly

<210> SEQ ID NO 75
<211> LENGTH: 16
<212> TYPE: PRT
<213> ORGANISM: Artificial Sequence
<220> FEATURE:
<223> OTHER INFORMATION: ISVD derived sequence

<400> SEQUENCE: 75

Thr Val Thr Gly Glu Gly Arg Thr Asn Tyr Ser Asp Ser Val Lys Gly
1               5                   10                  15

<210> SEQ ID NO 76
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 76

Arg Phe Thr Ile Ser Arg Asp Asn Ala Lys Asn Thr Val Tyr Leu Gln
1               5                   10                  15
Met Asn Ser Leu Lys Pro Glu Asp Thr Ala Val Tyr Tyr Cys Ala Ala
            20                  25                  30

<210> SEQ ID NO 77
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 77

Arg Phe Thr Ile Ser Arg Asp Asn Ala Lys Asp Thr Val Tyr Leu Gln
1               5                   10                  15
Met Asn Ser Leu Lys Pro Glu Asp Thr Ala Val Tyr Tyr Cys Ala Val
            20                  25                  30

<210> SEQ ID NO 78
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 78

Arg Cys Thr Ile Ser Arg Asp Asn Ala Lys Asn Thr Val Tyr Leu Gln

<210> SEQ ID NO 79
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 79

Arg Phe Thr Ile Ser Arg Asp Asn Ala Lys Asn Thr Val Tyr Leu Gln
1               5                   10                  15
Met Asn Ser Leu Lys Pro Glu Asp Thr Ala Val Tyr Tyr Cys Ala Ala
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 80

Arg Phe Thr Val Ser Arg Asp Asn Ala Lys Asn Thr Leu Tyr Leu Gln
1               5                   10                  15
Met Asn Ser Leu Lys Ser Glu Asp Thr Ala Val Tyr Tyr Cys Ala Lys
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 81

Arg Phe Thr Ile Ser Arg Asp Asn Ala Lys Asn Thr Leu Tyr Leu Gln
1               5                   10                  15
Met Asn Ser Leu Lys Pro Glu Asp Thr Ala Val Tyr Tyr Cys Gly Ala
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 82

Arg Phe Thr Ile Ser Arg Asp Asn Ala Lys Asn Thr Val Tyr Leu Gln
1               5                   10                  15
Met Asn Ser Leu Lys Pro Glu Asp Thr Ala Val Tyr Tyr Cys Asn Ala
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 83

Arg Phe Thr Ile Ala Lys Asp Asn Ala Ala Asn Thr Val Tyr Leu Gln
1               5                   10                  15

Met Asn Ser Leu Lys Pro Glu Asp Thr Ala Ala Tyr Tyr Cys Ala Ala
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 84

Arg Phe Thr Ile Ser Arg Asp Thr Ala Lys Asn Thr Val Tyr Leu Gln
1               5                   10                  15

Met Asn Ser Leu Lys Pro Asp Asp Thr Ala Val Tyr Tyr Cys Ala Gly
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 85

Arg Phe Thr Ile Ser Ser Asp Asn Ala Glu Asn Met Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 86

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Asn Cys Ala Ala
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: ISVD derived sequence

<400> SEQUENCE: 87

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Ala
            20                  25                  30

<210> SEQ ID NO 88
<211> LENGTH: 13
<212> TYPE: PRT
<213> ORGANISM: Artificial Sequence
<220> FEATURE:
<223> OTHER INFORMATION: ISVD derived sequence

<400> SEQUENCE: 88

```
Asp Pro Val Gly Arg Ala Asp Leu Tyr Glu Tyr Asp Tyr
1               5                   10
```

<210> SEQ ID NO 89
<211> LENGTH: 13
<212> TYPE: PRT
<213> ORGANISM: Artificial Sequence
<220> FEATURE:
<223> OTHER INFORMATION: ISVD derived sequence

<400> SEQUENCE: 89

```
Ala Gly Cys Gly Ala Tyr Gly Leu Ile Pro Tyr Asp Tyr
1               5                   10
```

<210> SEQ ID NO 90
<211> LENGTH: 16
<212> TYPE: PRT
<213> ORGANISM: Artificial Sequence
<220> FEATURE:
<223> OTHER INFORMATION: ISVD derived sequence

<400> SEQUENCE: 90

```
Ala Arg Phe Trp Gly Ser Thr Ser Thr Arg Met Asp Asp Tyr Gln Tyr
1               5                   10                  15
```

<210> SEQ ID NO 91
<211> LENGTH: 13
<212> TYPE: PRT
<213> ORGANISM: Artificial Sequence
<220> FEATURE:
<223> OTHER INFORMATION: ISVD derived sequence

<400> SEQUENCE: 91

```
Gly Asp Val Gly Arg Pro Asp Leu Tyr Glu Tyr Asp Tyr
1               5                   10
```

<210> SEQ ID NO 92
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 92

```
Ala Leu Asp Pro Leu Gly Val Leu Ala Gly Thr Ser Gly Ile Tyr Asp
1               5                   10                  15

Tyr
```

<210> SEQ ID NO 93
<211> LENGTH: 12
<212> TYPE: PRT
<213> ORGANISM: Artificial Sequence
<220> FEATURE:
<223> OTHER INFORMATION: ISVD derived sequence

<400> SEQUENCE: 93

```
Ser Tyr Arg Trp Gly Ile Thr His Glu Tyr Glu Tyr
1               5                   10
```

<210> SEQ ID NO 94
<211> LENGTH: 13
<212> TYPE: PRT
<213> ORGANISM: Artificial Sequence
<220> FEATURE:
<223> OTHER INFORMATION: ISVD derived sequence

```
<400> SEQUENCE: 94

Asp Glu Trp Gly Asp Tyr Pro Gly Gln Val Tyr Asp Tyr
1               5                   10

<210> SEQ ID NO 95
<211> LENGTH: 14
<212> TYPE: PRT
<213> ORGANISM: Artificial Sequence
<220> FEATURE:
<223> OTHER INFORMATION: ISVD derived sequence

<400> SEQUENCE: 95

Asp Pro Met Tyr Tyr Gly Ile Pro Asp Gln Asn Trp Asp Tyr
1               5                   10

<210> SEQ ID NO 96
<211> LENGTH: 18
<212> TYPE: PRT
<213> ORGANISM: Artificial Sequence
<220> FEATURE:
<223> OTHER INFORMATION: ISVD derived sequence

<400> SEQUENCE: 96

Thr Gln Pro Asn Phe Gly Trp Gln Leu Leu Leu Leu Gln Thr Glu Tyr
1               5                   10                  15

Asp Tyr

<210> SEQ ID NO 97
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 97

Lys Ser Pro Gly Arg Thr Tyr Ser Pro Arg Glu Glu Arg Ala Tyr Ala
1               5                   10                  15

Arg

<210> SEQ ID NO 98
<211> LENGTH: 16
<212> TYPE: PRT
<213> ORGANISM: Artificial Sequence
<220> FEATURE:
<223> OTHER INFORMATION: ISVD derived sequence

<400> SEQUENCE: 98

Arg Leu Pro Thr Lys Met Ser Pro Arg Asp Tyr Ser Ser Tyr Ala Tyr
1               5                   10                  15

<210> SEQ ID NO 99
<211> LENGTH: 9
<212> TYPE: PRT
<213> ORGANISM: Artificial Sequence
<220> FEATURE:
<223> OTHER INFORMATION: ISVD derived sequence

<400> SEQUENCE: 99

Ala Phe Trp Ala Tyr Asp Asp Ala Tyr
1               5

<210> SEQ ID NO 100
<211> LENGTH: 11
<212> TYPE: PRT
<213> ORGANISM: Artificial Sequence
```

```
<220> FEATURE:
<223> OTHER INFORMATION: ISVD derived sequence

<400> SEQUENCE: 100

Trp Gly Gln Gly Thr Gln Val Thr Val Ser Ser
1               5                   10

<210> SEQ ID NO 101
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 101

Trp Gly Gln Gly Thr Gln Val Thr Val Ser Ser
1               5                   10

<210> SEQ ID NO 102
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 102

Trp Gly Gln Gly Thr Gln Val Thr Val Ser Ser
1               5                   10

<210> SEQ ID NO 103
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 103

Trp Gly Gln Gly Thr Gln Val Thr Val Ser Ser
1               5                   10

<210> SEQ ID NO 104
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 104

Trp Gly Gln Gly Thr Gln Val Thr Val Ser Ser
1               5                   10

<210> SEQ ID NO 105
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 105

Trp Gly Gln Gly Thr Gln Val Thr Val Ser Ser
1               5                   10

<210> SEQ ID NO 106
<211> LENGTH: 11
<212> TYPE: PRT
<213> ORGANISM: Artificial Sequence
<220> FEATURE:
```

```
<223> OTHER INFORMATION: ISVD derived sequence

<400> SEQUENCE: 106

Trp Gly Gln Gly Thr Gln Val Thr Val Ser Ser
1               5                   10

<210> SEQ ID NO 107
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 107

Trp Gly Gln Gly Thr Gln Val Thr Val Ser Ser
1               5                   10

<210> SEQ ID NO 108
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 108

Trp Gly Gln Gly Thr Gln Val Thr Val Ser Ser
1               5                   10

<210> SEQ ID NO 109
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 109

Trp Gly Gln Gly Thr Gln Val Thr Val Ser Ser
1               5                   10

<210> SEQ ID NO 110
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 110

Arg Gly Gln Gly Thr Gln Val Thr Val Ser Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: ISVD derived sequence

<400> SEQUENCE: 111

Trp Gly Gln Gly Thr Gln Val Thr Val Ser Ser
1               5                   10

<210> SEQ ID NO 112
<211> LENGTH: 280
<212> TYPE: PRT
<213> ORGANISM: Artificial Sequence
<220> FEATURE:
<223> OTHER INFORMATION: ISVD derived sequence
```

-continued

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Gly Ile Ser Trp Ser Gly Ser Ser Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Val Gly Arg Ala Asp Leu Tyr Glu Tyr Asp Tyr Trp
            100                 105                 110

Gly Gln Gly Thr Gln Val Thr Val Ser Gly Gly Gly Gly Ser Gly
        115                 120                 125

Gly Gly Ser Glu Val Gln Leu Val Glu Ser Gly Gly Gly Leu Val Gln
130                 135                 140

Pro Gly Asn Ser Leu Arg Leu Ser Cys Ala Ala Ser Gly Phe Thr Phe
145                 150                 155                 160

Ser Ser Phe Gly Met Ser Trp Val Arg Gln Ala Pro Gly Lys Gly Leu
                165                 170                 175

Glu Trp Val Ser Ser Ile Ser Gly Ser Gly Ser Asp Thr Leu Tyr Ala
            180                 185                 190

Asp Ser Val Lys Gly Arg Phe Thr Ile Ser Arg Asp Asn Ala Lys Thr
        195                 200                 205

Thr Leu Tyr Leu Gln Met Asn Ser Leu Arg Pro Glu Asp Thr Ala Val
    210                 215                 220

Tyr Tyr Cys Thr Ile Gly Gly Ser Leu Ser Arg Ser Gln Gly Thr
225                 230                 235                 240

Leu Val Thr Val Ser Ser Gly Ala Ala Asp Tyr Lys Asp His Asp Gly
                245                 250                 255

Asp Tyr Lys Asp His Asp Ile Asp Tyr Lys Asp Asp Asp Asp Lys Gly
            260                 265                 270

Ala Ala His His His His His His
        275                 280

<210> SEQ ID NO 113
<211> LENGTH: 279
<212> TYPE: PRT
<213> ORGANISM: Artificial Sequence
<220> FEATURE:
<223> OTHER INFORMATION: ISVD derived sequence

<400> SEQUENCE: 113

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Asp Ser Ser Tyr
            20                  25                  30

Ala Met Gly Trp Phe Arg Gln Ala Pro Gly Lys Glu His Glu Phe Val
        35                  40                  45

Ala Ala Ile Ser Trp Ser Gly Ser Thr Tyr Tyr Ala Asp Ser Val
    50                  55                  60

```
Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Gly Ala Ser Tyr Arg Trp Gly Ile Thr His Glu Tyr Glu Tyr Trp Gly
            100                 105                 110

Gln Gly Thr Gln Val Thr Val Ser Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
            165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
            195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser Gly Ala Ala Asp Tyr Lys Asp His Asp Gly Asp
                245                 250                 255

Tyr Lys Asp His Asp Ile Asp Tyr Lys Asp Asp Asp Asp Lys Gly Ala
            260                 265                 270

Ala His His His His His His
            275

<210> SEQ ID NO 114
<211> LENGTH: 115
<212> TYPE: PRT
<213> ORGANISM: Artificial Sequence
<220> FEATURE:
<223> OTHER INFORMATION: ISVD derived sequence

<400> SEQUENCE: 114

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 115
<211> LENGTH: 138
```

<212> TYPE: PRT
<213> ORGANISM: Artificial Sequence
<220> FEATURE:
<223> OTHER INFORMATION: ISVD derived sequence

<400> SEQUENCE: 115

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala Glu Gln Lys Leu Ile Ser Glu Glu Asp Leu
        115                 120                 125

Asn Gly Ala Ala His His His His His His
    130                 135

<210> SEQ ID NO 116
<211> LENGTH: 34
<212> TYPE: PRT
<213> ORGANISM: Artificial Sequence
<220> FEATURE:
<223> OTHER INFORMATION: tag

<400> SEQUENCE: 116

Gly Ala Ala Asp Tyr Lys Asp His Asp Gly Asp Tyr Lys Asp His Asp
1               5                   10                  15

Ile Asp Tyr Lys Asp Asp Asp Asp Lys Gly Ala Ala His His His His
            20                  25                  30

His His

<210> SEQ ID NO 117
<211> LENGTH: 5
<212> TYPE: PRT
<213> ORGANISM: Artificial Sequence
<220> FEATURE:
<223> OTHER INFORMATION: synthetic linker

<400> SEQUENCE: 117

Gly Gly Gly Gly Ser
1               5

<210> SEQ ID NO 118
<211> LENGTH: 7
<212> TYPE: PRT
<213> ORGANISM: Artificial Sequence
<220> FEATURE:
<223> OTHER INFORMATION: synthetic linker

<400> SEQUENCE: 118

Ser Gly Gly Ser Gly Gly Ser
1               5

```
<210> SEQ ID NO 119
<211> LENGTH: 9
<212> TYPE: PRT
<213> ORGANISM: Artificial Sequence
<220> FEATURE:
<223> OTHER INFORMATION: synthetic linker

<400> SEQUENCE: 119

Gly Gly Gly Gly Ser Gly Gly Gly Ser
1               5

<210> SEQ ID NO 120
<211> LENGTH: 10
<212> TYPE: PRT
<213> ORGANISM: Artificial Sequence
<220> FEATURE:
<223> OTHER INFORMATION: synthetic linker

<400> SEQUENCE: 120

Gly Gly Gly Gly Ser Gly Gly Gly Gly Ser
1               5                   10

<210> SEQ ID NO 121
<211> LENGTH: 15
<212> TYPE: PRT
<213> ORGANISM: Artificial Sequence
<220> FEATURE:
<223> OTHER INFORMATION: synthetic linker

<400> SEQUENCE: 121

Gly Gly Gly Gly Ser Gly Gly Gly Gly Ser Gly Gly Gly Gly Ser
1               5                   10                  15

<210> SEQ ID NO 122
<211> LENGTH: 18
<212> TYPE: PRT
<213> ORGANISM: Artificial Sequence
<220> FEATURE:
<223> OTHER INFORMATION: synthetic linker

<400> SEQUENCE: 122

Gly Gly Gly Gly Ser Gly Gly Gly Gly Ser Gly Gly Gly Gly Gly
1               5                   10                  15

Gly Ser

<210> SEQ ID NO 123
<211> LENGTH: 20
<212> TYPE: PRT
<213> ORGANISM: Artificial Sequence
<220> FEATURE:
<223> OTHER INFORMATION: synthetic linker

<400> SEQUENCE: 123

Gly Gly Gly Gly Ser Gly Gly Gly Gly Ser Gly Gly Gly Gly Ser Gly
1               5                   10                  15

Gly Gly Gly Ser
            20

<210> SEQ ID NO 124
<211> LENGTH: 25
<212> TYPE: PRT
<213> ORGANISM: Artificial Sequence
<220> FEATURE:
<223> OTHER INFORMATION: synthetic linker

<400> SEQUENCE: 124
```

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 125
<211> LENGTH: 30
<212> TYPE: PRT
<213> ORGANISM: Artificial Sequence
<220> FEATURE:
<223> OTHER INFORMATION: synthetic linker

<400> SEQUENCE: 125

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 126
<211> LENGTH: 35
<212> TYPE: PRT
<213> ORGANISM: Artificial Sequence
<220> FEATURE:
<223> OTHER INFORMATION: synthetic linker

<400> SEQUENCE: 126

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 127
<211> LENGTH: 98
<212> TYPE: PRT
<213> ORGANISM: Artificial Sequence
<220> FEATURE:
<223> OTHER INFORMATION: ISVD derived sequence

<400> SEQUENCE: 127

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala

<210> SEQ ID NO 128
<211> LENGTH: 5
<212> TYPE: PRT
<213> ORGANISM: Artificial Sequence
<220> FEATURE:
<223> OTHER INFORMATION: ISVD derived sequence

```
<400> SEQUENCE: 128

Ser Phe Gly Met Ser
1               5

<210> SEQ ID NO 129
<211> LENGTH: 17
<212> TYPE: PRT
<213> ORGANISM: Artificial Sequence
<220> FEATURE:
<223> OTHER INFORMATION: ISVD derived sequence

<400> SEQUENCE: 129

Ser Ile Ser Gly Ser Gly Ser Asp Thr Leu Tyr Ala Asp Ser Val Lys
1               5                   10                  15

Gly

<210> SEQ ID NO 130
<211> LENGTH: 6
<212> TYPE: PRT
<213> ORGANISM: Artificial Sequence
<220> FEATURE:
<223> OTHER INFORMATION: ISVD derived sequence

<400> SEQUENCE: 130

Gly Gly Ser Leu Ser Arg
1               5
```